US010179781B2

(12) United States Patent
Babich et al.

(10) Patent No.: US 10,179,781 B2
(45) **Date of Patent: *Jan. 15, 2019**

(54) SODIUM CHANNEL MODULATORS FOR THE TREATMENT OF PAIN

(71) Applicant: CHROMOCELL CORPORATION, North Brunswick, NJ (US)

(72) Inventors: Olga Babich, Cranford, NJ (US); Robert Z. Luo, New City, NY (US); Yanlin Wang-Fischer, Hillsborough, NJ (US); David J. Palling, Glen Ridge, NJ (US); Srinivasan P. Venkatachalan, Monmouth Junction, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/776,016

(22) PCT Filed: Mar. 13, 2014

(86) PCT No.: PCT/US2014/025809

§ 371 (c)(1),
(2) Date: Sep. 14, 2015

(87) PCT Pub. No.: WO2014/151472

PCT Pub. Date: Sep. 25, 2014

(65) Prior Publication Data

US 2016/0046617 A1 Feb. 18, 2016

Related U.S. Application Data

(60) Provisional application No. 61/787,618, filed on Mar. 15, 2013.

(51) Int. Cl.
*C07D 417/12* (2006.01)
*C07D 277/52* (2006.01)
*C07D 285/08* (2006.01)
*C07D 487/04* (2006.01)

(52) U.S. Cl.
CPC ......... *C07D 417/12* (2013.01); *C07D 277/52* (2013.01); *C07D 285/08* (2013.01); *C07D 487/04* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,624,931 | A | 4/1997 | Oku et al. | |
| 7,230,020 | B2 | 6/2007 | Vicker et al. | |
| 7,384,967 | B2 | 6/2008 | Vicker et al. | |
| 8,153,814 | B2 | 4/2012 | Beaudoin et al. | |
| 8,410,054 | B2 | 4/2013 | Macdonald et al. | |
| 8,476,434 | B2 | 7/2013 | Geuns-Meyer et al. | |
| 8,541,588 | B2 | 9/2013 | Beaudoin et al. | |
| 8,772,293 | B2 | 7/2014 | Brown et al. | |
| 8,895,608 | B2 | 11/2014 | Iadonato et al. | |
| 8,907,101 | B2 | 12/2014 | Beaudoin et al. | |
| 9,458,118 | B2 * | 10/2016 | Babich ................. | C07D 417/12 |
| 2004/0127508 | A1 | 7/2004 | Gerlach et al. | |
| 2006/0009453 | A1 | 1/2006 | Geuns-Meyer et al. | |
| 2007/0037796 | A1 | 2/2007 | Barda et al. | |
| 2008/0312235 | A1 | 12/2008 | Lane et al. | |
| 2009/0023740 | A1 | 1/2009 | Fulp et al. | |
| 2010/0197655 | A1 | 8/2010 | Beaudoin et al. | |
| 2010/0249206 | A1 | 9/2010 | Larsen et al. | |
| 2010/0267782 | A1 | 10/2010 | Beaudoin et al. | |
| 2012/0010182 | A1 | 1/2012 | Brown et al. | |
| 2012/0010207 | A1 | 1/2012 | Bell et al. | |
| 2012/0101105 | A1 | 4/2012 | Inoue et al. | |
| 2012/0149679 | A1 | 6/2012 | Beaudoin et al. | |
| 2013/0109667 | A1 | 5/2013 | Markworth et al. | |
| 2013/0338111 | A1 | 12/2013 | Beaudoin et al. | |
| 2014/0221286 | A1 | 8/2014 | Belardinelli et al. | |
| 2016/0221974 | A1 | 8/2016 | Babich et al. | |

FOREIGN PATENT DOCUMENTS

| | | |
|---|---|---|
| WO | WO 2006/046916 | 5/2006 |
| WO | WO 2010/079443 | 7/2010 |
| WO | WO 2012/004706 | 1/2012 |
| WO | WO 2012/004714 | 1/2012 |
| WO | WO 2012/004743 | 1/2012 |
| WO | WO 2012/099983 | 7/2012 |
| WO | WO 2013/025883 | 2/2013 |
| WO | WO 2013/043925 | 3/2013 |
| WO | WO 2013/064984 | 5/2013 |
| WO | WO 2014/078479 | 5/2014 |
| WO | WO 2014/151472 | 9/2014 |
| WO | WO 2015/035223 | 3/2015 |
| WO | WO 2015/038533 | 3/2015 |
| WO | PCT/US2015/048927 | 9/2015 |

OTHER PUBLICATIONS

Cox et al., "An SCN9A channelopathy causes congenital inability to experience pain", Nature, Dec. 14, 2006;444(7121): 894-98.

(Continued)

*Primary Examiner* — James D. Anderson

(57) ABSTRACT

Provided herein are sodium channel modulating Compounds, in particular NaV1.7 modulating compounds of Formula I:

Formula (I)

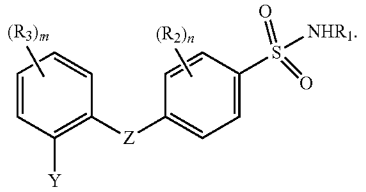

In particular, provided herein are processes for the preparation of, intermediates used in the preparation of, pharmaceutical compositions comprising, and therapeutic methods comprising administering such compounds. In particular, provided herein are compounds for the treatment of pain.

22 Claims, No Drawings

(56) References Cited

OTHER PUBLICATIONS

Written Opinion for PCT/US2015/48927 dated Dec. 8, 2015.
Notice of Allowance and Fee(s) Due for U.S. Appl. No. 14/944,846, dated Aug. 1, 2016.
Supplemental Notice of Allowability for U.S. Appl. No. 14/944,846, dated Aug. 17, 2016.
Supplemental Partial European Search Report for European Patent Application No. 14767550.8, dated Jun. 22, 2016.
Supplemental European Search Report for European Patent Application No. 14767550.8, dated Sep. 13, 2016.
U.S. Appl. No. 14/994,846, filed Jan. 13, 2016, Babich et al.
International Search Report and Written Opinion of International Patent Application No. PCT/US2014/054764 dated Nov. 13, 2014.
International Search Report and Written Opinion of International Patent Application No. PCT/US2014/025809 dated Jul. 7, 2014.
International Search Report of International Patent Application No. PCT/US2015/48927 dated Dec. 8, 2015.
Bagal et al., 2014, "Recent progress in sodium channel modulators for pain", Biorgan. Med. Chem. Lett., 24(16):3690-3699.
Minett et al., 2012, "Distinct Nav1.7 dependent pain sensations require different sets of sensory and sympathetic neurons", Nature Communications, 3:791.
McCormack et al., 2013, "Voltage sensor interaction site for selective small molecule inhibitors of voltage-gated sodium channels", PNAS, 110(29):E2724-32.
Norinder et al., 2013, "QSAR investigation of NaV1.7 active compounds using the SVM/Signature approach and the Bioclipse Modeling platform", Biorg. Med. Chem. Lett., 23(1):261-263.
Shields et al., 2012, "Sodium channel $Na_v1.7$ is essential for lowering heat pain threshold after burn injury", J. of Neuroscience, 32(32):10819-10832.
International Preliminary Report on Patentability dated Mar. 23, 2017 for PCT/US2015/048927.
Extended European Search Report dated Jan. 5, 2017 for European Patent Application No. 14843353.5.
U.S. Appl. No. 14/994,846, filed Jan. 13, 2016, was issued as U.S. Pat. No. 9,458,118 on Oct. 4, 2016.
US. Appl. No. 15/021,153, filed Mar. 10, 2016, still pending.

* cited by examiner

SODIUM CHANNEL MODULATORS FOR THE TREATMENT OF PAIN

This application is a national stage entry of International Patent Application No. PCT/US2014/025809, filed Mar. 13, 2014, which claims the benefit of U.S. provisional application No. 61/787,618 filed Mar. 15, 2013, which is incorporated by reference herein in its entirety.

1 FIELD

Provided herein are sodium channel modulating compounds, in particular NaV1.7 modulating compounds. In particular, provided herein are processes for the preparation of, intermediates used in the preparation of, pharmaceutical compositions comprising, and therapeutic methods comprising administering compounds. In particular, provided herein are compounds for the treatment of pain.

2 BACKGROUND

Voltage-gated ion channels play a critical role in the electrical activity of neuronal and muscle cells. Large families of voltage-gated ion channels (e.g., sodium channels) have been identified. These ion channels have been the target of significant pharmacologic study, due to their potential role in a variety of pathological conditions. Biophysical and pharmacological studies have identified the sodium channel isoforms NaV1.3, NaV1.7, NaV1.8, and NaV1.9 as particularly important in the pathophysiology of pain, in particular neuropathic pain. Recently, gain-of-function mutations in SCN9A, the gene which encodes NaV1.7, have been linked to two human-inherited pain syndromes, inherited erythromelalgia and paroxysmal extreme pain disorder, while loss-of-function mutations in SCN9A have been linked to complete insensitivity to pain. Dib-Hajj et al, *Pain Medicine* 10(7):1260-1269 (2009) (abstract). Pain conditions affect approximately 100 million U.S. adults at a cost of $560-635 billion annually in direct medical treatment costs and lost productivity. Relieving Pain in America, *National Academies Press*, Washington, D.C. (2011), page 2. Unfortunately, current treatment options typically provide only partial pain relief, and are limited by inconvenient dosing and by side effects, such as somnolence, ataxia, edema, gastrointestinal discomfort and respiratory depression. Therefore, novel compounds are desirable to address the shortcomings of presently available treatment options.

3 SUMMARY

Provided herein are compounds of Formula (I),

Formula (I)

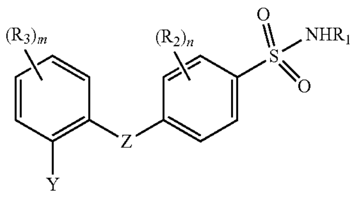

or a pharmaceutically acceptable salt, or a stereoisomeric or tautomeric form thereof, wherein:

Z is —O— or —S—;

Y is —X—C(=O)$NR_4R_5$, —$(CH_2)_3$—$NR_9R_{10}$, or 4,5,6,7-tetrahydropyrazolo[1,5-a]pyrimidine-(2-yl or 3-yl);

X is $(C_6$-$C_{10})$aryl or 5- or 6-membered heteroaryl;

$R_1$ is a partially unsaturated or aromatic 5- or 6-membered heterocycle;

$R_2$ is independently at each occurrence —F, —Cl, —Br, —$CH_3$ or —CN;

$R_3$ is independently at each occurrence —H, —F, —Cl, —Br, —$CF_3$, —$OCF_3$, —CN, $(C_1$-$C_{12})$alkyl, or $(C_1$-$C_{12})$alkoxy;

$R_4$ and $R_5$ are each independently H, $(C_1$-$C_9)$alkyl, $(C_4$-$C_{12})$cycloalkyl, or $R_4$ and $R_5$ together form a 5- to 7-membered heterocycloalkyl ring; with the proviso that:

$R_4$ and $R_5$ are not both H; and at least one of $R_4$ and $R_5$ independently or said heterocycloalkyl ring formed by $R_4$ and $R_5$ together is substituted with 1 or 2 substituents selected from the group consisting of —$CO_2H$, —$CO_2R_6$, —CN, —OH, —$CONR_7R_8$, and —$NR_7R_8$; wherein:

$R_6$ is $(C_1$-$C_{12})$alkyl;

$R_7$ and $R_8$ are each independently H, $(C_1$-$C_{12})$alkyl, or $R_7$ and $R_8$ together form a 4- to 7-membered heterocycloalkyl ring;

$R_9$ is $(C_1$-$C_6)$alkyl, $(C_3$-$C_8)$cycloalkyl, pyrazolyl or pyridinyl; wherein $R_9$ is optionally further substituted with 1 or 2 substituents selected from the group consisting of —COOH, —$COOR_{11}$, —$CONR_{11}R_{12}$, —$SO_2R_{11}$, —$SO_2NR_{11}R_{12}$, —OH, —CN, —$OR_{11}$, and —$NR_{11}R_{12}$; wherein $R_{11}$ and $R_{12}$ may form a 6 membered heterocycloalkyl ring $R_{10}$ is $R_{11}$, —$COR_{11}$, —$COOR_{11}$, —$SO_2R_{11}$, 5-methyl-2-oxo-1,3-dioxol-4-yl,

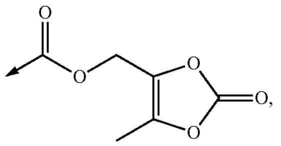

—COO—$CH(CH_3)OCOCH(CH_3)_2$; or $R_9$ and $R_{10}$ together form a piperazinone or a 4- to 8-membered heterocycloalkyl ring, wherein said heterocycloalkyl ring is substituted with 1 or 2 substituents selected from the group consisting of —COOH, —$COOR_{11}$, —$CH_2$—$COOR_{11}$, —OH, —$NH_2$, —CN, and $(C_1$-$C_8)$alkoxy;

$R_{11}$ and $R_{12}$ are independently H or $(C_1$-$C_6)$alkyl, optionally substituted with 4- to 8-membered heterocycloalkyl ring; and m and n are each independently 1, 2, 3, or 4.

In a certain embodiment, the compounds of Formula (I) are those wherein Y is —$(CH_2)_3$—$NR_9R_{10}$.

In a particular embodiment, the compounds of Formula (I) are those wherein $R_1$ is an aromatic 5- or 6-membered heterocycle, with 1-3 heteroatoms independently selected from the group consisting of N, O, and S.

In a particular embodiment, the compounds of Formula (I) are those wherein $R_1$ is pyridyl or pyrimidinyl.

In a particular embodiment, the compounds of Formula (I) are those wherein $R_1$ is an aromatic 5-membered heterocycle with 1 or 2 nitrogen atoms and optionally 1 or 2 sulphur atoms. In a particular embodiment, the compounds of Formula (I) are those wherein $R_1$ is thiazolyl, isothiazolyl, or thiadiazolyl. In a particular embodiment, the compounds of Formula (I) are those wherein $R_1$ is thiazolyl. In a particular embodiment, the compounds of Formula (I) are those wherein $R_1$ is 1,2,4-thiadiazol-5-yl.

In a particular embodiment, the compounds of Formula (I) are those wherein $R_2$ is independently at each occurrence —F or —Cl.

In a particular embodiment, the compounds of Formula (I) are those wherein n is 1, 2, or 3. In a particular embodiment, the compounds of Formula (I) are those wherein n is 2.

In a particular embodiment, the compounds of Formula (I) are those wherein Z is —O—.

In a particular embodiment, the compounds of Formula (I) are those wherein $R_3$ is independently at each occurrence —H, —F, —Cl, or —Br. In a particular embodiment, the compounds of Formula (I) are those wherein $R_3$ is —H or —Cl. In a particular embodiment, the compounds of Formula (I) are those wherein $R_3$ is —Cl.

In a particular embodiment, the compounds of Formula (I) are those wherein m is 1, 2, or 3. In a particular embodiment, the compounds of Formula (I) are those wherein m is 1.

In a particular embodiment, the compounds of Formula (I) are those wherein $R_9$ is $(C_1\text{-}C_6)$alkyl; wherein $R_9$ is optionally further substituted with 1 or 2 substituents selected from the group consisting of —COOH, —COOMe, —$CONH_2$, and —$NH_2$. In a particular embodiment, the compounds of Formula (I) are those wherein $R_9$ is methyl or ethyl. In a particular embodiment, the compounds of Formula (I) are those wherein $R_9$ is further substituted with —COOH.

In a particular embodiment, the compounds of Formula (I) are those wherein $R_{10}$ is —H, —COMe, —COOEt. In a particular embodiment, the compounds of Formula (I) are those wherein $R_{10}$ is —H or —COMe. In a particular embodiment, the compounds of Formula (I) are those wherein $R_{10}$ is —H.

In a particular embodiment, the compounds of Formula (I) are those wherein $R_9$ and $R_{10}$ together form a 4 to 8 membered heterocycloalkyl ring, wherein said heterocycloalkyl ring is substituted with 1 or 2 groups selected from the group consisting of —COOH, —COOMe, —COOEt, —$CH_2$—COOH, and —$NH_2$. In a particular embodiment, the compounds of Formula (I) are those wherein $R_9$ and $R_{10}$ together form a 4 to 8 membered heterocycloalkyl ring, wherein said heterocycloalkyl ring is substituted with 1 or 2 groups selected from the group consisting of —COOH, —$CH_2$—COOH, and —$NH_2$.

In a particular embodiment, the compounds of Formula (I) are those wherein $R_9$ and $R_{10}$ together form a piperidine substituted with 1 or 2 groups selected from the group consisting of —COOH, —COOMe, —COOEt, —$CH_2$—COOH, —$CH_2$—COOMe, —$CH_2$—COOEt, and —$NH_2$. In a particular embodiment, the compounds of Formula (I) are those wherein $R_9$ and $R_{10}$ together form a piperidine substituted with 1 or 2 groups selected from the group consisting of —COOH, —$CH_2$—COOH, and —$NH_2$.

In a certain embodiment, the compounds of Formula (I) are those wherein Y is —X—C(═O)$NR_4R_5$.

In a particular embodiment, the compounds of Formula (I) are those wherein $R_1$ is an aromatic 5- or 6-membered heterocycle, with 1-3 heteroatoms independently selected from the group consisting of N, O, and S.

In a particular embodiment, the compounds of Formula (I) are those wherein $R_1$ is pyridyl or pyrimidinyl.

In a particular embodiment, the compounds of Formula (I) are those wherein $R_1$ is an aromatic 5-membered heterocycle with 1 or 2 nitrogen atoms and optionally 1 or 2 sulphur atoms. In a particular embodiment, the compounds of Formula (I) are those wherein $R_1$ is thiazolyl, isothiazolyl, or thiadiazolyl. In a particular embodiment, the compounds of Formula (I) are those wherein $R_1$ is thiazolyl. In a particular embodiment, the compounds of Formula (I) are those wherein $R_1$ is 1,2,4-thiadiazol-5-yl.

In a particular embodiment, the compounds of Formula (I) are those wherein $R_2$ is independently at each occurrence —F or —Cl.

In a particular embodiment, the compounds of Formula (I) are those wherein n is 1, 2, or 3. In a particular embodiment, the compounds of Formula (I) are those wherein n is 2.

In a particular embodiment, the compounds of Formula (I) are those wherein Z is —O—.

In a particular embodiment, the compounds of Formula (I) are those wherein $R_3$ is independently at each occurrence —F, —Cl, or —Br. In a particular embodiment, the compounds of Formula (I) are those wherein $R_3$ is —H or —Cl. In a particular embodiment, the compounds of Formula (I) are those wherein $R_3$ is —Cl.

In a particular embodiment, the compounds of Formula (I) are those wherein m is 1, 2, or 3. In a particular embodiment, the compounds of Formula (I) are those wherein m is 1.

In a particular embodiment, the compounds of Formula (I) are those wherein X is 5- or 6-membered heteroaryl. In a particular embodiment, the compounds of Formula (I) are those wherein X is pyridyl or pyrimidinyl. In a particular embodiment, the compounds of Formula (I) are those wherein X is pyridyl.

In a particular embodiment, the compounds of Formula (I) are those wherein $R_4$ is H and $R_5$ is $(C_1\text{-}C_9)$alkyl.

In a particular embodiment, the compounds of Formula (I) are those wherein $R_5$ is methyl or ethyl, substituted with 1 or 2 substituents selected from the group consisting of —$CO_2H$, —$CO_2R_6$, and —$CONR_7R_8$.

In a particular embodiment, the compounds of Formula (I) are those wherein $R_6$ is $(C_1\text{-}C_6)$alkyl.

In a particular embodiment, the compounds of Formula (I) are those wherein $R_5$ is methyl or ethyl, substituted with —$CO_2H$.

In a certain embodiment, the compounds of Formula (I) are those wherein Y is 4,5,6,7-tetrahydropyrazolo[1,5-a]pyrimidine-(2-yl or 3-yl). In a particular embodiment, the compounds of Formula (I) are those wherein Y is 4,5,6,7-tetrahydropyrazolo[1,5-a]pyrimidine-3-yl.

In a particular embodiment, the compounds of Formula (I) are those wherein $R_1$ is an aromatic 5- or 6-membered heterocycle, with 1-3 heteroatoms independently selected from the group consisting of N, O, and S.

In a particular embodiment, the compounds of Formula (I) are those wherein $R_1$ is pyridyl or pyrimidinyl.

In a particular embodiment, the compounds of Formula (I) are those wherein $R_1$ is an aromatic 5-membered heterocycle with 1 or 2 nitrogen atoms and optionally 1 or 2 sulphur atoms. In a particular embodiment, the compounds of Formula (I) are those wherein $R_1$ is thiazolyl, isothiazolyl, or thiadiazolyl. In a particular embodiment, the compounds of Formula (I) are those wherein $R_1$ is thiazolyl. In a particular embodiment, the compounds of Formula (I) are those wherein $R_1$ is 1,2,4-thiadiazol-5-yl.

In a particular embodiment, the compounds of Formula (I) are those wherein $R_2$ is independently at each occurrence —F or —Cl.

In a particular embodiment, the compounds of Formula (I) are those wherein n is 1, 2, or 3. In a particular embodiment, the compounds of Formula (I) are those wherein n is 2.

In a particular embodiment, the compounds of Formula (I) are those wherein Z is —O—.

In a particular embodiment, the compounds of Formula (I) are those wherein $R_3$ is independently at each occurrence —F, —Cl, or —Br. In a particular embodiment, the compounds of Formula (I) are those wherein $R_3$ is —H or —Cl. In a particular embodiment, the compounds of Formula (I) are those wherein $R_3$ is —Cl.

In a particular embodiment, the compounds of Formula (I) are those wherein m is 1, 2, or 3. In a particular embodiment, the compounds of Formula (I) are those wherein m is 1.

In a certain embodiment, the compounds of Formula (I) are those wherein the compound is 3-(4-(2-(4-(N-(1,2,4-thiadiazol-5-yl)sulfamoyl)-2-chloro-5-fluorophenoxy)-5-chlorophenyl)picolinamido)propanoic acid,
2-(4-(2-(4-(N-(1,2,4-thiadiazol-5-yl)sulfamoyl)-2-chloro-5-fluorophenoxy)-5-chlorophenyl)picolinamido)acetic acid,
5-(4-(2-(4-(N-(1,2,4-thiadiazol-5-yl)sulfamoyl)-2-chloro-5-fluorophenoxy)-5-chlorophenyl)picolinamido)pentanoic acid,
4-(4-(2-(4-(N-(1,2,4-thiadiazol-5-yl)sulfamoyl)-2-chloro-5-fluorophenoxy)-5-chlorophenyl)picolinamido)butanoic acid,
2-(4-(2-(4-(N-(1,2,4-thiadiazol-5-yl)sulfamoyl)-2-chloro-5-fluorophenoxy)-5-chlorophenyl)picolinamido)propanoic acid,
(R)-2-(4-(2-(4-(N-(1,2,4-thiadiazol-5-yl)sulfamoyl)-2-chloro-5-fluorophenoxy)-5-chlorophenyl)picolinamido) propanoic acid,
2-(6-(2-(4-(N-(1,2,4-thiadiazol-5-yl)sulfamoyl)-2-chloro-5-fluorophenoxy)-5-chlorophenyl)picolinamido)acetic acid,
(S)-2-(4-(2-(4-(N-(1,2,4-thiadiazol-5-yl)sulfamoyl)-2-chloro-5-fluorophenoxy)-5-chlorophenyl)picolinamido) propanoic acid,
3-(4-(2-(4-(N-(1,2,4-thiadiazol-5-yl)sulfamoyl)-2-cyano-phenoxy)-5-chlorophenyl)picolinamido)propanoic acid,
3-(4-(2-(4-(N-(1,2,4-thiadiazol-5-yl)sulfamoyl)-2,5-difluorophenoxy)-5-chlorophenyl)picolinamido)propanoic acid,
2-((3-(5-chloro-2-(2-chloro-5-fluoro-4-(N-(thiazol-4-yl)sulfamoyl)phenoxy)phenyl)propyl)amino)acetic acid,
3-((3-(2-(4-(N-(1,2,4-thiadiazol-5-yl)sulfamoyl)-2-chloro-5-fluorophenoxy)-5-chlorophenyl)propyl)amino)propanoic acid,
2-((3-(5-chloro-2-(2-chloro-5-fluoro-4-(N-(thiazol-2-yl)sulfamoyl)phenoxy)phenyl)propyl)amino)acetic acid,
1-(3-(5-chloro-2-(2-chloro-5-fluoro-4-(N-(thiazol-4-yl)sulfamoyl)phenoxy)phenyl)propyl)piperidine-4-carboxylic acid,
3-((3-(5-chloro-2-(2-chloro-5-fluoro-4-(N-(thiazol-4-yl)sulfamoyl)phenoxy)phenyl)propyl)amino)propanoic acid,
4-amino-1-(3-(5-chloro-2-(2-chloro-5-fluoro-4-(N-(thiazol-4-yl)sulfamoyl)phenoxy)phenyl)propyl)piperidine-4-carboxylic acid,
2-amino-4-((3-(5-chloro-2-(2-chloro-5-fluoro-4-(N-(thiazol-4-yl)sulfamoyl)phenoxy)phenyl)propyl)amino)butanoic acid,
2-((3-(5-chloro-2-(2,5-difluoro-4-(N-(thiazol-2-yl)sulfamoyl)phenoxy)phenyl)propyl)amino)acetic acid,
1-(3-(5-chloro-2-(2-chloro-5-fluoro-4-(N-(thiazol-4-yl)sulfamoyl)phenoxy)phenyl)propyl)piperidine-3-carboxylic acid,
2-((3-(2-(4-(N-(1,2,4-thiadiazol-5-yl)sulfamoyl)-2-chloro-5-fluorophenoxy)phenyl)propyl)amino)acetic acid,
2-((3-(5-chloro-2-(2,5-difluoro-4-(N-(thiazol-4-yl)sulfamoyl)phenoxy)phenyl)propyl)amino)acetic acid,
3-((3-(5-chloro-2-(2,5-difluoro-4-(N-(thiazol-4-yl)sulfamoyl)phenoxy)phenyl)propyl)amino)propanoic acid,
3-((3-(5-chloro-2-(2-cyano-4-(N-(thiazol-4-yl)sulfamoyl) phenoxy)phenyl)propyl)amino)propanoic acid,
methyl 2-((3-(5-chloro-2-(2-chloro-5-fluoro-4-(N-(thiazol-4-yl)sulfamoyl)phenoxy)phenyl)propyl)amino)acetate,
3-((3-(2-(2-chloro-5-fluoro-4-(N-(thiazol-4-yl)sulfamoyl) phenoxy)-5-fluorophenyl)propyl)amino)propanoic acid,
3-((3-(5-chloro-2-(2-chloro-5-fluoro-4-(N-(thiazol-4-yl)sulfamoyl)phenoxy)phenyl)propyl)amino)propanamide,
2-(N-(3-(5-chloro-2-(2-chloro-5-fluoro-4-(N-(thiazol-4-yl) sulfamoyl)phenoxy)phenyl)propyl)acetamido)acetic acid,
2-(1-(3-(2-(4-(N-(1,2,4-thiadiazol-5-yl)sulfamoyl)-2-chloro-5-fluorophenoxy)-5-chlorophenyl)propyl)piperidin-4-yl)acetic acid,
3-((3-(5-chloro-2-(2-chloro-5-fluoro-4-(N-(thiazol-2-yl)sulfamoyl)phenoxy)phenyl)propyl)amino)propanoic acid,
2-((3-(5-chloro-2-(2-chloro-5-fluoro-4-(N-(thiazol-4-yl)sulfamoyl)phenoxy)phenyl)propyl)amino)-N-methylacetamide,
5-chloro-4-(4-chloro-2-(3-((2-(methylsulfonyl)ethyl)amino) propyl)phenoxy)-2-fluoro-N-(thiazol-4-yl)benzenesulfonamide,
1-(3-(2-(4-(N-(1,2,4-thiadiazol-5-yl)sulfamoyl)-2-chloro-5-fluorophenoxy)-5-chlorophenyl)propyl)piperidine-4-carboxylic acid, or
5-chloro-4-(4-chloro-2-(4,5,6,7-tetrahydropyrazolo[1,5-a] pyrimidin-3-yl)phenoxy)-2-fluoro-N-(thiazol-4-yl)benzenesulfonamide; or a pharmaceutically acceptable salt, or a stereoisomeric or tautomeric form thereof.

In a particular embodiment, the compounds of Formula (I) are those wherein the compound is 2-(4-(2-(4-(N-(1,2,4-thiadiazol-5-yl)sulfamoyl)-2-chloro-5-fluorophenoxy)-5-chlorophenyl)picolinamido)acetic acid,
3-(4-(2-(4-(N-(1,2,4-thiadiazol-5-yl)sulfamoyl)-2-chloro-5-fluorophenoxy)-5-chlorophenyl)picolinamido)propanoic acid,
2-(4-(2-(4-(N-(1,2,4-thiadiazol-5-yl)sulfamoyl)-2-chloro-5-fluorophenoxy)-5-chlorophenyl)picolinamido)propanoic acid, or
3-((3-(2-(4-(N-(1,2,4-thiadiazol-5-yl)sulfamoyl)-2-chloro-5-fluorophenoxy)-5-chlorophenyl)propyl)amino)propanoic acid; or a pharmaceutically acceptable salt, or a stereoisomeric or tautomeric form thereof.

Provided herein are methods for treating neuropathic pain comprising administering to a subject in need thereof, a therapeutically effective amount of a compound of Formula (I), or a pharmaceutically acceptable salt, solvate or tautomeric form thereof.

Provided herein are methods for treating pain comprising use of a compound of Formula (I), as a voltage-gated sodium channel inhibitor. In a particular embodiment the methods are those, wherein the pain is neuropathic, nociceptive or inflammatory pain. In a particular embodiment the methods are those, wherein the voltage-gated sodium channel is NaV1.7.

Provided herein are pharmaceutical compositions comprising a compound of Formula (I) and a pharmaceutically acceptable carrier. In a particular embodiment the pharmaceutical compositions are those, wherein the composition is suitable for topical, oral, subcutaneous, or intravenous administration.

Provided herein are methods for prevention or treatment of pain in a subject, wherein the method comprises administering to the subject in need of such prevention or treatment a therapeutically effective amount of a compound of Formula (I). In a particular embodiment the methods are those, wherein the therapeutically effective amount is effective to alleviate pain in a subject, wherein the compound of Formula (I) shows a reduction in pain response in the Formalin Assay (in phase 1 or phase 2, or both) (see Section 5.1.2) at a dose between 0.1 mg/kg and 1,000 mg/kg, at a dose between 0.5 mg/kg and 100 mg/kg, at a dose between 1 mg/kg to 50 mg/kg, or at a dose of 5 mg/kg. In certain embodiments, a compound of Formula (I) provided herein shows a reduction in pain response in the Formalin Assay (in phase 1 or phase 2, or both) by at least 10%, 20%, 30%, 40%, 50%, 60%, 70%, 80%, 90%, 95%, 98%, 99%, or 100%, or by ranges between any of the recited percentages (e.g., 10-20%, 10-30%, 10-40%, 20-30%, or 20-40%) relative to a vehicle control. In a particular embodiment the methods are those, wherein the pain is nociceptive pain, such as that resulting from physical trauma (e.g., a cut or contusion of the skin; or a chemical or thermal burn), osteoarthritis, rheumatoid arthritis or tendonitis; myofascial pain; neuropathic pain, such as that associated with stroke, diabetic neuropathy, luetic neuropathy, postherpetic neuralgia, trigeminal neuralgia, fibromyalgia, or painful neuropathy induced iatrogenically by drugs; or mixed pain (i.e., pain with both nociceptive and neuropathic components); visceral pain; headache pain (e.g., migraine headache pain); CRPS; CRPS type I; CRPS type II; RSD; reflex neurovascular dystrophy; reflex dystrophy; sympathetically maintained pain syndrome; causalgia; Sudeck atrophy of bone; algoneurodystrophy; shoulder hand syndrome; post-traumatic dystrophy; autonomic dysfunction; autoimmune-related pain; inflammation-related pain; cancer-related pain; phantom limb pain; chronic fatigue syndrome; post-operative pain; spinal cord injury pain; central post-stroke pain; radiculopathy; sensitivity to temperature, light touch or color change to the skin (allodynia); pain from hyperthermic or hypothermic conditions; and other painful conditions (e.g., diabetic neuropathy, luetic neuropathy, postherpetic neuralgia, trigeminal neuralgia); chronic pain; or acute pain.

Provided herein are methods modulating the activity of a voltage-gated sodium channel, wherein the method comprises contacting a cell that expresses the voltage-gated sodium channel with a compound of Formula (I). In a particular embodiments the methods are those, wherein the voltage-gated sodium channel is NaV1.7. In a particular embodiments the methods are those, wherein the method results in inhibition of the voltage-gated sodium channel.

4 DETAILED DESCRIPTION

4.1 Definitions

A "Compound" or "Compounds" as used herein comprise a compound of Formula (I), a compound of Formula (Ia), a compound of Formula (Ib), a compound of Formula (Ic), a compound of Formula (Id), a compound listed in Table 1, or a compound listed in Table 2.

A "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the Compounds inhibitors include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Others are well known in the art, see for example, *Remington's Pharmaceutical Sciences,* 18th eds., Mack Publishing, Easton Pa. (1990) or *Remington: The Science and Practice of Pharmacy,* 19th eds., Mack Publishing, Easton Pa. (1995).

A "stereoisomer" or "stereoisomeric form" refers to one stereoisomer of a Compound that is substantially free of other stereoisomers of that Compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The Compounds can have chiral centers and can occur as racemates, individual enantiomers or diastereomers, and mixtures thereof. All such isomeric forms are included within the embodiments disclosed herein, including mixtures thereof. The use of stereomerically pure forms of such Compounds, as well as the use of mixtures of those forms, are encompassed by the embodiments disclosed herein. For example, mixtures comprising equal or unequal amounts of the enantiomers of a particular Compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley Interscience, New York, 1981); Wilen, S. H., et al., *Tetrahedron* 33:2725 (1977); Eliel, E. L., *Stereochemistry of Carbon Compounds* (McGraw Hill, N Y, 1962); and Wilen, S. H., Tables of *Resolving Agents and Optical Resolutions* p. 268 (E. L. Eliel, Ed., Univ. of Notre Dame Press, Notre Dame, Ind., 1972).

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

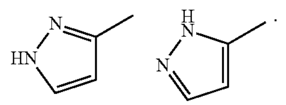

As readily understood by one skilled in the art, a wide variety of functional groups and other structures may exhibit tautomerism and all tautomers of the Compounds provided herein are within the scope of the present disclosure.

An "aryl" group is an aromatic carbocyclic group of from 6 to 14 carbon atoms having a single ring (e.g., phenyl) or multiple condensed rings (e.g., naphthyl or anthryl). In some embodiments, aryl groups contain 6-14 carbons, and in others from 6 to 12 or even 6 to 10 carbon atoms in the ring portions of the groups. Particular aryls include, but are not limited to, phenyl, naphthyl and the like.

A "heteroaryl" group is an aryl ring system having one to four heteroatoms as ring atoms in a heteroaromatic ring system, wherein the remainder of the atoms are carbon atoms. In some embodiments, heteroaryl groups contain 5 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Examples include, but are not limited to, groups such as pyrrolyl, pyrazolyl, imidazolyl, triazolyl, tetrazolyl, oxazolyl, isoxazolyl, thiazolyl, isothiazolyl, thiadiazolyl (e.g., 1,2,4-thiadiazolyl), pyrrolyl, pyridyl, pyridazinyl, pyrimidinyl, pyrazinyl, thiophenyl, benzothiophenyl, furanyl, benzofuranyl, indolyl, azaindolyl (for example, pyrrolopyridyl or 1H-pyrrolo[2,3-b]pyridyl), indazolyl, benzimidazolyl (for example, 1H-benzo[d]imidazolyl), imidazopyridyl, pyrazolopyridyl, triazolopyridyl, benzotriazolyl, benzoxazolyl, benzothiazolyl, benzothiadiazolyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups.

A "partially unsaturated or aromatic heterocycle" is a partially unsaturated or aromatic ring system having one to four heteroatoms as ring atoms in a heteroaromatic ring system, wherein the remainder of the atoms are carbon atoms. If the "partially unsaturated or aromatic heterocycle" is an aromatic heterocycle, then the aromatic heterocycle is a "heteroaryl" as defined above. In one embodiment the partially unsaturated or aromatic heterocycle is a partially unsaturated or aromatic 5- or 6-membered heterocycle. Examples of partially unsaturated heterocycles include, but are not limited to, groups such as 2,5-dihydro-1H-pyrrolyl, 2,5-dihydrofuranyl, 2,5-dihydrothiophenyl, 4,5-dihydrooxazolyl, 4,5-dihydrothiazolyl, 4,5-dihydro-1H-imidazolyl, 4,5-dihydro-1H-1,2,3-triazolyl, 1,2,5,6-tetrahydropyridinyl, and 1,4,5,6-tetrahydropyrimidinyl groups.

A "heterocycloalkyl" group is a non-aromatic cycloalkyl in which one to four of the ring carbon atoms are independently replaced with a heteroatom from the group consisting of O, S and N. Examples of a heterocycloalkyl group include, but are not limited to, morpholinyl, pyrrolidinyl, piperazinyl, (1,4)-dioxanyl, and (1,3)-dioxolanyl. Heterocycloalkyls can also be bonded at any ring atom (i.e., at any carbon atom or heteroatom of the heterocyclic ring). In one embodiment, the heterocycloalkyl is a 5- or 6-membered heterocycloalkyl.

An "alkyl" group is a saturated straight chain or branched non-cyclic hydrocarbon having, for example, from 1 to 12 carbon atoms, 1 to 9 carbon atoms, 1 to 6 carbon atoms, 1 to 4 carbon atoms, or 2 to 6 carbon atoms. Representative alkyl groups include -methyl, -ethyl, -n-propyl, -n-butyl, -n-pentyl and -n-hexyl; while branched alkyls include -isopropyl, -sec-butyl, -iso-butyl, -tert-butyl, -iso-pentyl, 2-methylpentyl, 3-methylpentyl, 4-methylpentyl, 2,3-dimethylbutyl and the like.

A "cycloalkyl" group is a saturated cyclic alkyl group of from 3 to 12 carbon atoms having a single cyclic ring or multiple condensed or bridged rings. In some embodiments, the cycloalkyl group has 4 to 12 ring members, whereas in other embodiments the number of ring carbon atoms ranges, for example, from 3 to 5, 3 to 6, or 3 to 7. Such cycloalkyl groups include, by way of example, single ring structures such as cyclopropyl, cyclobutyl, cyclopentyl, cyclohexyl, cycloheptyl, cyclooctyl, and the like, or multiple or bridged ring structures such as adamantyl and the like.

A "subject in need thereof" refers to a mammal (e.g., human, dog, horse, or cat) in need of treatment with any method provided herein.

4.2 Compounds

Provided herein are compounds of Formula (I),

Formula (I)

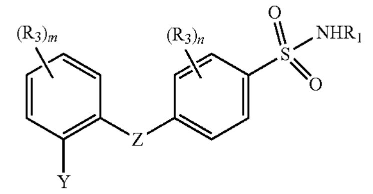

or a pharmaceutically acceptable salt, or a stereoisomeric or tautomeric form thereof, wherein:

Z is —O— or —S—;

Y is —X—C(═O)$NR_4R_5$, —$(CH_2)_3$—$NR_9R_{10}$, or 4,5,6,7-tetrahydropyrazolo[1,5-a]pyrimidine-(2-yl or 3-yl);

X is ($C_6$-$C_{10}$)aryl or 5- or 6-membered heteroaryl;

$R_1$ is a partially unsaturated or aromatic 5- or 6-membered heterocycle;

$R_2$ is independently at each occurrence —F, —Cl, —Br, —$CH_3$ or —CN;

$R_3$ is independently at each occurrence —H, —F, —Cl, —Br, —$CF_3$, —$OCF_3$, —CN, ($C_1$-$C_{12}$)alkyl, or ($C_1$-$C_{12}$) alkoxy;

$R_4$ and $R_5$ are each independently H, ($C_1$-$C_9$)alkyl, ($C_4$-$C_{12}$) cycloalkyl, or $R_4$ and $R_5$ together form a 5- to 7-membered heterocycloalkyl ring; with the proviso that:

$R_4$ and $R_5$ are not both H; and at least one of $R_4$ and $R_5$ independently or said heterocycloalkyl ring formed by $R_4$ and $R_5$ together is substituted with 1 or 2 substituents selected from the group consisting of —$CO_2H$, —$CO_2R_6$, —CN, —OH, —$CONR_7R_8$, and —$NR_7R_8$; wherein:

$R_6$ is ($C_1$-$C_{12}$)alkyl;

$R_7$ and $R_8$ are each independently H, ($C_1$-$C_{12}$)alkyl, or $R_7$ and $R_8$ together form a 4- to 7-membered heterocycloalkyl ring;

$R_9$ is ($C_1$-$C_6$)alkyl, ($C_3$-$C_8$)cycloalkyl, pyrazolyl or pyridinyl; wherein $R_9$ is optionally further substituted with 1 or 2 substituents selected from the group consisting of —COOH, —$COOR_{11}$, —$CONR_{11}R_{12}$, —$SO_2R_{11}$, —$SO_2NR_{11}R_{12}$, —OH, —CN, —$OR_{11}$, and —$NR_{11}R_{12}$; wherein $R_{11}$ and $R_{12}$ may form a 6 membered heterocycloalkyl ring $R_{10}$ is $R_{11}$, —$COR_{11}$, —$COOR_{11}$, —$SO_2R_{11}$, 5-methyl-2-oxo-1,3-dioxol-4-yl,

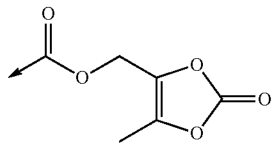

$-COO-CH(CH_3)OCOCH(CH_3)_2$; or $R_9$ and $R_{10}$ together form a piperazinone or a 4- to 8-membered heterocycloalkyl ring, wherein said heterocycloalkyl ring is substituted with 1 or 2 substituents selected from the group consisting of —COOH, $-COOR_{11}$, $-CH_2-COOR_{11}$, —OH, $-NH_2$, —CN, and $(C_1-C_8)$alkoxy;

$R_{11}$ and $R_{12}$ are independently H or $(C_1-C_6)$alkyl, optionally substituted with 4- to 8-membered heterocycloalkyl ring; and m and n are each independently 1, 2, 3, or 4.

In a certain embodiment, the compounds of Formula (I) are those wherein Y is $-(CH_2)_3-NR_9R_{10}$.

In a particular embodiment, the compounds of Formula (I) are those wherein $R_1$ is an aromatic 5- or 6-membered heterocycle, with 1-3 heteroatoms independently selected from the group consisting of N, O, and S.

In a particular embodiment, the compounds of Formula (I) are those wherein $R_1$ is pyridyl or pyrimidinyl.

In a particular embodiment, the compounds of Formula (I) are those wherein $R_1$ is an aromatic 5-membered heterocycle with 1 or 2 nitrogen atoms and optionally 1 or 2 sulphur atoms. In a particular embodiment, the compounds of Formula (I) are those wherein $R_1$ is thiazolyl, isothiazolyl, or thiadiazolyl. In a particular embodiment, the compounds of Formula (I) are those wherein $R_1$ is thiazolyl. In a particular embodiment, the compounds of Formula (I) are those wherein $R_1$ is 1,2,4-thiadiazol-5-yl.

In a particular embodiment, the compounds of Formula (I) are those wherein $R_2$ is independently at each occurrence —F or —Cl.

In a particular embodiment, the compounds of Formula (I) are those wherein n is 1, 2, or 3. In a particular embodiment, the compounds of Formula (I) are those wherein n is 2.

In a particular embodiment, the compounds of Formula (I) are those wherein Z is —O—.

In a particular embodiment, the compounds of Formula (I) are those wherein $R_3$ is independently at each occurrence —H, —F, —Cl, or —Br. In a particular embodiment, the compounds of Formula (I) are those wherein $R_3$ is —H or —Cl. In a particular embodiment, the compounds of Formula (I) are those wherein $R_3$ is —Cl.

In a particular embodiment, the compounds of Formula (I) are those wherein m is 1, 2, or 3. In a particular embodiment, the compounds of Formula (I) are those wherein m is 1.

In a particular embodiment, the compounds of Formula (I) are those wherein $R_9$ is $(C_1-C_6)$alkyl; wherein $R_9$ is optionally further substituted with 1 or 2 substituents selected from the group consisting of —COOH, —COOMe, $-CONH_2$, and $-NH_2$. In a particular embodiment, the compounds of Formula (I) are those wherein $R_9$ is methyl or ethyl. In a particular embodiment, the compounds of Formula (I) are those wherein $R_9$ is further substituted with —COOH.

In a particular embodiment, the compounds of Formula (I) are those wherein $R_{10}$ is —H, —COMe, —COOEt. In a particular embodiment, the compounds of Formula (I) are those wherein $R_{10}$ is —H or —COMe. In a particular embodiment, the compounds of Formula (I) are those wherein $R_{10}$ is —H.

In a particular embodiment, the compounds of Formula (I) are those wherein $R_9$ and $R_{10}$ together form a 4 to 8 membered heterocycloalkyl ring, wherein said heterocycloalkyl ring is substituted with 1 or 2 groups selected from the group consisting of —COOH, —COOMe, —COOEt, $-CH_2-COOH$, and $-NH_2$. In a particular embodiment, the compounds of Formula (I) are those wherein $R_9$ and $R_{10}$ together form a 4 to 8 membered heterocycloalkyl ring, wherein said heterocycloalkyl ring is substituted with 1 or 2 groups selected from the group consisting of —COOH, $-CH_2-COOH$, and $-NH_2$.

In a particular embodiment, the compounds of Formula (I) are those wherein $R_9$ and $R_{10}$ together form a piperidine substituted with 1 or 2 groups selected from the group consisting of —COOH, —COOMe, —COOEt, $-CH_2-COOH$, $-CH_2-COOMe$, $-CH_2-COOEt$, and $-NH_2$. In a particular embodiment, the compounds of Formula (I) are those wherein $R_9$ and $R_{10}$ together form a piperidine substituted with 1 or 2 groups selected from the group consisting of —COOH, $-CH_2-COOH$, and $-NH_2$.

In a certain embodiment, the compounds of Formula (I) are those wherein Y is $-X-C(=O)NR_4R_5$.

In a particular embodiment, the compounds of Formula (I) are those wherein $R_1$ is an aromatic 5- or 6-membered heterocycle, with 1-3 heteroatoms independently selected from the group consisting of N, O, and S.

In a particular embodiment, the compounds of Formula (I) are those wherein $R_1$ is pyridyl or pyrimidinyl.

In a particular embodiment, the compounds of Formula (I) are those wherein $R_1$ is an aromatic 5-membered heterocycle with 1 or 2 nitrogen atoms and optionally 1 or 2 sulphur atoms. In a particular embodiment, the compounds of Formula (I) are those wherein $R_1$ is thiazolyl, isothiazolyl, or thiadiazolyl. In a particular embodiment, the compounds of Formula (I) are those wherein $R_1$ is thiazolyl. In a particular embodiment, the compounds of Formula (I) are those wherein $R_1$ is 1,2,4-thiadiazol-5-yl.

In a particular embodiment, the compounds of Formula (I) are those wherein $R_2$ is independently at each occurrence —F or —Cl.

In a particular embodiment, the compounds of Formula (I) are those wherein n is 1, 2, or 3. In a particular embodiment, the compounds of Formula (I) are those wherein n is 2.

In a particular embodiment, the compounds of Formula (I) are those wherein Z is —O—.

In a particular embodiment, the compounds of Formula (I) are those wherein $R_3$ is independently at each occurrence —F, —Cl, or —Br. In a particular embodiment, the compounds of Formula (I) are those wherein $R_3$ is —H or —Cl. In a particular embodiment, the compounds of Formula (I) are those wherein $R_3$ is —Cl.

In a particular embodiment, the compounds of Formula (I) are those wherein m is 1, 2, or 3. In a particular embodiment, the compounds of Formula (I) are those wherein m is 1.

In a particular embodiment, the compounds of Formula (I) are those wherein X is 5- or 6-membered heteroaryl. In a particular embodiment, the compounds of Formula (I) are those wherein X is pyridyl or pyrimidinyl. In a particular embodiment, the compounds of Formula (I) are those wherein X is pyridyl.

In a particular embodiment, the compounds of Formula (I) are those wherein $R_4$ is H and $R_5$ is $(C_1-C_9)$alkyl.

In a particular embodiment, the compounds of Formula (I) are those wherein $R_5$ is methyl or ethyl, substituted with 1 or 2 substituents selected from the group consisting of $-CO_2H$, $-CO_2R_6$, and $-CONR_7R_8$.

In a particular embodiment, the compounds of Formula (I) are those wherein $R_6$ is $(C_1-C_6)$alkyl.

In a particular embodiment, the compounds of Formula (I) are those wherein $R_5$ is methyl or ethyl, substituted with —$CO_2H$.

In a certain embodiment, the compounds of Formula (I) are those wherein Y is 4,5,6,7-tetrahydropyrazolo[1,5-a] pyrimidine-(2-yl or 3-yl). In a particular embodiment, the compounds of Formula (I) are those wherein Y is 4,5,6,7-tetrahydropyrazolo[1,5-a]pyrimidine-3-yl.

In a particular embodiment, the compounds of Formula (I) are those wherein $R_1$ is an aromatic 5- or 6-membered heterocycle, with 1-3 heteroatoms independently selected from the group consisting of N, O, and S.

In a particular embodiment, the compounds of Formula (I) are those wherein $R_1$ is pyridyl or pyrimidinyl.

In a particular embodiment, the compounds of Formula (I) are those wherein $R_1$ is an aromatic 5-membered heterocycle with 1 or 2 nitrogen atoms and optionally 1 or 2 sulphur atoms. In a particular embodiment, the compounds of Formula (I) are those wherein $R_1$ is thiazolyl, isothiazolyl, or thiadiazolyl. In a particular embodiment, the compounds of Formula (I) are those wherein $R_1$ is thiazolyl. In a particular embodiment, the compounds of Formula (I) are those wherein $R_1$ is 1,2,4-thiadiazol-5-yl.

In a particular embodiment, the compounds of Formula (I) are those wherein $R_2$ is independently at each occurrence —F or —Cl.

In a particular embodiment, the compounds of Formula (I) are those wherein n is 1, 2, or 3. In a particular embodiment, the compounds of Formula (I) are those wherein n is 2.

In a particular embodiment, the compounds of Formula (I) are those wherein Z is —O—.

In a particular embodiment, the compounds of Formula (I) are those wherein $R_3$ is independently at each occurrence —F, —Cl, or —Br. In a particular embodiment, the compounds of Formula (I) are those wherein $R_3$ is —H or —Cl. In a particular embodiment, the compounds of Formula (I) are those wherein $R_3$ is —Cl.

In a particular embodiment, the compounds of Formula (I) are those wherein m is 1, 2, or 3. In a particular embodiment, the compounds of Formula (I) are those wherein m is 1.

In a certain embodiment, the compounds of Formula (I) are those wherein the compound is selected from the group consisting of the compounds in Table 1 or a pharmaceutically acceptable salt, or a stereoisomeric or tautomeric form thereof.

TABLE 1

| Example | Compound Structure | Chemical name* |
|---|---|---|
| 1 | 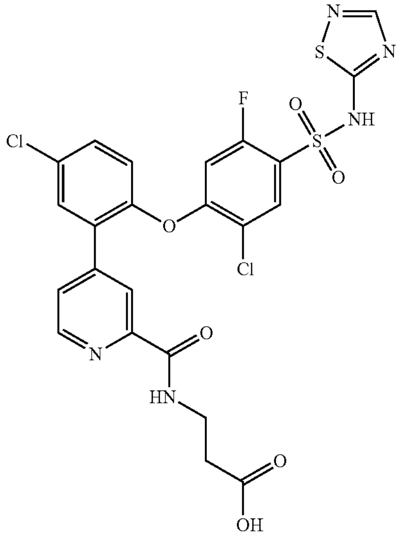 [SMILES: O=C(O)CCNC(=O)c1cc(-c2cc(Cl)ccc2Oc2cc(F)c(S(=O)(=O)Nc3ncns3)cc2Cl)ccn1] | 3-(4-(2-(4-(N-(1,2,4-thiadiazol-5-yl)sulfamoyl)-2-chloro-5-fluorophenoxy)-5-chlorophenyl)picolinamido) propanoic acid |
| 2 | 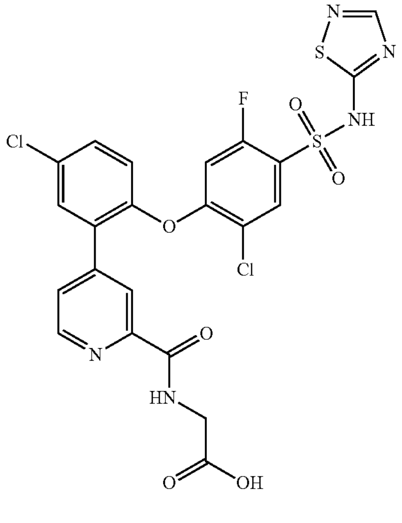 [SMILES: O=C(O)CNC(=O)c1cc(-c2cc(Cl)ccc2Oc2cc(F)c(S(=O)(=O)Nc3ncns3)cc2Cl)ccn1] | 2-(4-(2-(4-(N-(1,2,4-thiadiazol-5-yl)sulfamoyl)-2-chloro-5-fluorophenoxy)-5-chlorophenyl) picolinamido)acetic acid |

TABLE 1-continued
| Example | Compound Structure | Chemical name* |
|---|---|---|
| 3 | 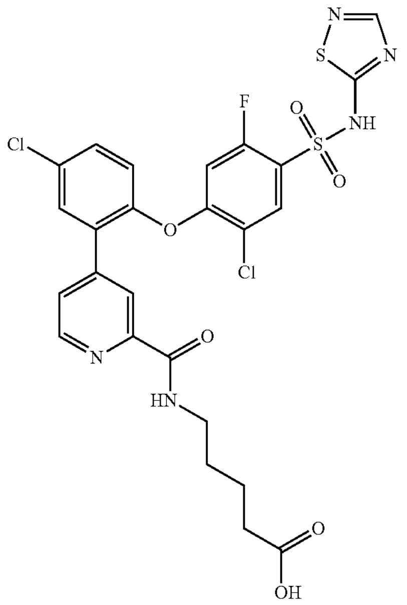 [SMILES: O=C(O)CCCCNC(=O)c1cc(-c2cc(Cl)ccc2Oc2cc(F)c(S(=O)(=O)Nc3ncns3)cc2Cl)ccn1] | 5-(4-(2-(4-(N-(1,2,4-thiadiazol-5-yl)sulfamoyl)-2-chloro-5-fluorophenoxy)-5-chlorophenyl)picolinamido) pentanoic acid |
| 4 | 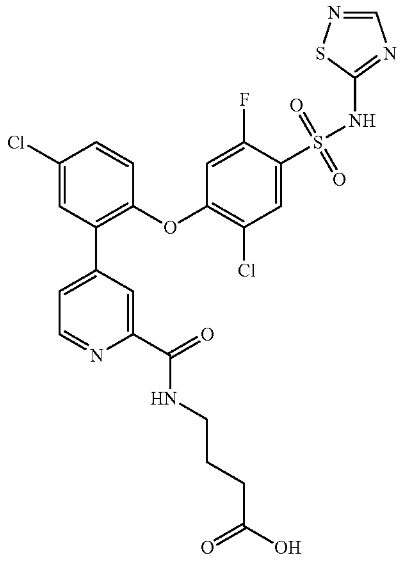 [SMILES: O=C(O)CCCNC(=O)c1cc(-c2cc(Cl)ccc2Oc2cc(F)c(S(=O)(=O)Nc3ncns3)cc2Cl)ccn1] | 4-(4-(2-(4-(N-(1,2,4-thiadiazol-5-yl)sulfamoyl)-2-chloro-5-fluorophenoxy)-5-chlorophenyl) picolinamido)butanoic acid |
| 5 | 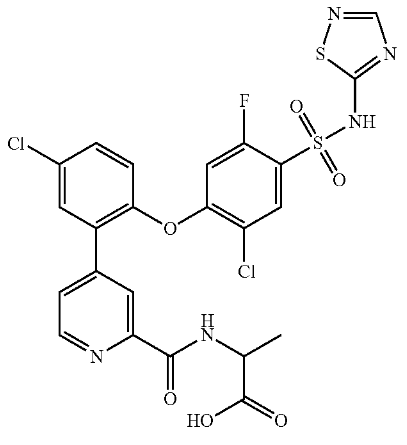 [SMILES: CC(NC(=O)c1cc(-c2cc(Cl)ccc2Oc2cc(F)c(S(=O)(=O)Nc3ncns3)cc2Cl)ccn1)C(=O)O] | 2-(4-(2-(4-(N-(1,2,4-thiadiazol-5-yl)sulfamoyl)-2-chloro-5-fluorophenoxy)-5-chlorophenyl)picolinamido) propanoic acid |

TABLE 1-continued
| Example | Compound Structure | Chemical name* |
|---|---|---|
| 6 | 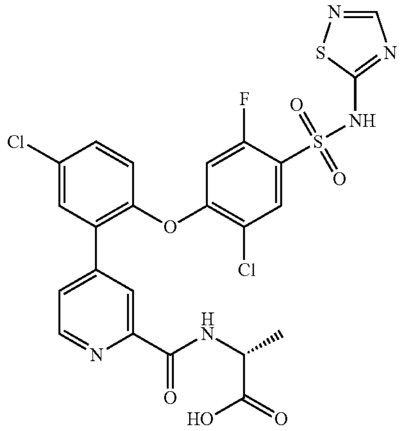 [SMILES: C[C@@H](NC(=O)c1cc(-c2cc(Cl)ccc2Oc2cc(F)c(S(=O)(=O)Nc3ncns3)cc2Cl)ccn1)C(=O)O] | (R)-2-(4-(2-(4-(N-(1,2,4-thiadiazol-5-yl)sulfamoyl)-2-chloro-5-fluorophenoxy)-5-chlorophenyl)picolinamido) propanoic acid |
| 7 | 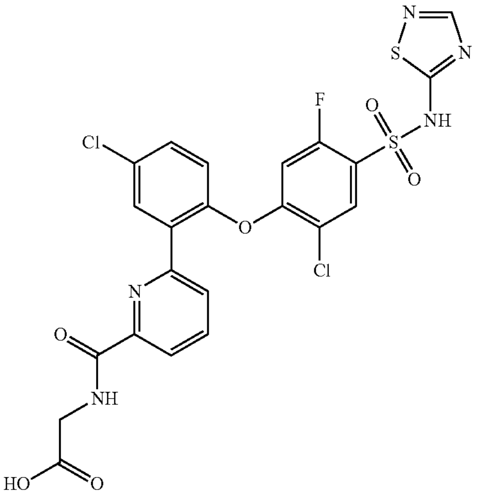 [SMILES: O=C(O)CNC(=O)c1cccc(-c2cc(Cl)ccc2Oc2cc(F)c(S(=O)(=O)Nc3ncns3)cc2Cl)n1] | 2-(6-(2-(4-(N-(1,2,4-thiadiazol-5-yl)sulfamoyl)-2-chloro-5-fluorophenoxy)-5-chlorophenyl) picolinamido)acetic acid |
| 8 | 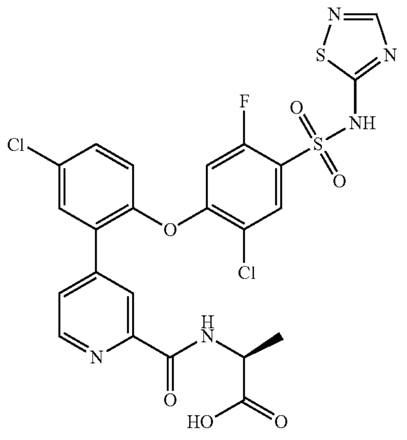 [SMILES: C[C@H](NC(=O)c1cc(-c2cc(Cl)ccc2Oc2cc(F)c(S(=O)(=O)Nc3ncns3)cc2Cl)ccn1)C(=O)O] | (S)-2-(4-(2-(4-(N-(1,2,4-thiadiazol-5-yl)sulfamoyl)-2-chloro-5-fluorophenoxy)-5-chlorophenyl)picolinamido) propanoic acid |

TABLE 1-continued
| Example | Compound Structure | Chemical name* |
|---|---|---|
| 9 | 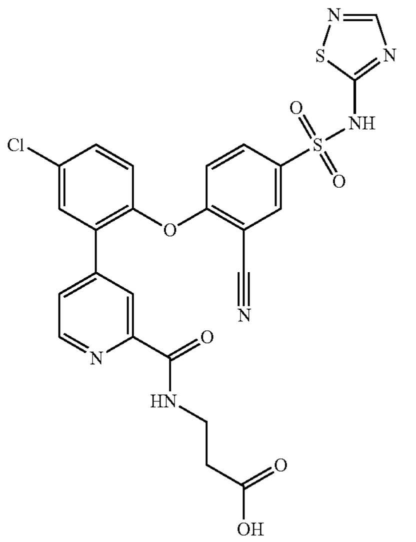 [SMILES: N#Cc1cc(S(=O)(=O)Nc2ncns2)ccc1Oc1ccc(Cl)cc1-c1ccnc(C(=O)NCCC(=O)O)c1] | 3-(4-(2-(4-(N-(1,2,4-thiadiazol-5-yl)sulfamoyl)-2-cyanophenoxy)-5-chlorophenyl) picolinamido)propanoic acid |
| 10 | 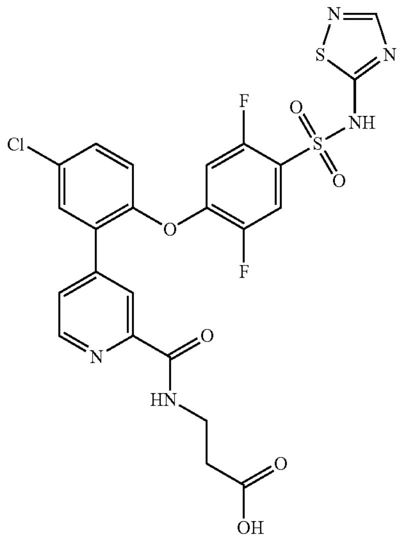 [SMILES: O=C(O)CCNC(=O)c1cc(-c2cc(Cl)ccc2Oc2cc(F)c(S(=O)(=O)Nc3ncns3)cc2F)ccn1] | 3-(4-(2-(4-(N-(1,2,4-thiadiazol-5-yl)sulfamoyl)-2,5-difluorophenoxy)-5-chlorophenyl)picolinamido) propanoic acid |
| 11 | 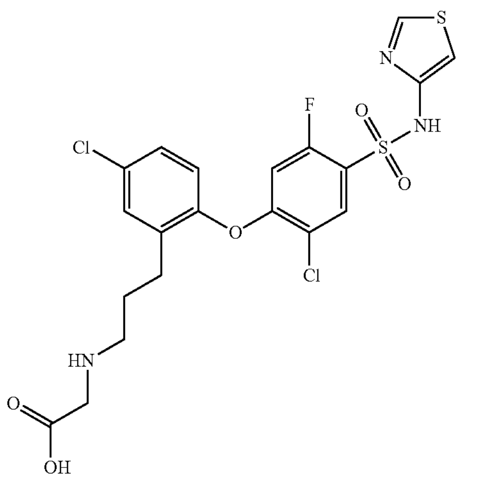 [SMILES: O=C(O)CNCCCc1cc(Cl)ccc1Oc1cc(F)c(S(=O)(=O)Nc2cscn2)cc1Cl] | 2-((3-(5-chloro-2-(2-chloro-5-fluoro-4-(N-(thiazol-4-yl)sulfamoyl)phenoxy)phenyl) propyl)amino)acetic acid |

TABLE 1-continued
| Example | Compound Structure | Chemical name* |
|---|---|---|
| 12 | 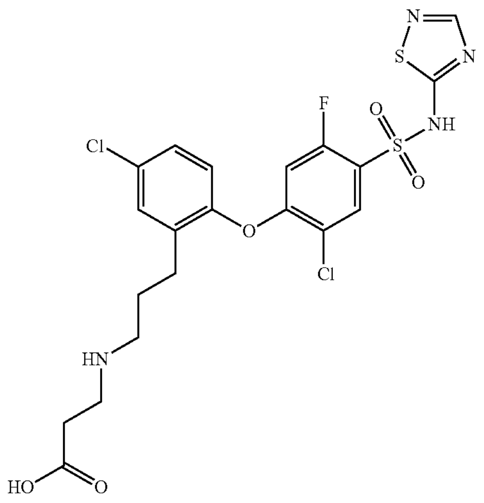 [SMILES: O=C(O)CCNCCCc1cc(Cl)ccc1Oc1cc(F)c(S(=O)(=O)Nc2ncns2)cc1Cl] | 3-((3-(2-(4-(N-(1,2,4-thiadiazol-5-yl)sulfamoyl)-2-chloro-5-fluorophenoxy)-5-chlorophenyl)propyl)amino) propanoic acid |
| 13 | 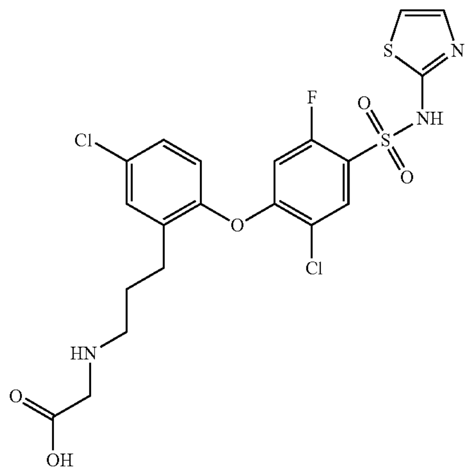 [SMILES: O=C(O)CNCCCc1cc(Cl)ccc1Oc1cc(F)c(S(=O)(=O)Nc2nccs2)cc1Cl] | 2-((3-(5-chloro-2-(2-chloro-5-fluoro-4-(N-(thiazol-2-yl)sulfamoyl)phenoxy)phenyl) propyl)amino)acetic acid |
| 14 | 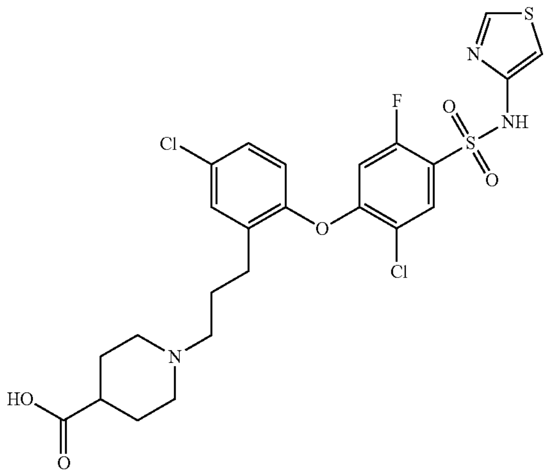 [SMILES: O=C(O)C1CCN(CCCc2cc(Cl)ccc2Oc2cc(F)c(S(=O)(=O)Nc3cscn3)cc2Cl)CC1] | 1-(3-(5-chloro-2-(2-chloro-5-fluoro-4-(N-(thiazol-4-yl)sulfamoyl)phenoxy)phenyl) propyl)piperidine-4-carboxylic acid |

TABLE 1-continued
| Example | Compound Structure | Chemical name* |
|---|---|---|
| 15 | 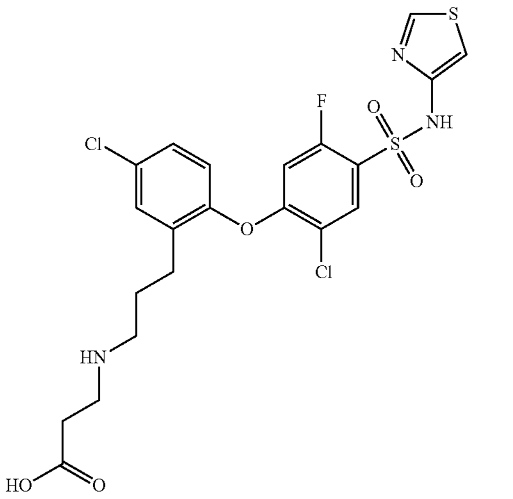 [SMILES: O=C(O)CCNCCCc1cc(Cl)ccc1Oc1cc(F)c(S(=O)(=O)Nc2cscn2)cc1Cl] | 3-((3-(5-chloro-2-(2-chloro-5-fluoro-4-(N-(thiazol-4-yl)sulfamoyl)phenoxy)phenyl)propyl)amino)propanoic acid |
| 16 | 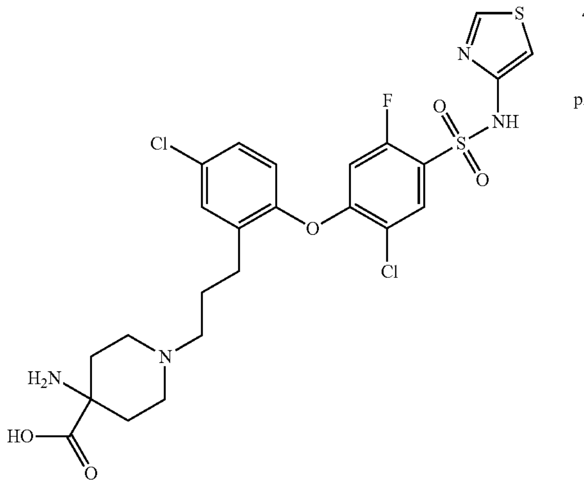 | 4-amino-1-(3-(5-chloro-2-(2-chloro-5-fluoro-4-(N-(thiazol-4-yl)sulfamoyl)phenoxy)phenyl)propyl)piperidine-4-carboxylic acid |
| 17 | 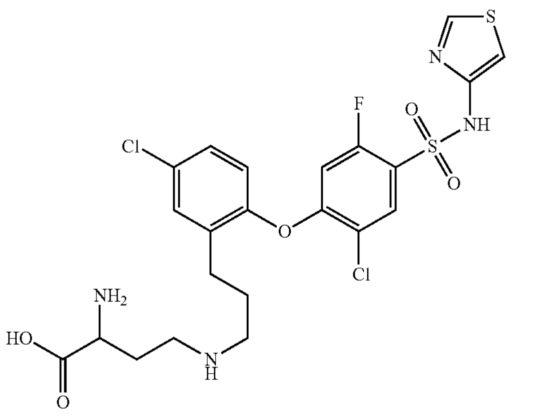 [SMILES: NC(CCNCCCc1cc(Cl)ccc1Oc1cc(F)c(S(=O)(=O)Nc2cscn2)cc1Cl)C(=O)O] | 2-amino-4-((3-(5-chloro-2-(2-chloro-5-fluoro-4-(N-(thiazol-4-yl)sulfamoyl)phenoxy)phenyl)propyl)amino)butanoic acid |

TABLE 1-continued
| Example | Compound Structure | Chemical name* |
|---|---|---|
| 18 | 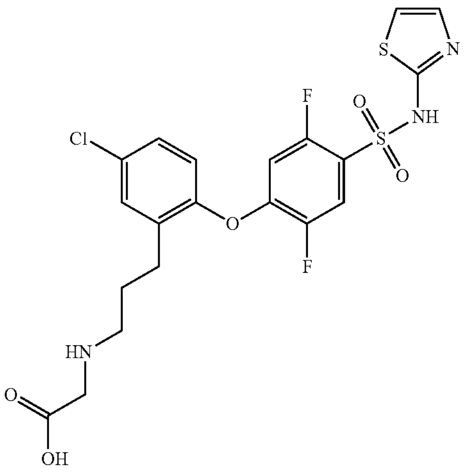 [SMILES: O=C(O)CNCCCc1cc(Cl)ccc1Oc1cc(F)c(S(=O)(=O)Nc2nccs2)cc1F] | 2-((3-(5-chloro-2-(2,5-difluoro-4-(N-(thiazol-2-yl)sulfamoyl)phenoxy)phenyl)propyl)amino)acetic acid |
| 19 | 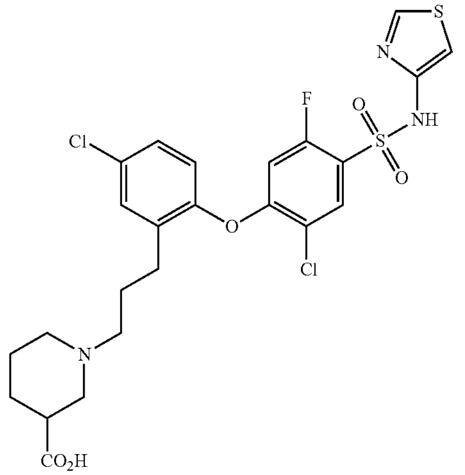 [SMILES: O=C(O)C1CCCN(CCCc2cc(Cl)ccc2Oc2cc(F)c(S(=O)(=O)Nc3cscn3)cc2Cl)C1] | 1-(3-(5-chloro-2-(2-chloro-5-fluoro-4-(N-(thiazol-4-yl)sulfamoyl)phenoxy)phenyl)propyl)piperidine-3-carboxylic acid |
| 20 | 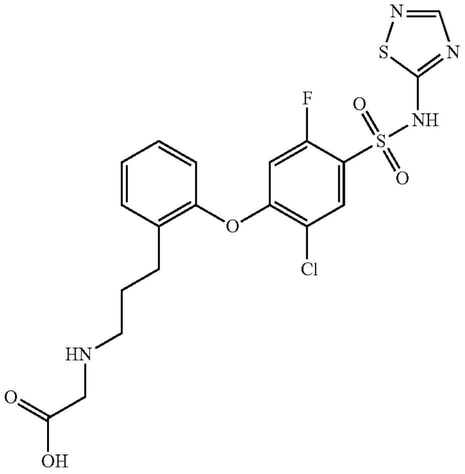 [SMILES: O=C(O)CNCCCc1ccccc1Oc1cc(F)c(S(=O)(=O)Nc2ncns2)cc1Cl] | 2-((3-(2-(4-(N-(1,2,4-thiadiazol-5-yl)sulfamoyl)-2-chloro-5-fluorophenoxy)phenyl)propyl)amino)acetic acid |

TABLE 1-continued
| Example | Compound Structure | Chemical name* |
| --- | --- | --- |
| 21 | 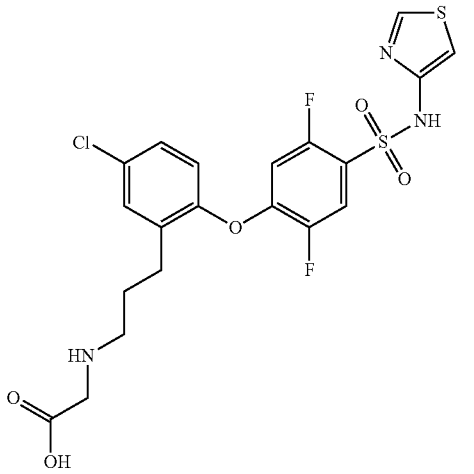 [SMILES: O=C(O)CNCCCc1cc(Cl)ccc1Oc1cc(F)c(S(=O)(=O)Nc2cscn2)cc1F] | 2-((3-(5-chloro-2-(2,5-difluoro-4-(N-(thiazol-4-yl)sulfamoyl)phenoxy)phenyl) propyl)amino)acetic acid |
| 22 | 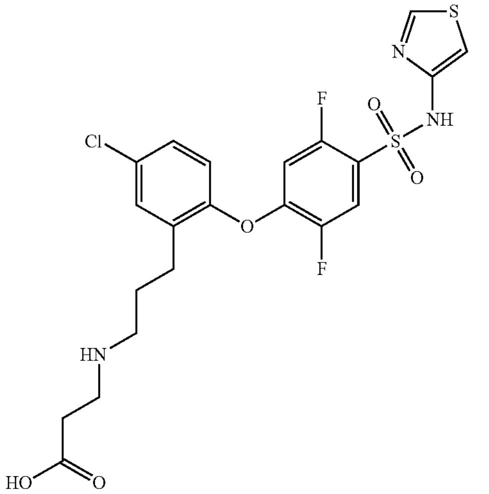 [SMILES: O=C(O)CCNCCCc1cc(Cl)ccc1Oc1cc(F)c(S(=O)(=O)Nc2cscn2)cc1F] | 3-((3-(5-chloro-2-(2,5-difluoro-4-(N-(thiazol-4-yl)sulfamoyl)phenoxy)phenyl) propyl)amino)propanoic acid |
| 23 | 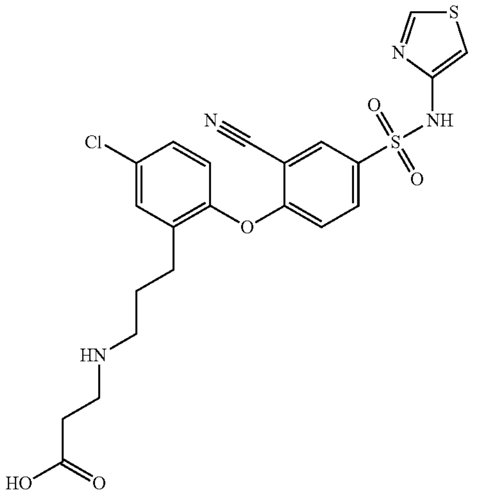 [SMILES: N#Cc1cc(S(=O)(=O)Nc2cscn2)ccc1Oc1ccc(Cl)cc1CCCNCCC(=O)O] | 3-((3-(5-chloro-2-(2-cyano-4-(N-(thiazol-4-yl)sulfamoyl)phenoxy)phenyl) propyl)amino)propanoic acid |

TABLE 1-continued
| Example | Compound Structure | Chemical name* |
| --- | --- | --- |
| 24 | 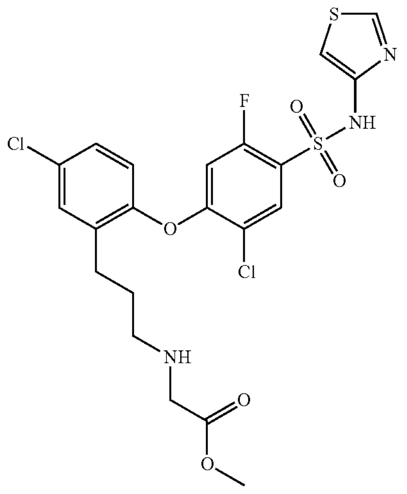 [SMILES: COC(=O)CNCCCc1cc(Cl)ccc1Oc1cc(F)c(S(=O)(=O)Nc2cscn2)cc1Cl] | methyl 2-((3-(5-chloro-2-(2-chloro-5-fluoro-4-(N-(thiazol-4-yl)sulfamoyl)phenoxy)phenyl) propyl)amino)acetate |
| 25 | 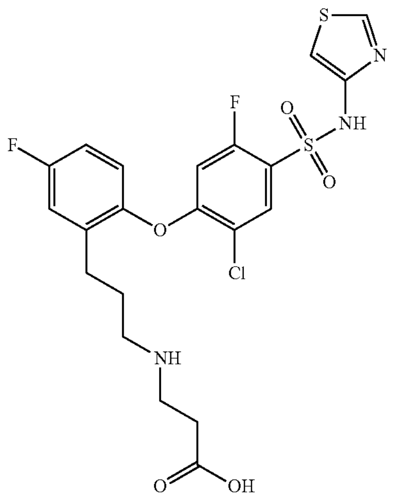 [SMILES: O=C(O)CCNCCCc1cc(F)ccc1Oc1cc(F)c(S(=O)(=O)Nc2cscn2)cc1Cl] | 3-((3-(2-(2-chloro-5-fluoro-4-(N-(thiazol-4-yl)sulfamoyl)phenoxy)-5-fluorophenyl)propyl) amino)propanoic acid |
| 26 | 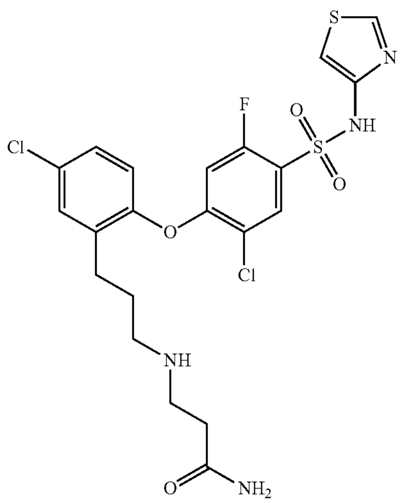 [SMILES: NC(=O)CCNCCCc1cc(Cl)ccc1Oc1cc(F)c(S(=O)(=O)Nc2cscn2)cc1Cl] | 3-((3-(5-chloro-2-(2-chloro-5-fluoro-4-(N-(thiazol-4-yl)sulfamoyl)phenoxy)phenyl) propyl)amino)propanamide |

TABLE 1-continued
| Example | Compound Structure | Chemical name* |
|---|---|---|
| 27 | 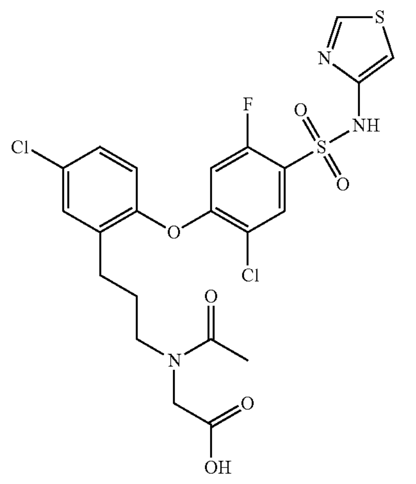 [SMILES: CC(=O)N(CCCc1cc(Cl)ccc1Oc1cc(F)c(S(=O)(=O)Nc2cscn2)cc1Cl)CC(=O)O] | 2-(N-(3-(5-chloro-2-(2-chloro-5-fluoro-4-(N-(thiazol-4-yl)sulfamoyl)phenoxy)phenyl)propyl)acetamido)acetic acid |
| 28 | 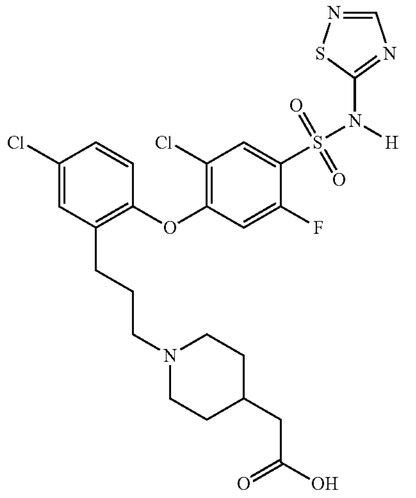 [SMILES: O=C(O)CC1CCN(CCCc2cc(Cl)ccc2Oc2cc(F)c(S(=O)(=O)Nc3ncns3)cc2Cl)CC1] | 2-(1-(3-(2-(4-(N-(1,2,4-thiadiazol-5-yl)sulfamoyl)-2-chloro-5-fluorophenyl)-5-chlorophenyl)propyl)piperidin-4-yl)acetic acid |
| 29 | 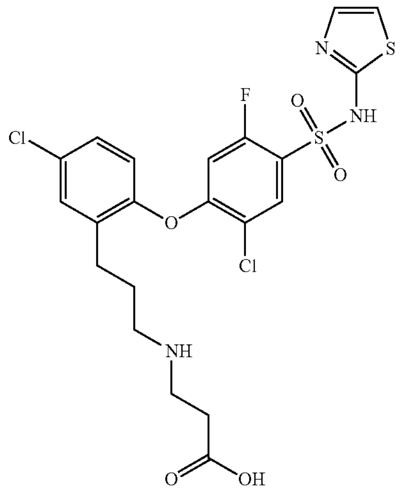 [SMILES: O=C(O)CCNCCCc1cc(Cl)ccc1Oc1cc(F)c(S(=O)(=O)Nc2nccs2)cc1Cl] | 3-((3-(5-chloro-2-(2-chloro-5-fluoro-4-(N-(thiazol-2-yl)sulfamoyl)phenoxy)phenyl)propyl)amino)propanoic acid |

TABLE 1-continued
| Example | Compound Structure | Chemical name* |
|---|---|---|
| 30 | 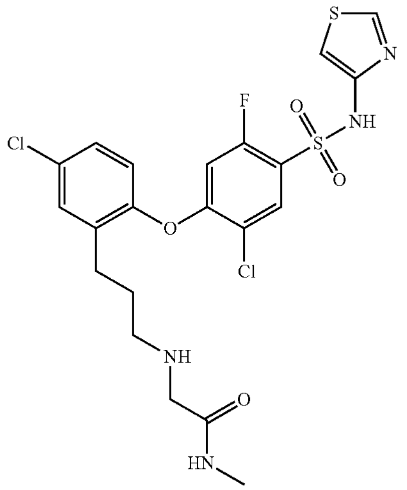 [SMILES: CNC(=O)CNCCCc1cc(Cl)ccc1Oc1cc(F)c(S(=O)(=O)Nc2cscn2)cc1Cl] | 2-((3-(5-chloro-2-(2-chloro-5-fluoro-4-(N-(thiazol-4-yl)sulfamoyl)phenoxy)phenyl) propyl)amino)-N-methylacetamide |
| 31 | 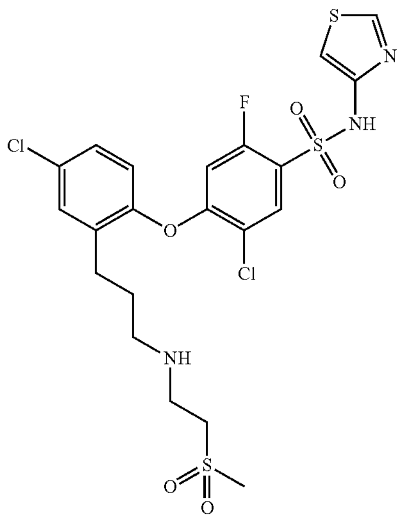 [SMILES: CS(=O)(=O)CCNCCCc1cc(Cl)ccc1Oc1cc(F)c(S(=O)(=O)Nc2cscn2)cc1Cl] | 5-chloro-4-(4-chloro-2-(3-((2-(methylsulfonyl)ethyl)amino) propyl)phenoxy)-2-fluoro-N-(thiazol-4-yl)benzenesulfonamide |
| 32 | 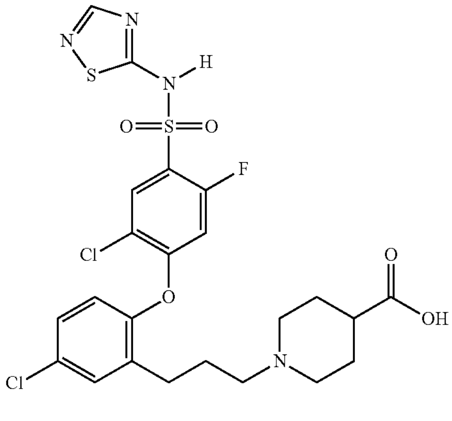 [SMILES: O=C(O)C1CCN(CCCc2cc(Cl)ccc2Oc2cc(F)c(S(=O)(=O)Nc3ncns3)cc2Cl)CC1] | 1-(3-(2-(4-(N-(1,2,4-thiadiazol-5-yl)sulfamoyl)-2-chloro-5-fluorophenoxy)-5-chlorophenyl) propyl)piperidine-4-carboxylic acid |

TABLE 1-continued

| Example | Compound Structure | Chemical name* |
|---|---|---|
| 33 | 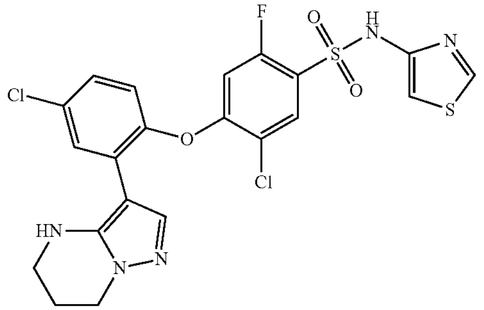 [SMILES: O=S(=O)(Nc1cscn1)c1cc(Cl)c(Oc2ccc(Cl)cc2-c2cnn3c2NCCC3)cc1F] | 5-chloro-4-(4-chloro-2-(4,5,6,7-tetrahydropyrazolo[1,5-a]pyrimidin-3-yl)phenoxy)-2-fluoro-N-(thiazol-4-yl)benzenesulfonamide |

*Chemical Names automatically generated with ChemDraw Ultra, Version 12.0.

In a certain embodiment, the compounds of Formula (I) are those wherein the compound is selected from the group consisting of the compounds in Table 2 or a pharmaceutically acceptable salt, or a stereoisomeric or tautomeric form thereof.

TABLE 2

| Prophetic Example | Compound structure | Chemical name* |
|---|---|---|
| 34 | 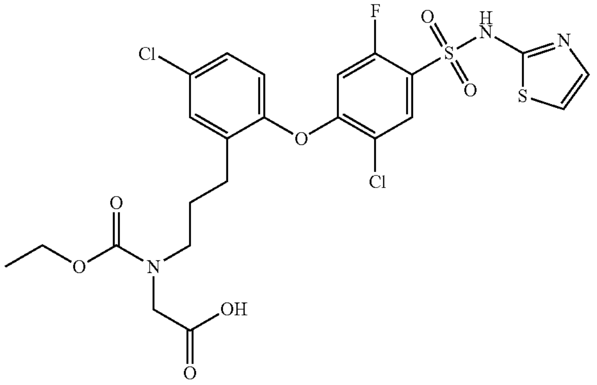 [SMILES: CCOC(=O)N(CCCc1cc(Cl)ccc1Oc1cc(F)c(S(=O)(=O)Nc2nccs2)cc1Cl)CC(=O)O] | 2-((3-(5-chloro-2-(2-chloro-5-fluoro-4-(N-(thiazol-2-yl)sulfamoyl)phenoxy)phenyl)propyl)(ethoxycarbonyl)amino)acetic acid |
| 35 | 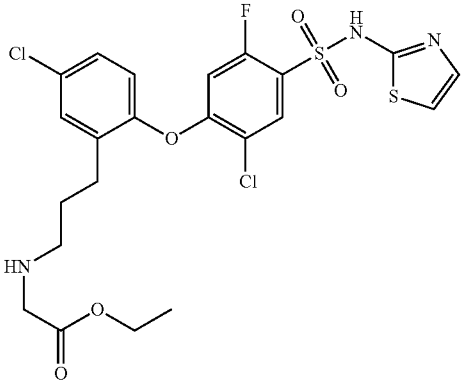 [SMILES: CCOC(=O)CNCCCc1cc(Cl)ccc1Oc1cc(F)c(S(=O)(=O)Nc2nccs2)cc1Cl] | ethyl 2-((3-(5-chloro-2-(2-chloro-5-fluoro-4-(N-(thiazol-2-yl)sulfamoyl)phenoxy)phenyl)propyl)amino)acetate |

TABLE 2-continued

| Prophetic Example | Compound structure | Chemical name* |
|---|---|---|
| 36 | 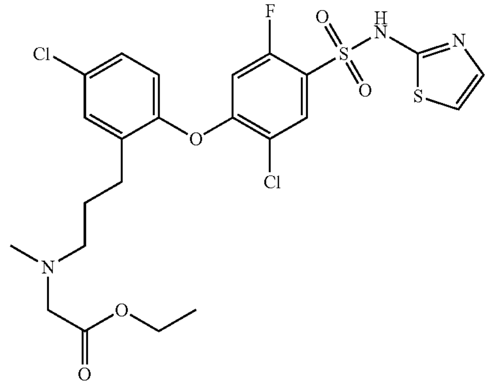 [SMILES: CCOC(=O)CN(C)CCCc1cc(Cl)ccc1Oc1cc(F)c(S(=O)(=O)Nc2nccs2)cc1Cl] | ethyl 2-((3-(5-chloro-2-(2-chloro-5-fluoro-4-(N-(thiazol-2-yl)sulfamoyl)phenoxy)phenyl)propyl)(methyl)amino)acetate |
| 37 | 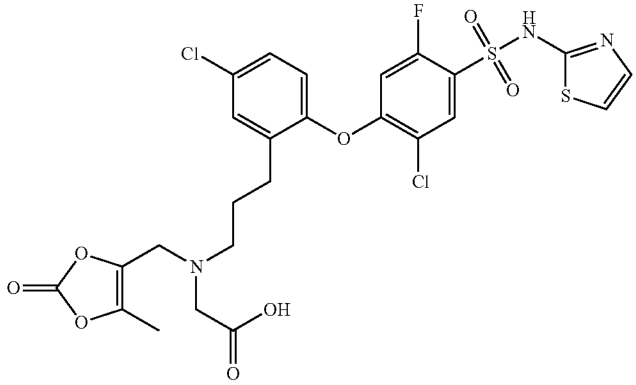 [SMILES: Cc1oc(=O)oc1CN(CCCc1cc(Cl)ccc1Oc1cc(F)c(S(=O)(=O)Nc2nccs2)cc1Cl)CC(=O)O] | 2-((3-(5-chloro-2-(2-chloro-5-fluoro-4-(N-(thiazol-2-yl)sulfamoyl)phenoxy)phenyl)propyl)((5-methyl-2-oxo-1,3-dioxol-4-yl)methyl)amino)acetic acid |
| 38 | 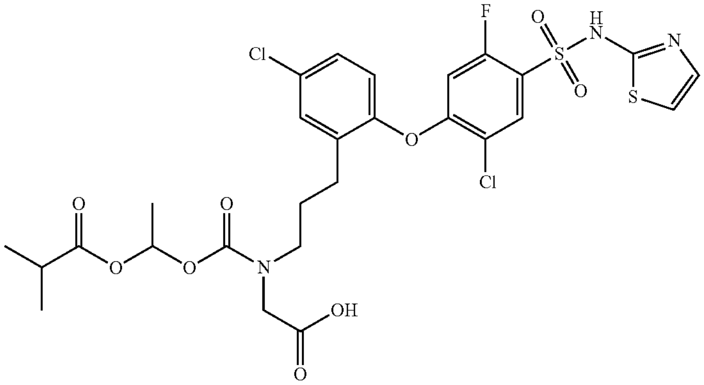 [SMILES: CC(OC(=O)C(C)C)OC(=O)N(CCCc1cc(Cl)ccc1Oc1cc(F)c(S(=O)(=O)Nc2nccs2)cc1Cl)CC(=O)O] | 2-((3-(5-chloro-2-(2-chloro-5-fluoro-4-(N-(thiazol-2-yl)sulfamoyl)phenoxy)phenyl)propyl)((1-(isobutyryloxy)ethoxy)carbonyl)amino)acetic acid |
| 39 | 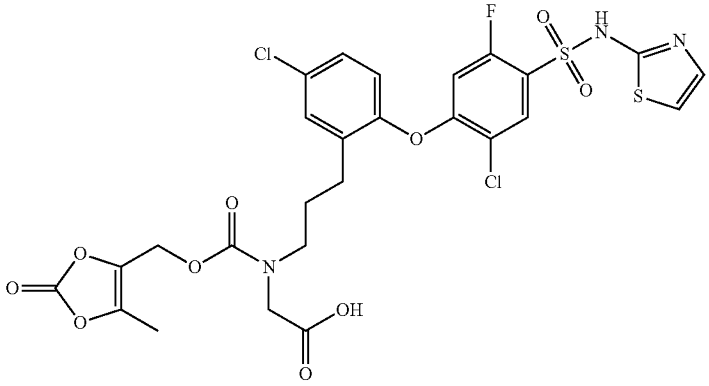 [SMILES: Cc1oc(=O)oc1COC(=O)N(CCCc1cc(Cl)ccc1Oc1cc(F)c(S(=O)(=O)Nc2nccs2)cc1Cl)CC(=O)O] | 2-((3-(5-chloro-2-(2-chloro-5-fluoro-4-(N-(thiazol-2-yl)sulfamoyl)phenoxy)phenyl)propyl)(((5-methyl-2-oxo-1,3-dioxol-4-yl)methoxy)carbonyl)amino)acetic acid |

TABLE 2-continued

| Prophetic Example | Compound structure | Chemical name* |
|---|---|---|
| 40 | 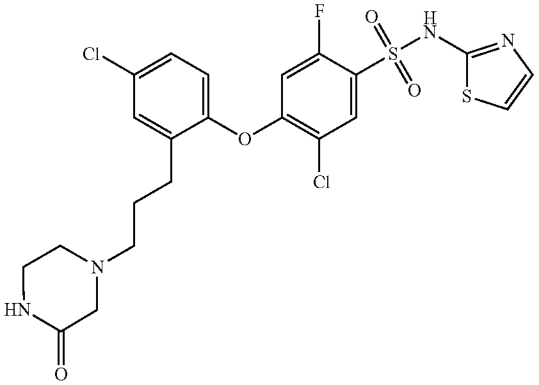 [SMILES: O=C1CN(CCCc2cc(Cl)ccc2Oc2cc(F)c(S(=O)(=O)Nc3nccs3)cc2Cl)CCN1] | 5-chloro-4-(4-chloro-2-(3-(3-oxopiperazin-1-yl)propyl)phenoxy)-2-fluoro-N-(thiazol-2-yl)benzenesulfonamide |
| 41 | 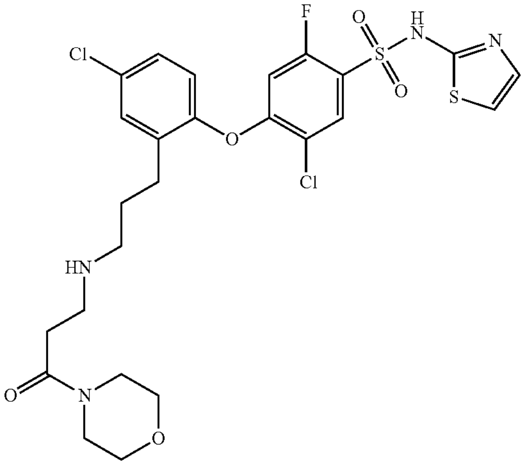 [SMILES: O=C(CCNCCCc1cc(Cl)ccc1Oc1cc(F)c(S(=O)(=O)Nc2nccs2)cc1Cl)N1CCOCC1] | 5-chloro-4-(4-chloro-2-(3-((3-morpholino-3-oxopropyl)amino)propyl)phenoxy)-2-fluoro-N-(thiazol-2-yl)benzenesulfonamide |
| 42 | 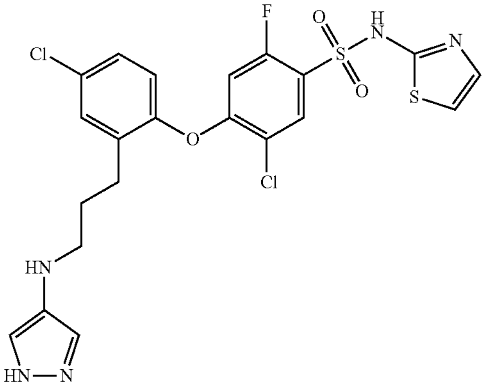 [SMILES: O=S(=O)(Nc1nccs1)c1cc(Cl)c(Oc2ccc(Cl)cc2CCCNc2cn[nH]c2)cc1F] | 4-(2-(3-((1H-pyrazol-4-yl)amino)propyl)-4-chlorophenoxy)-5-chloro-2-fluoro-N-(thiazol-2-yl)benzenesulfonamide |

*Chemical Names automatically generated with ChemDraw Ultra, Version 12.0.

For the proposes of this disclosure, Table 1 and Table 2 serve to define that a particular structure is associated with a particular name. Whenever a particular name is recited in this disclosure or the claims, the chemical structure associated with that particular name shall be the structure identified in Table 1 or Table 2.

In a particular embodiment, the compounds of Formula (I) are those wherein the compound is 2-(4-(2-(4-(N-(1,2,4-thiadiazol-5-yl)sulfamoyl)-2-chloro-5-fluorophenoxy)-5-chlorophenyl)picolinamido)acetic acid, 3-(4-(2-(4-(N-(1,2,4-thiadiazol-5-yl)sulfamoyl)-2-chloro-5-fluorophenoxy)-5-chlorophenyl)picolinamido)propanoic acid, 2-(4-(2-(4-(N-(1,2,4-thiadiazol-5-yl)sulfamoyl)-2-chloro-5-fluorophenoxy)-5-chlorophenyl)picolinamido)propanoic acid, or 3-((3-(2-(4-(N-(1,2,4-thiadiazol-5-yl)sulfamoyl)-2-chloro-5-fluorophenoxy)-5-chlorophenyl)propyl)amino)propanoic acid;

or a pharmaceutically acceptable salt, or a stereoisomeric or tautomeric form thereof.

Further provided herein are compounds of Formula (Ia),

Formula (Ia)

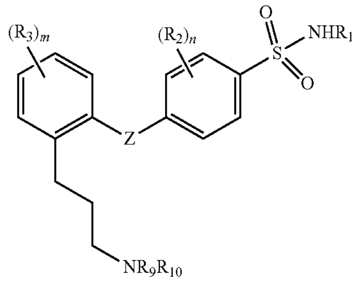

or a pharmaceutically acceptable salt, or a stereoisomeric or tautomeric form thereof, wherein:

Z is —O— or —S—;

$R_1$ is a partially unsaturated or aromatic 5- or 6-membered heterocycle;

$R_2$ is independently at each occurrence —F, —Cl, —Br, —$CH_3$ or —CN;

$R_3$ is independently at each occurrence —H, —F, —Cl, —Br, —$CF_3$, —$OCF_3$, —CN, ($C_1$-$C_{12}$)alkyl, or ($C_1$-$C_{12}$) alkoxy;

$R_9$ is ($C_1$-$C_6$)alkyl, ($C_3$-$C_8$)cycloalkyl, pyrazolyl or pyridinyl; wherein $R_9$ is optionally further substituted with 1 or 2 substituents selected from the group consisting of —COOH, —$COOR_{11}$, —$CONR_{11}R_{12}$, —$SO_2R_{11}$, —$SO_2NR_{11}R_{12}$, —OH, —CN, —$OR_{11}$, and —$NR_{11}R_{12}$; wherein $R_{11}$ and $R_{12}$ may form a 6 membered heterocycloalkyl ring $R_{10}$ is $R_{11}$, —$COR_{11}$, —$COOR_{11}$, —$SO_2R_{11}$, 5-methyl-2-oxo-1,3-dioxol-4-yl,

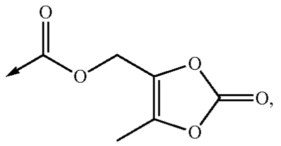

—COO—CH($CH_3$)OCOCH($CH_3$)$_2$; or $R_9$ and $R_{10}$ together form a piperazinone or a 4- to 8-membered heterocycloalkyl ring, wherein said heterocycloalkyl ring is substituted with 1 or 2 substituents selected from the group consisting of —COOH, —$COOR_{11}$, —$CH_2$—$COOR_{11}$, —OH, —$NH_2$, —CN, and ($C_1$-$C_8$)alkoxy;

$R_{11}$ and $R_{12}$ are independently H or ($C_1$-$C_6$)alkyl, optionally substituted with 4- to 8-membered heterocycloalkyl ring; and m and n are each independently 1, 2, 3, or 4.

In a particular embodiment, the compounds of Formula (Ia) are those wherein $R_1$ is an aromatic 5- or 6-membered heterocycle, with 1-3 heteroatoms independently selected from the group consisting of N, O, and S.

In a particular embodiment, the compounds of Formula (Ia) are those wherein $R_1$ is pyridyl or pyrimidinyl.

In a particular embodiment, the compounds of Formula (Ia) are those wherein $R_1$ is an aromatic 5-membered heterocycle with 1 or 2 nitrogen atoms and optionally 1 or 2 sulphur atoms. In a particular embodiment, the compounds of Formula (Ia) are those wherein $R_1$ is thiazolyl, isothiazolyl, or thiadiazolyl. In a particular embodiment, the compounds of Formula (Ia) are those wherein $R_1$ is thiazolyl. In a particular embodiment, the compounds of Formula (Ia) are those wherein $R_1$ is 1,2,4-thiadiazol-5-yl.

In a particular embodiment, the compounds of Formula (Ia) are those wherein $R_2$ is independently at each occurrence —F or —Cl.

In a particular embodiment, the compounds of Formula (Ia) are those wherein n is 1, 2, or 3. In a particular embodiment, the compounds of Formula (Ia) are those wherein n is 2.

In a particular embodiment, the compounds of Formula (Ia) are those wherein Z is —O—.

In a particular embodiment, the compounds of Formula (Ia) are those wherein $R_3$ is independently at each occurrence —H, —F, —Cl, or —Br. In a particular embodiment, the compounds of Formula (Ia) are those wherein $R_3$ is —H or —Cl. In a particular embodiment, the compounds of Formula (Ia) are those wherein $R_3$ is —Cl.

In a particular embodiment, the compounds of Formula (Ia) are those wherein m is 1, 2, or 3. In a particular embodiment, the compounds of Formula (Ia) are those wherein m is 1.

In a particular embodiment, the compounds of Formula (Ia) are those wherein $R_9$ is ($C_1$-$C_6$)alkyl; wherein $R_9$ is optionally further substituted with 1 or 2 substituents selected from the group consisting of —COOH, —COOMe, —$CONH_2$, and —$NH_2$. In a particular embodiment, the compounds of Formula (Ia) are those wherein $R_9$ is methyl or ethyl. In a particular embodiment, the compounds of Formula (Ia) are those wherein $R_9$ is further substituted with —COOH.

In a particular embodiment, the compounds of Formula (Ia) are those wherein $R_{10}$ is —H, —COMe, —COOEt. In a particular embodiment, the compounds of Formula (Ia) are those wherein $R_{10}$ is —H or —COMe. In a particular embodiment, the compounds of Formula (Ia) are those wherein $R_{10}$ is —H.

In a particular embodiment, the compounds of Formula (Ia) are those wherein $R_9$ and $R_{10}$ together form a 4 to 8 membered heterocycloalkyl ring, wherein said heterocycloalkyl ring is substituted with 1 or 2 groups selected from the group consisting of —COOH, —COOMe, —COOEt, —$CH_2$—COOH, and —$NH_2$. In a particular embodiment, the compounds of Formula (I) are those wherein $R_9$ and $R_{10}$ together form a 4 to 8 membered heterocycloalkyl ring, wherein said heterocycloalkyl ring is substituted with 1 or 2 groups selected from the group consisting of —COOH, —$CH_2$—COOH, and —$NH_2$.

In a particular embodiment, the compounds of Formula (Ia) are those wherein $R_9$ and $R_{10}$ together form a piperidine substituted with 1 or 2 groups selected from the group consisting of —COOH, —COOMe, —COOEt, —$CH_2$—COOH, —$CH_2$—COOMe, —$CH_2$—COOEt, and —$NH_2$. In a particular embodiment, the compounds of Formula (Ia) are those wherein $R_9$ and $R_{10}$ together form a piperidine substituted with 1 or 2 groups selected from the group consisting of —COOH, —$CH_2$—COOH, and —$NH_2$.

In a particular embodiment, the compounds of Formula (Ia) are selected from the group consisting of 2-((3-(5-chloro-2-(2-chloro-5-fluoro-4-(N-(thiazol-4-yl)sulfamoyl)phenoxy)phenyl)propyl)amino)acetic acid, 3-((3-(2-(4-(N-(1,2,4-thiadiazol-5-yl)sulfamoyl)-2-chloro-5-fluorophenoxy)-5-chlorophenyl)propyl)amino)propanoic acid, 2-((3-(5-chloro-2-(2-chloro-5-fluoro-4-(N-(thiazol-2-yl)sulfamoyl)phenoxy)phenyl)propyl)amino)acetic acid, 1-(3-(5-chloro-2-(2-chloro-5-fluoro-4-(N-(thiazol-4-yl)sulfamoyl)phenoxy)phenyl)propyl)piperidine-4-carboxylic acid, 3-((3-(5-chloro-2-(2-chloro-5-fluoro-4-(N-(thiazol-4-yl)sulfamoyl)phenoxy)phenyl)propyl)amino)propanoic acid, 4-amino-1-(3-(5-chloro-2-(2-chloro-5-fluoro-4-(N-(thiazol-4-yl)sulfamoyl)phenoxy)phenyl)propyl)piperidine-4-carboxylic acid, 2-amino-4-((3-(5-chloro-2-(2-chloro-5-fluoro-4-(N-(thiazol-4-yl)sulfamoyl)phenoxy)phenyl)propyl)amino)butanoic acid, 2-((3-(5-chloro-2-(2,5-difluoro-4-(N-(thiazol-2-yl)sulfamoyl)phenoxy)phenyl)propyl)amino)acetic acid, 1-(3-(5-chloro-2-(2-chloro-5-fluoro-4-(N-(thiazol-4-yl)sulfamoyl)phenoxy)phenyl)propyl)piperidine-3-carboxylic acid, 2-((3-(2-(4-(N-(1,2,4-thiadiazol-5-yl)sulfamoyl)-2-chloro-5-fluorophenoxy)phenyl)propyl)amino)acetic acid, 2-((3-(5-chloro-2-(2,5-difluoro-4-(N-(thiazol-4-yl)sulfamoyl)phenoxy)phenyl)propyl)amino)acetic acid, 3-((3-(5-chloro-2-(2,5-difluoro-4-(N-(thiazol-4-yl)sulfamoyl)phenoxy)phenyl)propyl)amino)propanoic acid, 3-((3-(5-chloro-2-(2-cyano-4-(N-(thiazol-4-yl)sulfamoyl)phenoxy)phenyl)propyl)amino)propanoic acid, methyl 2-((3-(5-chloro-2-(2-chloro-5-fluoro-4-(N-(thiazol-4-yl)sulfamoyl)phenoxy)phenyl)propyl)amino)acetate, 3-((3-(2-(2-chloro-5-fluoro-4-(N-(thiazol-4-yl)sulfamoyl)phenoxy)-5-fluorophenyl)propyl)amino)propanoic acid, 3-((3-(5-chloro-2-(2-chloro-5-fluoro-4-(N-(thiazol-4-yl)sulfamoyl)phenoxy)phenyl)propyl)amino)propanamide, 2-(N-(3-(5-chloro-2-(2-chloro-5-fluoro-4-(N-(thiazol-4-yl)sulfamoyl)phenoxy)phenyl)propyl)acetamido)acetic acid, 2-(1-(3-(2-(4-(N-(1,2,4-thiadiazol-5-yl)sulfamoyl)-2-chloro-5-fluorophenoxy)-5-chlorophenyl)propyl)piperidin-4-yl)acetic acid, 3-((3-(5-chloro-2-(2-chloro-5-fluoro-4-(N-(thiazol-2-yl)sulfamoyl)phenoxy)phenyl)propyl)amino)propanoic acid, 2-((3-(5-chloro-2-(2-chloro-5-fluoro-4-(N-(thiazol-4-yl)sulfamoyl)phenoxy)phenyl)propyl)amino)-N-methylacetamide, 5-chloro-4-(4-chloro-2-(3-((2-(methylsulfonyl)ethyl)amino)propyl)phenoxy)-2-fluoro-N-(thiazol-4-yl)benzenesulfonamide, and 1-(3-(2-(4-(N-(1,2,4-thiadiazol-5-yl)sulfamoyl)-2-chloro-5-fluorophenoxy)-5-chlorophenyl)propyl)piperidine-4-carboxylic acid;

or a pharmaceutically acceptable salt, or a stereoisomeric or tautomeric form thereof.

In a particular embodiment, the compounds of Formula (Ia) are selected from the group comprising 2-((3-(5-chloro-2-(2-chloro-5-fluoro-4-(N-(thiazol-2-yl)sulfamoyl)phenoxy)phenyl)propyl)(ethoxycarbonyl)amino)acetic acid, ethyl 2-((3-(5-chloro-2-(2-chloro-5-fluoro-4-(N-(thiazol-2-yl)sulfamoyl)phenoxy)phenyl)propyl)amino)acetate, ethyl 2-((3-(5-chloro-2-(2-chloro-5-fluoro-4-(N-(thiazol-2-yl)sulfamoyl)phenoxy)phenyl)propyl)(methyl)amino)acetate, 2-((3-(5-chloro-2-(2-chloro-5-fluoro-4-(N-(thiazol-2-yl)sulfamoyl)phenoxy)phenyl)propyl)((5-methyl-2-oxo-1,3-dioxol-4-yl)methyl)amino)acetic acid, 2-((3-(5-chloro-2-(2-chloro-5-fluoro-4-(N-(thiazol-2-yl)sulfamoyl)phenoxy)phenyl)propyl)((1-(isobutyryloxy)ethoxy)carbonyl)amino)acetic acid, 2-((3-(5-chloro-2-(2-chloro-5-fluoro-4-(N-(thiazol-2-yl)sulfamoyl)phenoxy)phenyl)propyl)(((5-methyl-2-oxo-1,3-dioxol-4-yl)methoxy)carbonyl)amino)acetic acid, 5-chloro-4-(4-chloro-2-(3-(3-oxopiperazin-1-yl)propyl)phenoxy)-2-fluoro-N-(thiazol-2-yl)benzenesulfonamide, 5-chloro-4-(4-chloro-2-(3-((3-morpholino-3-oxopropyl)amino)propyl)phenoxy)-2-fluoro-N-(thiazol-2-yl)benzenesulfonamide, and 4-(2-(3-((1H-pyrazol-4-yl)amino)propyl)-4-chlorophenoxy)-5-chloro-2-fluoro-N-(thiazol-2-yl)benzenesulfonamide;

or a pharmaceutically acceptable salt, or a stereoisomeric or tautomeric form thereof.

Provided herein are compounds of Formula (Ib),

Formula (Ib)

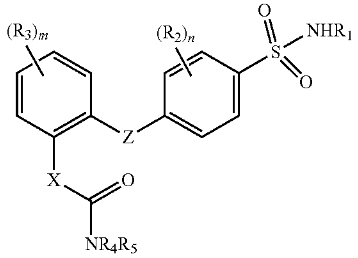

or a pharmaceutically acceptable salt, or a stereoisomeric or tautomeric form thereof, wherein:

Z is —O— or —S—;

X is $(C_6\text{-}C_{10})$aryl or 5- or 6-membered heteroaryl;

$R_1$ is a partially unsaturated or aromatic 5- or 6-membered heterocycle;

$R_2$ is independently at each occurrence —F, —Cl, —Br, —$CH_3$ or —CN;

$R_3$ is independently at each occurrence —H, —F, —Cl, —Br, —$CF_3$, —$OCF_3$, —CN, $(C_1\text{-}C_{12})$alkyl, or $(C_1\text{-}C_{12})$alkoxy;

$R_4$ and $R_5$ are each independently H, $(C_1\text{-}C_9)$alkyl, $(C_4\text{-}C_{12})$cycloalkyl, or $R_4$ and $R_5$ together form a 5- to 7-membered heterocycloalkyl ring; with the proviso that:

$R_4$ and $R_5$ are not both H; and at least one of $R_4$ and $R_5$ independently or said heterocycloalkyl ring formed by $R_4$ and $R_5$ together is substituted with 1 or 2 substituents selected from the group consisting of —$CO_2H$, —$CO_2R_6$, —CN, —OH, —$CONR_7R_8$, and —$NR_7R_8$; wherein:

$R_6$ is $(C_1\text{-}C_{12})$alkyl;

$R_7$ and $R_8$ are each independently H, $(C_1\text{-}C_{12})$alkyl, or $R_7$ and $R_8$ together form a 4- to 7-membered heterocycloalkyl ring; and m and n are each independently 1, 2, 3, or 4.

In a particular embodiment, the compounds of Formula (Ib) are those wherein $R_1$ is an aromatic 5- or 6-membered heterocycle, with 1-3 heteroatoms independently selected from the group consisting of N, O, and S.

In a particular embodiment, the compounds of Formula (Ib) are those wherein $R_1$ is pyridyl or pyrimidinyl.

In a particular embodiment, the compounds of Formula (Ib) are those wherein $R_1$ is an aromatic 5-membered heterocycle with 1 or 2 nitrogen atoms and optionally 1 or 2 sulphur atoms. In a particular embodiment, the compounds of Formula (Ib) are those wherein $R_1$ is thiazolyl, isothiazolyl, or thiadiazolyl. In a particular embodiment, the compounds of Formula (Ib) are those wherein $R_1$ is thiazolyl. In a particular embodiment, the compounds of Formula (Ib) are those wherein $R_1$ is 1,2,4-thiadiazol-5-yl.

In a particular embodiment, the compounds of Formula (Ib) are those wherein $R_2$ is independently at each occurrence —F or —Cl.

In a particular embodiment, the compounds of Formula (Ib) are those wherein n is 1, 2, or 3. In a particular embodiment, the compounds of Formula (Ib) are those wherein n is 2.

In a particular embodiment, the compounds of Formula (Ib) are those wherein Z is —O—.

In a particular embodiment, the compounds of Formula (Ib) are those wherein $R_3$ is independently at each occurrence —F, —Cl, or —Br. In a particular embodiment, the compounds of Formula (Ib) are those wherein $R_3$ is —H or —Cl. In a particular embodiment, the compounds of Formula (Ib) are those wherein $R_3$ is —Cl.

In a particular embodiment, the compounds of Formula (Ib) are those wherein m is 1, 2, or 3. In a particular embodiment, the compounds of Formula (Ib) are those wherein m is 1.

In a particular embodiment, the compounds of Formula (Ib) are those wherein X is 5- or 6-membered heteroaryl. In a particular embodiment, the compounds of Formula (Ib) are those wherein X is pyridyl or pyrimidinyl. In a particular embodiment, the compounds of Formula (Ib) are those wherein X is pyridyl.

In a particular embodiment, the compounds of Formula (Ib) are those wherein $R_4$ is H and $R_5$ is $(C_1-C_9)$alkyl.

In a particular embodiment, the compounds of Formula (Ib) are those wherein $R_5$ is methyl or ethyl, substituted with 1 or 2 substituents selected from the group consisting of —$CO_2H$, —$CO_2R_6$, and —$CONR_7R_8$.

In a particular embodiment, the compounds of Formula (Ib) are those wherein $R_6$ is $(C_1-C_6)$alkyl.

In a particular embodiment, the compounds of Formula (Ib) are those wherein $R_5$ is methyl or ethyl, substituted with —$CO_2H$.

Provided herein are compounds of Formula (Ic),

Formula (Ic)

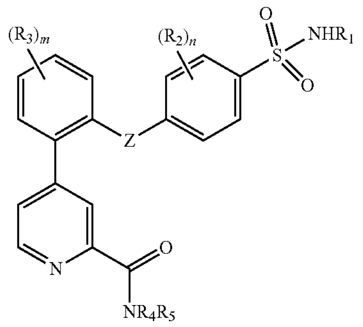

or a pharmaceutically acceptable salt, or a stereoisomeric or tautomeric form thereof, wherein:

Z is —O— or —S—;

$R_1$ is a partially unsaturated or aromatic 5- or 6-membered heterocycle;

$R_2$ is independently at each occurrence —F, —Cl, —Br, —$CH_3$ or —CN;

$R_3$ is independently at each occurrence —H, —F, —Cl, —Br, —$CF_3$, —$OCF_3$, —CN, $(C_1-C_{12})$alkyl, or $(C_1-C_{12})$alkoxy;

$R_4$ and $R_5$ are each independently H, $(C_1-C_9)$alkyl, $(C_4-C_{12})$cycloalkyl, or $R_4$ and $R_5$ together form a 5- to 7-membered heterocycloalkyl ring; with the proviso that:

$R_4$ and $R_5$ are not both H; and at least one of $R_4$ and $R_5$ independently or said heterocycloalkyl ring formed by $R_4$ and $R_5$ together is substituted with 1 or 2 substituents selected from the group consisting of —$CO_2H$, —$CO_2R_6$, —CN, —OH, —$CONR_7R_8$, and —$NR_7R_8$; wherein:

$R_6$ is $(C_1-C_{12})$alkyl;

$R_7$ and $R_8$ are each independently H, $(C_1-C_{12})$alkyl, or $R_7$ and $R_8$ together form a 4- to 7-membered heterocycloalkyl ring; and m and n are each independently 1, 2, 3, or 4.

In a particular embodiment, the compounds of Formula (Ic) are those wherein $R_1$ is an aromatic 5- or 6-membered heterocycle, with 1-3 heteroatoms independently selected from the group consisting of N, O, and S.

In a particular embodiment, the compounds of Formula (Ic) are those wherein $R_1$ is pyridyl or pyrimidinyl.

In a particular embodiment, the compounds of Formula (Ic) are those wherein $R_1$ is an aromatic 5-membered heterocycle with 1 or 2 nitrogen atoms and optionally 1 or 2 sulphur atoms. In a particular embodiment, the compounds of Formula (Ic) are those wherein $R_1$ is thiazolyl, isothiazolyl, or thiadiazolyl. In a particular embodiment, the compounds of Formula (Ic) are those wherein $R_1$ is thiazolyl. In a particular embodiment, the compounds of Formula (Ic) are those wherein $R_1$ is 1,2,4-thiadiazol-5-yl.

In a particular embodiment, the compounds of Formula (Ic) are those wherein $R_2$ is independently at each occurrence —F or —Cl.

In a particular embodiment, the compounds of Formula (Ic) are those wherein n is 1, 2, or 3. In a particular embodiment, the compounds of Formula (Ic) are those wherein n is 2.

In a particular embodiment, the compounds of Formula (Ic) are those wherein Z is —O—.

In a particular embodiment, the compounds of Formula (Ic) are those wherein $R_3$ is independently at each occurrence —F, —Cl, or —Br. In a particular embodiment, the compounds of Formula (I) are those wherein $R_3$ is —H or —Cl. In a particular embodiment, the compounds of Formula (Ic) are those wherein $R_3$ is —Cl.

In a particular embodiment, the compounds of Formula (Ic) are those wherein m is 1, 2, or 3. In a particular embodiment, the compounds of Formula (Ic) are those wherein m is 1.

In a particular embodiment, the compounds of Formula (Ic) are those wherein X is 5- or 6-membered heteroaryl. In a particular embodiment, the compounds of Formula (Ic) are those wherein X is pyridyl or pyrimidinyl. In a particular embodiment, the compounds of Formula (Ic) are those wherein X is pyridyl.

In a particular embodiment, the compounds of Formula (Ic) are those wherein $R_4$ is H and $R_5$ is $(C_1-C_9)$alkyl.

In a particular embodiment, the compounds of Formula (Ic) are those wherein $R_5$ is methyl or ethyl, substituted with 1 or 2 substituents selected from the group consisting of —$CO_2H$, —$CO_2R_6$, and —$CONR_7R_8$.

In a particular embodiment, the compounds of Formula (Ic) are those wherein $R_6$ is $(C_1-C_6)$alkyl.

In a particular embodiment, the compounds of Formula (Ic) are those wherein $R_5$ is methyl or ethyl, substituted with —$CO_2H$.

In a particular embodiment, the compounds of Formula (Ic) are selected from the group consisting of 3-(4-(2-(4-(N-(1,2,4-thiadiazol-5-yl)sulfamoyl)-2-chloro-5-fluorophenoxy)-5-chlorophenyl)picolinamido)propanoic acid, 2-(4-(2-(4-(N-(1,2,4-thiadiazol-5-yl)sulfamoyl)-2-chloro-5-fluorophenoxy)-5-chlorophenyl)picolinamido)acetic acid, 5-(4-(2-(4-(N-(1,2,4-thiadiazol-5-yl)sulfamoyl)-2-chloro-5-fluorophenoxy)-5-chlorophenyl)picolinamido)pentanoic acid, 4-(4-(2-(4-(N-(1,2,4-thiadiazol-5-yl)sulfamoyl)-2-chloro-5-fluorophenoxy)-5-chlorophenyl)picolinamido)butanoic acid, 2-(4-(2-(4-(N-(1,2,4-thiadiazol-5-yl)sulfamoyl)-2-chloro-5-fluorophenoxy)-5-chlorophenyl)picolinamido)propanoic acid, (R)-2-(4-(2-(4-(N-(1,2,4-thiadiazol-5-yl)sulfamoyl)-2-chloro-5-fluorophenoxy)-5-chlorophenyl)picolinamido)propanoic acid, (S)-2-(4-(2-(4-(N-(1,2,4-thiadiazol-5-yl)sulfamoyl)-2-chloro-5-fluorophenoxy)-5-chlorophenyl)picolinamido)propanoic acid, 3-(4-(2-(4-(N-(1,2,4-thiadiazol-5-yl)sulfamoyl)-2-cyano-phenoxy)-5-chlorophenyl)picolinamido)propanoic acid, and 3-(4-(2-(4-(N-(1,2,4-thiadiazol-5-yl)sulfamoyl)-2,5-difluorophenoxy)-5-chlorophenyl)picolinamido)propanoic acid; or a pharmaceutically acceptable salt, or a stereoisomeric or tautomeric form thereof.

Provided herein are compounds of Formula (Id),

Formula (Id)

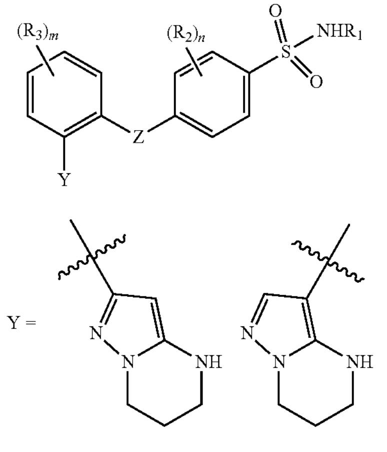

or a pharmaceutically acceptable salt, or a stereoisomeric or tautomeric form thereof, wherein:

Y is 4,5,6,7-tetrahydropyrazolo[1,5-a]pyrimidine-(2-yl or 3-yl);

Z is —O— or —S—;

$R_1$ is a partially unsaturated or aromatic 5- or 6-membered heterocycle;

$R_2$ is independently at each occurrence —F, —Cl, —Br, —$CH_3$ or —CN;

$R_3$ is independently at each occurrence —H, —F, —Cl, —Br, —$CF_3$, —$OCF_3$, —CN, $(C_1\text{-}C_{12})$alkyl, or $(C_1\text{-}C_{12})$alkoxy; and m and n are each independently 1, 2, 3, or 4.

In a certain embodiment, the compounds of Formula (Id) are those wherein Y is 4,5,6,7-tetrahydropyrazolo[1,5-a]pyrimidine-(2-yl or 3-yl). In a particular embodiment, the compounds of Formula (Id) are those wherein Y is 4,5,6,7-tetrahydropyrazolo[1,5-a]pyrimidine-3-yl.

In a particular embodiment, the compounds of Formula (Id) are those wherein $R_1$ is an aromatic 5- or 6-membered heterocycle, with 1-3 heteroatoms independently selected from the group consisting of N, O, and S.

In a particular embodiment, the compounds of Formula (Id) are those wherein $R_1$ is pyridyl or pyrimidinyl.

In a particular embodiment, the compounds of Formula (Id) are those wherein $R_1$ is an aromatic 5-membered heterocycle with 1 or 2 nitrogen atoms and optionally 1 or 2 sulphur atoms. In a particular embodiment, the compounds of Formula (Id) are those wherein $R_1$ is thiazolyl, isothiazolyl, or thiadiazolyl. In a particular embodiment, the compounds of Formula (Id) are those wherein $R_1$ is thiazolyl. In a particular embodiment, the compounds of Formula (Id) are those wherein $R_1$ is 1,2,4-thiadiazol-5-yl.

In a particular embodiment, the compounds of Formula (Id) are those wherein $R_2$ is independently at each occurrence —F or —Cl.

In a particular embodiment, the compounds of Formula (Id) are those wherein n is 1, 2, or 3. In a particular embodiment, the compounds of Formula (Id) are those wherein n is 2.

In a particular embodiment, the compounds of Formula (Id) are those wherein Z is —O—.

In a particular embodiment, the compounds of Formula (Id) are those wherein $R_3$ is independently at each occurrence —F, —Cl, or —Br. In a particular embodiment, the compounds of Formula (Id) are those wherein $R_3$ is —H or —Cl. In a particular embodiment, the compounds of Formula (Id) are those wherein $R_3$ is —Cl.

In a particular embodiment, the compounds of Formula (Id) are those wherein m is 1, 2, or 3. In a particular embodiment, the compounds of Formula (Id) are those wherein m is 1.

In a particular embodiment, the compound of Formula (Id) is 5-chloro-4-(4-chloro-2-(4,5,6,7-tetrahydropyrazolo[1,5-a]pyrimidin-3-yl)phenoxy)-2-fluoro-N-(thiazol-4-yl)benzenesulfonamide; or a pharmaceutically acceptable salt, or a stereoisomeric or tautomeric form thereof.

It should also be noted the Compounds provided herein can contain unnatural proportions of atomic isotopes at one or more of the atoms. For example, the Compounds may be radiolabeled with radioactive isotopes, such as for example tritium ($^3H$), iodine-125 ($^{125}I$), sulfur-35 ($^{35}S$), or carbon-14 ($^{14}C$), or may be isotopically enriched, such as with deuterium ($^2H$), carbon-13 ($^{13}C$), or nitrogen-15 ($^{15}N$). As used herein, an “isotopologue” is an isotopically enriched Compound. The term “isotopically enriched” refers to an atom having an isotopic composition other than the natural isotopic composition of that atom. “Isotopically enriched” may also refer to a Compound containing at least one atom having an isotopic composition other than the natural isotopic composition of that atom. The term “isotopic composition” refers to the amount of each isotope present for a given atom. Radiolabeled and isotopically enriched Compounds are useful as therapeutic agents, e.g., cancer and inflammation therapeutic agents; research reagents, e.g., binding assay reagents; and diagnostic agents, e.g., in vivo imaging agents. All isotopic variations of the Compounds as described herein, whether radioactive or not, are intended to be encompassed within the scope of the embodiments provided herein. In some embodiments, there are provided isotopologues of the Compounds, for example, the isotopologues are deuterium, carbon-13, or nitrogen-15 enriched Compounds.

In certain embodiments, a Compound provided herein modulates the activity of a sodium ion channel, such as a voltage-gated sodium ion channel. In more specific embodiments, such a voltage-gated sodium ion channel is NaV1.7 (whose alpha subunit is encoded by the human gene SCN9A).

In certain embodiments, a Compound provided herein reduces the sodium ion flux through NaV1.7 by at least 10%, 20%, 30%, 40%, 50%, 60%, 70%, 80%, 90%, 95%, 98%, 99%, or 100%, or by ranges between any of the recited percentages (e.g., 10-20%, 10-30%, 10-40%, 20-30%, or 20-40%) relative to the activated channel in the absence of the compound.

In certain embodiments, a Compound provided herein increases the sodium ion flux through NaV1.7 by at least 10%, 20%, 30%, 40%, 50%, 60%, 70%, 80%, 90%, 100%, 250%, 500%, 750%, or 1000%, or by ranges between any of the recited percentages (e.g., 10-20%, 10-30%, 10-40%, 20-30%, or 20-40%) relative to the activated channel in the absence of the compound.

In certain embodiments, a Compound provided herein, desensitizes the response of NaV1.7 to the change in membrane potential such that the channel requires at least 10%, 20%, 30%, 40%, 50%, 60%, 70%, 80%, 90%, or 100%, or ranges between any of the recited percentages (e.g., 10-20%, 10-30%, 10-40%, 20-30%, or 20-40%) higher change in membrane potential to be activated relative to the channel in the absence of the compound.

In certain embodiments, a Compound provided herein, sensitizes the response of NaV1.7 to the change in membrane potential such that the channel requires at least 10%, 20%, 30%, 40%, 50%, 60%, 70%, 80%, 90%, or 100%, or ranges between any of the recited percentages (e.g., 10-20%, 10-30%, 10-40%, 20-30%, or 20-40%) lower change in membrane potential to be activated relative to the channel in the absence of the compound.

In certain embodiments, a Compound provided herein, affects a voltage-gated sodium ion channel, e.g., NaV1.7, in one or more of the following states: deactivated (closed), activated (open), or inactivated (closed).

In certain embodiments, a Compound provided herein, affects activation, inactivation, or deinactivation of a voltage-gated sodium ion channel, e.g., NaV1.7.

In certain embodiments, a Compound provided herein, modulates NaV1.7 specifically, i.e., the compound modulates NaV1.7 to at least 10%, 20%, 30%, 40%, 50%, 60%, 70%, 80%, 90%, 100%, 250%, 500%, 750%, or 1000% higher degree than another voltage-gated sodium ion channel (such as NaV1.1, NaV1.2, NaV1.3, NaV1.4, NaV1.5, NaV1.6, NaV1.8, and/or NaV1.9), or to a higher degree between any of the recited percentages (e.g., 10-20%, 10-30%, 10-40%, 20-30%, or 20-40%) than another voltage-gated sodium channel.

Any assay known to the skilled artisan can be used to test the effect of a compound provided herein on a voltage-gated sodium ion channel. In certain embodiments, a cell culture assay is used, wherein the voltage-gated sodium ion channel is recombinantly expressed in the cultured cells. In certain more specific embodiments, the alpha subunit of the voltage-gated sodium ion channel is expressed but no accessory proteins are recombinantly expressed in the same cell. In a specific embodiment, SCN9A and SCN9B1 and SCN9B2 are co-expressed in the same cell. In other embodiments, the alpha subunit of the voltage-gated sodium ion channel is expressed and at least one accessory protein (e.g., a beta-subunit) is co-expressed in the same cell.

In certain embodiments, an FDSS membrane potential assay can be used to test the activity of the voltage-gated sodium ion channel (see the Section entitled "FDSS Membrane Potential in vitro Assay" below). In other embodiments, the membrane potential is measured directly using. In certain embodiments, the current through a voltage-gated sodium ion channel is tested using the patch clamp method.

4.3 Methods for Making Compounds

A compound of Formula (Ia) can be synthesized according to synthetic Scheme 1. An $R_3$ substituted 2-hydroxybenzaldehyde or 2-mercaptobenzaldehyde is reacted under Horner-Wadsworth-Emmons ("HWE") conditions with formylmethylene-triphenylphosphorane to give an α,β-unsaturated aldehyde, Intermediate A. Intermediate A is reacted with $HNR_9R_{10}$ under reductive amination conditions using, for example, sodium borohydride, to give Intermediate B. Intermediate B is then reduced to give Intermediate C using, for example, hydrogen in the presence of metal catalyst, such as palladium on carbon. Intermediate C is reacted with a fluoro-substituted phenylsulfonamide, wherein the sulfonamide nitrogen is optionally protected by a group ("PG"), such as tert-butoxycarbonyl ("BOC") or 2,4-dimethoxybenzyl, in presence of a base, such as potassium carbonate, to give Intermediate D. Deprotection of the sulfonamide group of Intermediate D by using, for example, hydrochloric acid, gives a compound of Formula (Ia).

Scheme 1

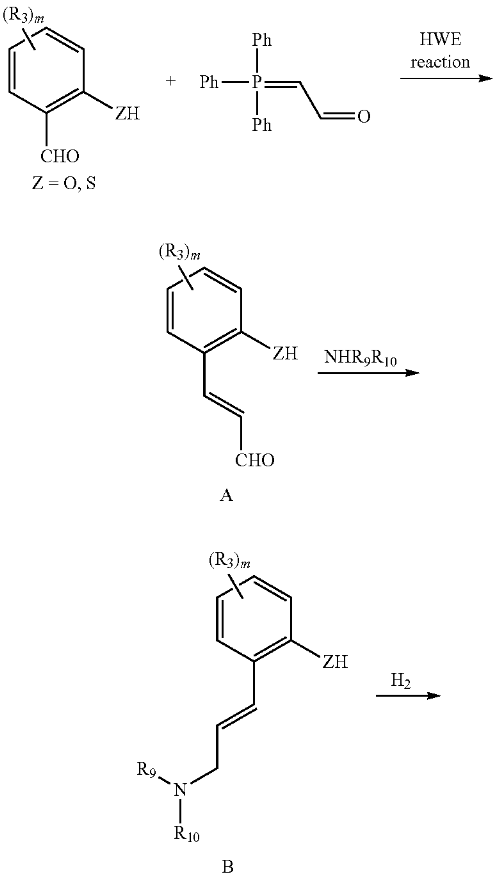

-continued

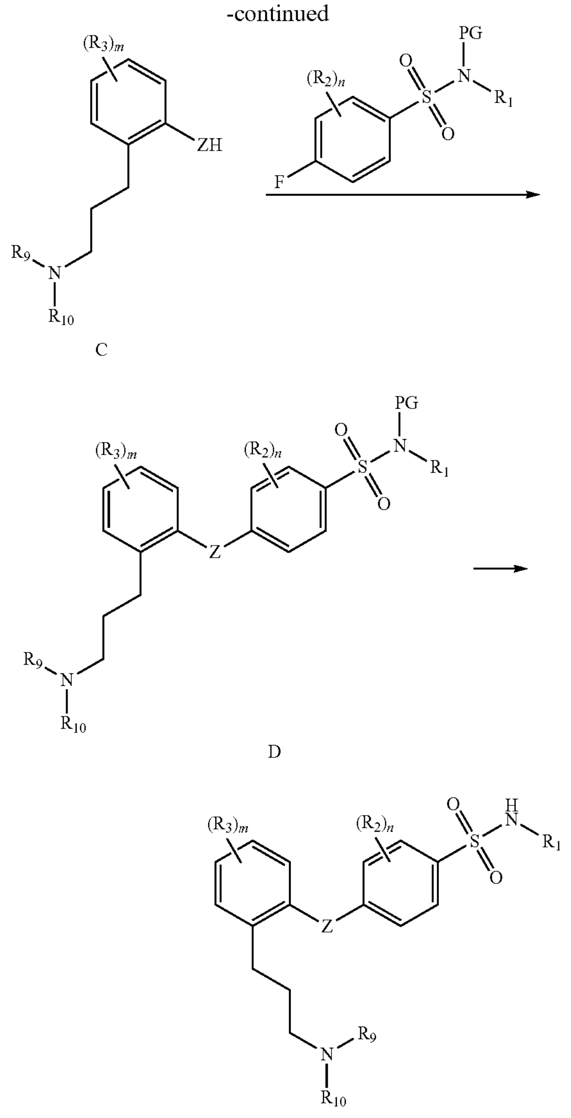

Ia

Scheme 2

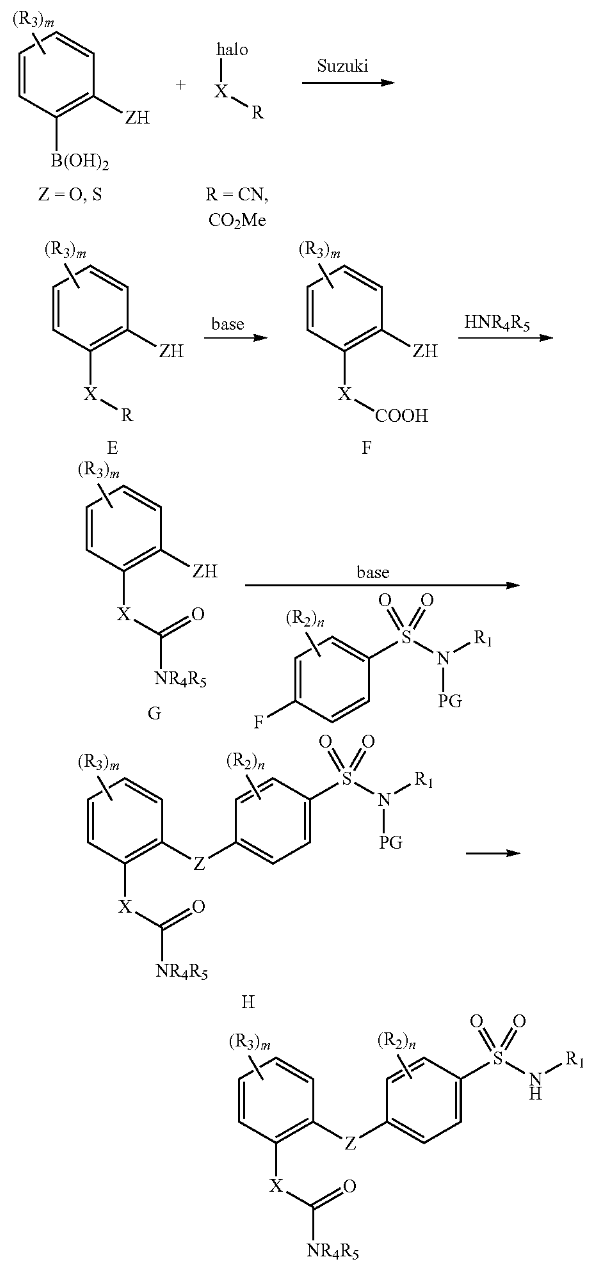

Ib

A compound of Formula (Ib) can be prepared according to synthetic Scheme 2. A Suzuki coupling between an $R_3$ substituted 2-hydroxy-boronic acid or 2-mercapto-boronic acid and derivative of X, wherein X is, for example, a $(C_6-C_{10})$aryl or 5- or 6-membered heteroaryl, such as a 4-halo-picolinonitrile or a 4-halo-picolinic ester (e.g., a methyl picolinate), wherein the halo substituent is, for example, a chloro or bromo substituent, provides Intermediate E. Intermediate E is reacted with a base, such as potassium hydroxide, to give Intermediate F. Intermediate F is reacted with $NHR_4R_5$ to form the amide Intermediate G using, for example, 1-ethyl-3-(3-dimethylaminopropyl)carbodiimide ("EDC") and 1-hydroxy-1H-benzotriazole ("HOBt"). Intermediate G is reacted with a fluoro-substituted phenylsulfonamide, wherein the sulfonamide nitrogen is optionally protected by a group, such as BOC or 2,4-dimethoxybenzyl, in presence of a base, such as potassium carbonate, to give Intermediate H. Deprotection of the sulfonamide group of Intermediate H by using, for example, hydrochloric acid, gives a compound of Formula (Ib).

A compound of Formula (Ic) can be prepared according to synthetic Scheme 3. A Suzuki coupling between an $R_3$ substituted 2-hydroxy-boronic acid or 2-mercapto-boronic acid and pyridine derivative, such as a 4-halo-picolinonitrile or a 4-halo-picolinic ester (e.g., a methyl picolinate), wherein the halo substituent is, for example, a chloro or bromo substituent, provides Intermediate I. Intermediate I is reacted with a base, such as potassium hydroxide, to give Intermediate J. Intermediate J is reacted with $NHR_4R_5$ to form the amide Intermediate K using, for example, EDC and HOBt. Intermediate K is reacted with a fluoro-substituted phenylsulfonamide, wherein the sulfonamide nitrogen is optionally protected by a group, such as BOC or 2,4-dimethoxybenzyl, in presence of a base, such as potassium carbonate, to give Intermediate L. Deprotection of the sulfonamide group of Intermediate L by using, for example, hydrochloric acid, gives a compound of Formula (Ic).

Scheme 3

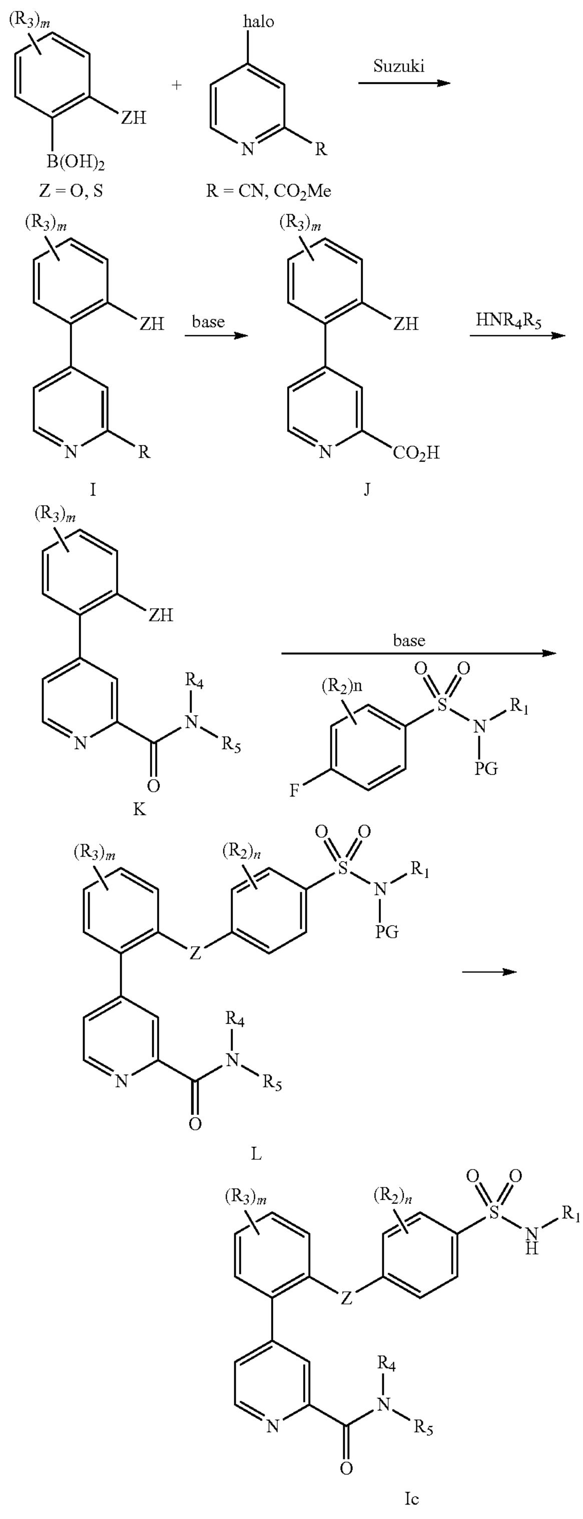

I
J
K
L
Ic

A compound of Formula (Id) can be prepared according to synthetic Scheme 4. Phenylacetonitrile derivative M with a protected hydroxy or thiol group, such as a methyl protected hydroxy group, i.e., a —OMe group, is formylated by using, for example, Na/ethyl formate or NaOEt/ethyl formate to give Intermediate N. Intermediate N is reacted with hydrazine to provide Intermediate O. Intermediate O is reacted with dihaloalkanes, such as 1,3-dibromopropane, under basic conditions, for example, in presence of NaH or $Cs_2CO_3$, to give Intermediate P. Intermediate P, after deprotection of the phenol or thiol, for example, by reacting a methyl protected hydroxy group with $BBr_3$, can undergo same synthetic sequence as described Scheme 1, Scheme 2, or Scheme 3 to give compound S, which is a compound of Formula (Id). Furthermore, Intermediate W, which is deprotected and subjected to the procedures described and referred to in this paragraph to give compounds of Formula (Id), can be obtained as follows: Intermediate T is reacted under Suzuki conditions in presence of a base and a palladium catalyst with Intermediate U or U', wherein R of Intermediate U or U' is a nitro group or a suitably protected amino group, to give Intermediate V. Intermediate V is subjected to conditions, which reduce the nitro group to an amino group or deprotect the nitrogen to release an amino group, such as zinc in acetic acid or hydrogen and Raney-Nickel, to give Intermediate W.

Scheme 4

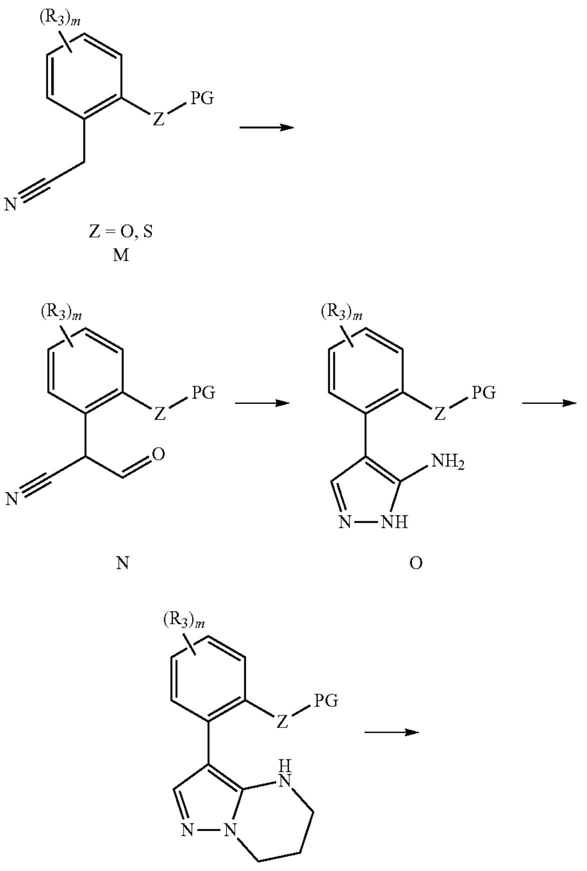

M
N
O
P

-continued

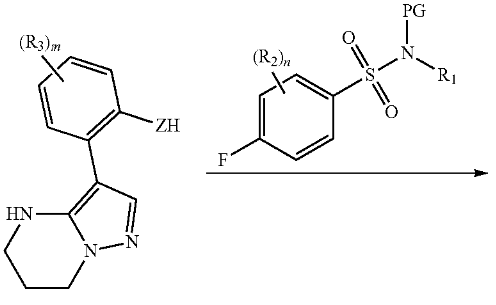

G

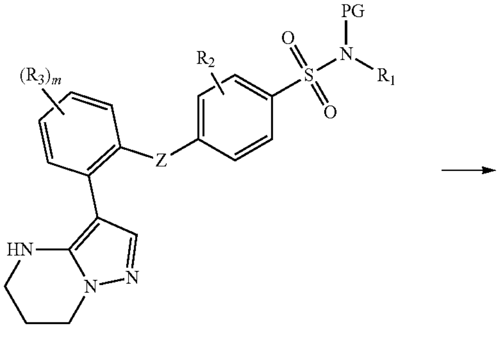

R

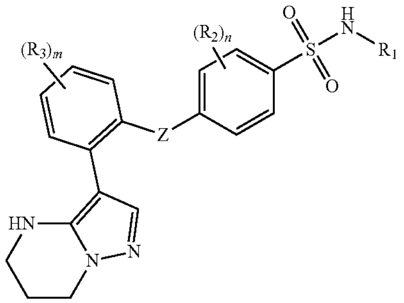

S

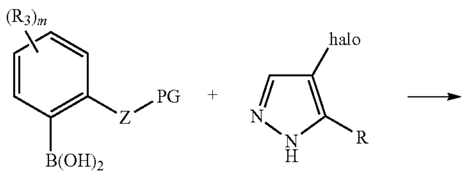

T U

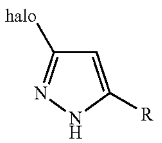

U'

R = $NO_2$, N(PG)

-continued

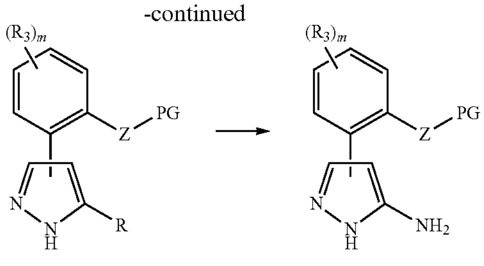

V W

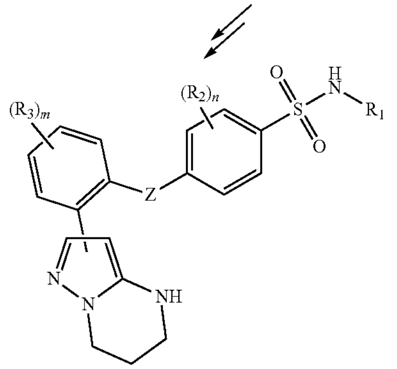

Id 4.4 Methods of Use

Provided herein are methods for the treatment or prevention of pain in a subject in need thereof, wherein the methods comprise administering to the patient in need of such treatment or prevention a Compound provided herein (i.e., a compound of Formula (I), a compound of Formula (Ia), a compound of Formula (Ib), a compound of Formula (Ic), a compound of Formula (Id), a compound listed in Table 1, or a compound listed in Table 2).

Provided herein are methods for managing pain comprising administering to a subject in need thereof, a therapeutically effective amount of a Compound, or a pharmaceutically acceptable salt, solvate or tautomeric form thereof.

Provided herein are methods for treating neuropathic pain comprising administering to a subject in need thereof, a therapeutically effective amount of a Compound, or a pharmaceutically acceptable salt, solvate or tautomeric form thereof.

Provided herein are methods for treating pain comprising use of a Compound, as a voltage-gated sodium channel inhibitor. In a particular embodiment the methods are those, wherein the pain is neuropathic, nociceptive or inflammatory pain. In a particular embodiment the methods are those, wherein the voltage-gated sodium channel is NaV1.7.

Provided herein are methods for treating or preventing a NaV1.7-dysfunction-associated disorder comprising administering to a subject in need thereof, a therapeutically effective amount of a Compound, or a pharmaceutically acceptable salt, solvate or tautomeric form thereof.

Provided herein are methods for prevention or treatment of pain in a subject, wherein the method comprises administering to the subject in need of such prevention or treatment a therapeutically effective amount of a Compound. In a particular embodiment the methods are those, wherein the therapeutically effective amount of a Compound is effective to alleviate pain in a subject, wherein the Compound shows a reduction in pain response in the Formalin Assay (in phase 1 or phase 2, or both) (see Section 5.1.2) at a dose between 0.1 mg/kg and 1,000 mg/kg, at a dose between 0.5 mg/kg and 100 mg/kg, at a dose between 1 mg/kg to 50 mg/kg, or at a dose of 5 mg/kg. In certain embodiments, a Compound provided herein shows a reduction in pain response in the Formalin Assay (in phase 1 or phase 2, or both) by at least 10%, 20%, 30%, 40%, 50%, 60%, 70%, 80%, 90%, 95%, 98%, 99%, or 100%, or by ranges between any of the recited percentages (e.g., 10-20%, 10-30%, 10-40%, 20-30%, or 20-40%) relative to a vehicle control. In a particular embodiment the methods are those, wherein the pain is nociceptive pain, such as that resulting from physical trauma (e.g., a cut or contusion of the skin; or a chemical or thermal burn), osteoarthritis, rheumatoid arthritis or tendonitis; myofascial pain; neuropathic pain, such as that associated with stroke, diabetic neuropathy, luetic neuropathy, postherpetic neuralgia, trigeminal neuralgia, fibromyalgia, or painful neuropathy induced iatrogenically by drugs; or mixed pain (i.e., pain with both nociceptive and neuropathic components); visceral pain; headache pain (e.g., migraine headache pain); CRPS; CRPS type I; CRPS type II; RSD; reflex neurovascular dystrophy; reflex dystrophy; sympathetically maintained pain syndrome; causalgia; Sudeck atrophy of bone; algoneurodystrophy; shoulder hand syndrome; post-traumatic dystrophy; autonomic dysfunction; autoimmune-related pain; inflammation-related pain; cancer-related pain; phantom limb pain; chronic fatigue syndrome; post-operative pain; spinal cord injury pain; central post-stroke pain; radiculopathy; sensitivity to temperature, light touch or color change to the skin (allodynia); pain from hyperthermic or hypothermic conditions; and other painful conditions (e.g., diabetic neuropathy, luetic neuropathy, postherpetic neuralgia, trigeminal neuralgia); chronic pain; or acute pain.

Provided herein are methods modulating the activity of a voltage-gated sodium channel, wherein the method comprises contacting a cell that expresses the voltage-gated sodium channel with a Compound. In a particular embodiments the methods are those, wherein the voltage-gated sodium channel is NaV1.7. In a particular embodiments the methods are those, wherein the method results in inhibition of the voltage-gated sodium channel.

In certain embodiments, a Compound provided herein, is administered to a patient population with a gain of function mutation in a gene encoding the alpha subunit of a voltage gated sodium ion channel, such as NaV1.7.

In certain embodiments, a Compound provided herein is administered to a patient population diagnosed with erythromelalgia, primary erythromelalgia, paroxysmal extreme pain disorder (PEPD), or NaV1.7-associated fibromyalgia.

4.5 Pharmaceutical Compositions and Routes of Administration

Provided herein are pharmaceutical compositions comprising a Compound provided herein and a pharmaceutically acceptable carrier. In a particular embodiment the pharmaceutical compositions are those, wherein the composition is suitable for topical, oral, subcutaneous, or intravenous administration.

Provided herein are compositions comprising an effective amount of a Compound and compositions comprising an effective amount of a Compound and a pharmaceutically acceptable carrier or vehicle. In some embodiments, the pharmaceutical composition described herein are suitable for oral, parenteral, mucosal, transdermal or topical administration.

The Compounds can be administered to a patient orally or parenterally in the conventional form of preparations, such as capsules, microcapsules, tablets, granules, powder, troches, pills, suppositories, injections, suspensions and syrups. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the Compound in the pharmaceutical composition may be at a level that will exercise the desired effect; for example, about 0.1 mg/kg to about 1000 mg/kg or about 0.5 mg/kg to about 100 mg/kg of a patient's body weight in unit dosage for both oral and parenteral administration.

The dose of a Compound to be administered to a patient is rather widely variable and can be the judgment of a health-care practitioner. In general, the Compounds can be administered one to four times a day in a dose of about 0.1 mg/kg of a patient's body weight to about 1000 mg/kg of a patient's body weight in a patient, but the above dosage may be properly varied depending on the age, body weight and medical condition of the patient and the type of administration. In one embodiment, the dose is about 0.05 mg/kg of a patient's body weight to about 500 mg/kg of a patient's body weight, 0.05 mg/kg of a patient's body weight to about 100 mg/kg of a patient's body weight, about 0.5 mg/kg of a patient's body weight to about 100 mg/kg of a patient's body weight, about 0.1 mg/kg of a patient's body weight to about 50 mg/kg of a patient's body weight or about 0.1 mg/kg of a patient's body weight to about 25 mg/kg of a patient's body weight. In one embodiment, one dose is given per day. In another embodiment, two doses are given per day. In any given case, the amount of the Compound administered will depend on such factors as the solubility of the active component, the formulation used and the route of administration.

In another embodiment, provided herein are methods for the treatment of pain comprising the administration of about 7.5 mg/day to about 75 g/day, about 3.75 mg/day to about 37.5 g/day, about 3.75 mg/day to about 7.5 g/day, about 37.5 mg/day to about 7.5 g/day, about 7.5 mg/day to about 3.75 g/day, about 3.75 mg/day to about 1.875 g/day, about 3.75 mg/day to about 1,000 mg/day, about 3.75 mg/day to about 800 mg/day, about 3.75 mg/day to about 500 mg/day, about 3.75 mg/day to about 300 mg/day, or about 3.75 mg/day to about 150 mg/day of a Compound to a patient in need thereof. In a particular embodiment, the methods disclosed herein comprise the administration of 1 mg/day, 5 mg/day, 10 mg/day, 15 mg/day, 20 mg/day, 30 mg/day, 40 mg/day, 45 mg/day, 50 mg/day, 60 mg/day, 75 mg/day, 100 mg/day, 125 mg/day, 150 mg/day, 200 mg/day, 250 mg/day, 300 mg/day, 400 mg/day, 600 mg/day, 800 mg/day, 1,000 mg/day, 1,500 mg/day, 2,000 mg/day, 2,500 mg/day, 5,000 mg/day, or 7,500 mg/day of a Compound to a patient in need thereof.

In another embodiment, provided herein are unit dosage formulations that comprise between about 7.5 mg to about 75 g, about 3.75 mg to about 37.5 g, about 3.75 mg to about 7.5 g, about 37.5 mg to about 7.5 g, about 7.5 mg to about 3.75 g, about 3.75 mg to about 1.875 g, about 3.75 mg to about 1,000 mg, about 3.75 mg to about 800 mg, about 3.75 mg to about 500 mg, about 3.75 mg to about 300 mg, or about 3.75 mg to about 150 mg of a Compound.

In a particular embodiment, provided herein are unit dosage formulation comprising about 1 mg, 5 mg, 10 mg, 15 mg, 20 mg, 30 mg, 40 mg, 45 mg, 50 mg, 60 mg, 75 mg, 100 mg, 125 mg, 150 mg, 200 mg, 250 mg, 300 mg, 400 mg, 600 mg, 800 mg 1,000 mg, 1,500 mg, 2,000 mg, 2,500 mg, 5,000 mg, or 7,500 mg of a Compound.

In another embodiment, provided herein are unit dosage formulations that comprise a Compound dosage that achieves a target plasma concentration of the Compound in a patient or an animal model. In a particular embodiment, provided herein are unit dosage formulations that achieves a plasma concentration of the Compound ranging from approximately 0.001 μg/mL to approximately 100 mg/mL, approximately 0.01 μg/mL to approximately 100 mg/mL, approximately 0.01 μg/mL to approximately 10 mg/mL, approximately 0.1 μg/mL to approximately 10 mg/mL, approximately 0.1 μg/mL to approximately 500 μg/mL, approximately 0.1 μg/mL to approximately 500 μg/mL, approximately 0.1 μg/mL to approximately 100 μg/mL, or approximately 0.5 μg/mL to approximately 10 μg/mL in a patient or an animal model. To achieve such plasma concentrations, a Compound or a pharmaceutical composition thereof may be administered at doses that vary from 0.001 μg to 100,000 mg, depending upon the route of administration. In certain embodiments, subsequent doses of a Compound may be adjusted accordingly based on the plasma concentrations of the Compound achieved with initial doses of the Compound or pharmaceutical composition thereof administered to the subject.

A Compound can be administered once, twice, three, four or more times daily.

A Compound can be administered orally for reasons of convenience. In one embodiment, when administered orally, a Compound is administered with a meal and water. In another embodiment, the Compound is dispersed in water or juice (e.g., apple juice or orange juice) and administered orally as a suspension. In another embodiment, when administered orally, a Compound is administered in a fasted state.

The Compound can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing a Compound without an additional carrier, excipient or vehicle.

In another embodiment, provided herein are compositions comprising an effective amount of a Compound and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts. In general, all of the compositions are prepared according to known methods in pharmaceutical chemistry. Capsules can be prepared by mixing a Compound with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. In one embodiment, the pharmaceutical composition is lactose-free. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the die. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a Compound as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the Compound can be delayed or prolonged by proper formulation. For example, a slowly soluble pellet of the Compound can be prepared and incorporated in a tablet or capsule, or as a slow-release implantable device. The technique also includes making pellets of several different dissolution rates and filling capsules with a mixture of the pellets. Tablets, capsules, or pellets can be coated with a film that resists dissolution for a predictable period of time (the coating may comprise, for example, polymethylacrylates or ethyl cellulose). Even the parenteral preparations can be made long-acting, by dissolving or suspending the Compound in oily or emulsified vehicles that allow it to disperse slowly in the serum.

5 EXAMPLES

5.1 Biological Examples

5.1.1 In Vitro Assays

Recombinant NaV Cell Lines

In vitro assays were performed in recombinant cell line that stably express a heterotrimeric protein of interest from an introduced nucleic acid encoding the alpha subunit (hNav1.7, SCN9A), the beta subunit (SCNB1) and the beta subunit (SCNB2). The cell line was constructed in Human Embryonic Kidney 293 cells. Additional cell lines stably expressing recombinant Nav1.7 or Nav1.5 alpha subunit alone or in combination with various beta subunits can also be used in in-vitro assays.

To make cells and cell lines provided herein, one can use, for example, the technology described in U.S. Pat. No. 6,692,965 and WO/2005/079462. Both of these documents are incorporated herein by reference in their entirety. This technology provides real-time assessment of millions of cells such that any desired number of clones (from hundreds to thousands of clones) expressing the desired gene(s) can be selected. Using cell sorting techniques, such as flow cytometric cell sorting (e.g., with a FACS machine) or magnetic cell sorting (e.g., with a MACS machine), one cell per well is automatically deposited with high statistical confidence in a culture vessel (such as a 96 well culture plate). The speed and automation of the technology allows multigene recombinant cell lines to be readily isolated.

FDSS Membrane Potential In-Vitro Assay

Membrane Potential Dye(s):

Blue membrane potential dye (Molecular Devices Inc.), or membrane potential-sensitive dye, HLB021-152 (AnaSpec) combined with a fluorescence quencher e.g. Dipicrylamine (DPA), Acid Violet 17 (AV 17), Diazine Black (DB), HLB30818, FD and C Black Shade, Trypan Blue, Bromophenol Blue, HLB30701, HLB30702, HLB30703, Nitrazine Yellow, Nitro Red, DABCYL (Molecular Probes), FD and C Red NO. 40, QSY (Molecular Probes), metal ion quenchers (e.g., $Co^{2+}$, $Ni^{2+}$, $Cu^{2+}$), and iodide ion.

Assay Agonists:

Veratridine and scorpion venom proteins modulate the activity of voltage-gated sodium channels through a combination of mechanisms, including an alteration of the inactivation kinetics.

The resulting activation of sodium channels in stable NaV1.7-expressing cells changes cell membrane potential and the fluorescent signal increases as a result of depolarization.

Veratridine and scorpion venom from *Leiurus quinquestriatus quinquestriatus* can be purchased from Sigma-Aldrich (St. Louis, Mo.). Stock solutions were prepared as 10 mM (veratridine) in DMSO and as 1 mg/ml (scorpion venom) in de-ionised water. The sodium channels agonists were diluted in assay buffer to a 4× concentration with final concentration being 2-25 μM for veratridine and 2-20 μg/ml for scorpion venom.

Test compounds were prepared as 2-10 mM stock in DMSO. The stock solutions were further diluted in DMSO in serial dilution steps and then transferred to assay buffer as 4× of the final assay concentrations. Test compounds were added during the first addition (pre-stimulation) step in the kinetic read. All test compound concentrations were evaluated in triplicate.

Cells stably expressing NaV1.7 α, β1 and β2 subunits were maintained under standard cell culture conditions in Dulbecco's Modified Eagles medium supplemented with 10% fetal bovine serum, glutamine and HEPES. On the day before assay, the cells were harvested from stock plates using cell dissociation reagent, e.g., trypsin, CDB (GIBCO) or cell-stripper (Mediatech), and plated at 10,000-25,000 cells per well in 384 well plates in growth media. The assay plates were maintained in a 37° C. cell culture incubator under 5% $CO_2$ for 22-48 hours. The media was then removed from the assay plates and membrane potential fluorescent dye diluted in load buffer (137 mM NaCl, 5 mM KCl, 1.25 mM $CaCl_2$, 25 mM HEPES, 10 mM glucose) was added. The cells were incubated with the membrane potential dye for 45-60 mins at 37° C. The dye-loaded assay plates were then placed in the high-throughput fluorescent plate reader (Hamamatsu FDSS). The kinetic read was started with assay plate imaging every second. After 10 s, the assay buffer alone, or test compound diluted in the assay buffer, were added to the cells ($1^{st}$ addition step) and the kinetic read continued every 2 s for 2 mins total after which cells were stimulated with veratridine and scorpion venom ($2^{nd}$ addition step) diluted in assay buffer to evaluate the effects of the test compounds.

Control response elicited by veratridine and scorpion venom with buffer only (without test compounds added) was taken as the maximal response. Assay results are expressed in relative fluorescence units (RFU) and can be determined by using the maximum signal during the $2^{nd}$ addition/stimulation step or by computing the difference of maximum and minimum signal during the $2^{nd}$ addition/stimulation step. The signal inhibition was estimated for each test compound concentration in triplicate. The data were analyzed using GraphPad Prism 5.01 software to determine the IC50 value for the test compound.

Examples 1, 2, 3, 12, 13, 16, 26, 32 showed IC50 values less than 0.13 μM; examples 4, 5, 6, 7, 8, 9, 10, 15, 18, 20, and 28 showed IC50 value between 0.13 and 1.0 μM; examples 14, 17, 19, 21, 22, and 23 showed IC50 values greater than 1.0 μM and 20.0 μM.

Patchliner Electrophysiological In-Vitro Assay

The recording of sodium current from stable HEK293 cell lines expressing NaV1.7 or NaV1.5 was done on a Patchliner® instrument, Nanion Technologies. The Patchliner® is a fully automated bench-top patch clamp platform and can record simultaneously from up to eight single cells with GΩ seals.

For patch-clamp experiments, cells were grown under standard culturing conditions in Dulbecco's Modified Eagles medium supplemented with 10% fetal bovine serum, glutamine and HEPES. Cells were harvested and kept in suspension for up to 4 hours with no significant change in quality or ability to patch. Whole cell patch clamp recordings were conducted according to Nanion's standard procedure for the Patchliner®. Experiments were conducted at room temperature.

Voltage protocols were designed to establish: 1) peak current amplitude (Imax), 2) test potential (Vmax) and 3) half-inactivation potential (V½) for each of the eight individual cells. To determine V½, a standard steady-state inactivation protocol was executed using a series of fifteen 500 ms depolarizing pre-pulses in 10 mV increments (starting at −130 mV) and immediately followed by a 10 ms test pulse to Vmax. To estimate test compound affinity to the inactivated state of sodium channel (Ki), the holding potential for each cell was set automatically to the V½ calculated from a steady-state inactivation data. The current was activated with the following voltage protocol: holding at V½ for 2-5 seconds, return to the −120 mV for 5-10 ms to relieve fast inactivation, stepping to test potential (Vmax) for 10-20 ms. This voltage protocol was repeated every 10 seconds to establish the baseline with 2-3 buffer additions followed by the test compound addition. The dose-dependent inhibition was analyzed using Nanion's Data Analysis Package.

Examples 1, 2, 5, 6, 8, 11, 12, 13, 15, 16, 20, 24, 26, 28, 29 and 32 showed IC50 values less than 0.1 μM; examples 14, 17, 18, 19, 21, 22, 23, 25 and 33 showed IC50 value between 0.1 and 1.0 μM.

In-Vitro Cytochrome P450 (CYP450) Assay for Measuring Drug Metabolism

We evaluated interaction of drug candidates with cytochrome P450 enzymes which are a major determinant of drug clearance via oxidative metabolism using a high throughput compatible, fluorescence based CYP450 screening assay (Vivid® CYP450, Invitrogen) according to manufacturer's directions. In brief, test compounds at four different concentrations (μM—6.0, 2.0, 0.7, 0.2), a positive control (Ketoconazole) and a solvent control were incubated at room temperature in unique wells of a 96-well microtiter plate with CYP3A4 enzyme complex for 20 minutes. A pre-read fluorescence (Ex-485 nm/Em-530 nm) was measured at the start of the incubation using a Tecan Safire$^2$ microplate reader-monochromator to determine background fluorescence. At the end of the incubation period, enzyme substrate and co-enzyme were added and the reaction was kinetically monitored for 1 hour by measuring fluorescence every minute. Effect of test compounds on inhibition of CYP3A4 metabolism of provided substrate was determined by calculating the ratio of the effective reaction rate in presence of test compound to that in the absence of inhibitor.

Examples 9, 11, 13, 14, 15, 17, 18, 19, 21, and 22 showed 0-25% CYP3A4 inhibition at 6 μM test concentration; examples 5, 6, 8, 10 and 16 showed 25-50% CYP3A4 inhibition at 6 μM test concentration; examples 1, 2, 3, 4, 12, 20 and 32 showed 50-100% CYP3A4 inhibition at 6 μM test concentration.

5.1.2 In Vivo Assays

Method for Formalin Test

The Formalin Test (pain behaviors) produces two phases of response, phase 1 (0 to 10 minutes post-formalin injection) is related to direct damage on nociceptors at the sensory nerve endings and mimics post-surgical pain and wound pain, while phase 2 (11 to 40 minutes post-formalin injection) is related to neuro-inflammation pain which mimics inflammatory arthritis (joint pain).

Each animal is acclimatized for 2-3 days prior to tests. Following acclimatization, a test compound, a positive control, such as mexiletine or lidocaine, which are well-known to inhibit pain, or a vehicle control, such as saline, is administered by intraperitoneal injection or oral gavage 15-20 minutes prior to administration of formalin. The time of administration of test compound is recorded. Formalin solution (1.25%) in PBS is injected subcutaneously (s.c) in a volume of 50 μL into the dorsum of a hindpaw of each rat at time (T)=0 minutes. Each animal is then placed in a clear observation chamber. Observation is started at T=1 minute to 60 minutes post-injection. The number of flinches (licking, biting, or shaking) per minute is recorded for each animal by an automated nociception analyzer. This is accomplished by measuring the movement of a small metal band (0.5 grams) that is placed on the ankle near the injected paw 15-30 minutes before administration of the test compound. Formalin is injected into the paw with the band and the animal is then placed without restraint inside the observation chamber over an electromagnetic detector system. The paw flinches are detected by the system and counted automatically using a computer. At the end of the test, a file is written that contains identifying information for each animal and the number of flinches per minute over time. The Foot fault test is conducted 75 minutes post-dosing. Other observations of changes in movement such as immobility and seizure are recorded during the whole study period. At the end of study, the animals are euthanized.

Examples 1, 2, 6, 8 and 12 showed reduction in pain response of 24-78% (formalin assay, phase 1) and 29-73% (formalin assay phase 2) relative to vehicle control at doses of 3 to 30 mg/kg via the intraperitoneal route.

Example 1 showed reduction in pain response of 14% (formalin assay, phase 1) and 17% (formalin assay phase 2) relative to vehicle control at a dose of 75 mg/kg via the oral route.

Example 12 showed reduction in pain response of 13-24% (formalin assay, phase 1) and 29-43% (formalin assay phase 2) relative to vehicle control at a dose of 1504 of 1 or 2% w/v solution via the topical route.

Method of Partial Sciatic Nerve Ligation (PSNL)

The Partial Sciatic Nerve Ligation Model is associated with neuropathic pain such as spinal disc bulge and diabetic nerve damage.

250-350 g male Sprague-Dawley rats from appropriate animal resources are anesthetized with 2.5% isoflurane. A hind leg is shaved, and the skin is sterilized with 0.5% iodine and 75% alcohol. All surgical instruments are sterilized before surgery and between animals. An incision (1 cm) is made at the middle of the thigh in parallel with the muscle and sciatic nerve distribution. The muscle is exposed and dissected at the joint of two muscles (biceps femoris) indicated by the light colored (white) fascia line. The sciatic nerve is just beneath the muscle and is hooked out using an 18-20G feeding needle (90 degree curved); the sciatic nerve is flat on the feeding needle and approximately one-half the diameter of the nerve is tightly ligated with 7-0 silk suture. A response of the injured leg twitch indicates the success of ligation. After checking hemostasis, bupivicaine 0.1-0.2 ml (0.125%) is given at the incision area, the muscle and the adjacent fascia are closed with 5-0 absorbable sutures. The skin is sutured with absorbable suture and tissue glue. Sham surgery animals (about 8-10 animals) undergo the same surgical procedure but with no ligation. Animals are returned to their home cage after recovery from anesthesia.

The following behavioral tests were conducted started on day 3 and thereafter once weekly following surgery.

Thermal Hyperalgesia:

The plantar test quantitatively assesses the thermal threshold of the hindpaw. Rats are placed on the glass surface of a thermal testing apparatus (Model 336, IITC/Life Science Instruments, Woodland Hills, Calif.) and are allowed to acclimate for 10 min before testing on the glass surface at room temperature. The animals are placed in chambers with the temperature of the glass surface maintained constant at 30-32° C. A mobile radiant heat source located under the glass is focused onto the hindpaw of each rat. The device is set at 55% (heating rate ~3° C. per sec) heating intensity with a cut-off at 10 sec. The paw withdrawal latency was recorded by a digital timer. The thermal threshold is determined as the mean withdrawal latency from two to three consecutive trials of both hindpaws The cutoff of 10 s was used to prevent potential tissue damage.

Mechanical Hyperalgesia

The paw pressure test assesses nociceptive mechanical thresholds, expressed in grams, and is measured with a Ugo Basil Analgesimeter (Varese, Italy). The test is performed by applying a noxious (painful) pressure to the hindpaw. By pressing a pedal that activates a motor, the force is increased (32 g/s) on a linear scale. When the animal displays pain by withdrawal of the paw or vocalization, the pedal is immediately released and the nociceptive pain threshold read on a scale (a cutoff of 150 g is used to avoid tissue injury) (Courteix et al. 1994). Both hindpaws are used for assessment of mechanical hyperalgesia. At least two trials, separated by 10 min, are performed in each rat, and the mean value is used. A testing session for a particular rat begins after 5 min of habituation or as soon as the rat stops exploring and appears acclimatized to the testing environment.

Tactile Allodynia

The Von Frey test quantifies mechanical sensitivity of the hindpaw, The test utilizes a non-noxious stimulus, and is therefore considered to measure tactile allodynia. Animals are placed under clear plastic boxes above a wire mesh floor, which allowed full access to the paws. Behavioral acclimation is allowed for at least 5 min. Mechanical paw withdrawal thresholds (PWTs) are measured with the up-down testing paradigm. Von Frey filaments in log increments of force (2.0, 4.0, 6.0, 8.0, 10.0, 15.0, 26, 60 g or size 4.31, 4.56, 4.74, 4.93, 5.07, 5.18, 5.46, 5.88) are applied for a duration of 2-3 s to the mid-plantar paw in neuropathic pain (i.e. PSNL) animals. Application is to the central region of the plantar surface avoiding the foot pads. The 4.0-g stimulus is applied first. Whenever a withdrawal response to a given probe occurs, the next smaller von Frey probe is applied. Whenever a negative response occurs, the next higher von Frey probe is applied. The test continued until (1) the responses of four more stimuli (total 3-5 trials) after the first change in response has been obtained or (2) the upper/lower end of the von Frey hair is reached (bending). If the animal shows no response to any of the von Frey hairs, a value of 26 g, corresponding to the next log increment in potential von Frey filament, is assigned as the threshold. The testing is continued until the hair with the lowest force to induce a rapid flicking of paw is determined or when the cut off force of approximately 26 g is reached. This cut off force is used because it represent approximately 10% of the animals' body weight and serves to prevent rising of the entire limb due to the use of stiffer hairs, which would change the nature of the stimulus. The value of each hair is confirmed weekly by measuring the magnitude in grams exerted by the hair when applied to an electronic balance. The hair is applied only when the rat is stationary and standing on all four paws. A withdrawal response is considered valid only if the hind paw is completely removed from the platform. Although infrequent, if a rat walks immediately after application of a hair instead of simply lifting the paw, the hair is reapplied. On rare occasions, the hind paw only flinches after a single application; as the hind paw is not lifted from the platform, this is not considered a withdrawal response. A trial consists of application of a von Frey hair to the hind paw five times at 5 s intervals or as soon as the hind paw is placed appropriately on the platform. If withdrawal does not occur during five applications of a particular hair, the next larger hair in the series is applied in a similar manner. When the hind paw is withdrawn from a particular hair either four or five times out of the five applications, the value of that hair in grams is considered to be the withdrawal threshold. Once the threshold is determined for the left hind paw, the same testing procedure is repeated on the right hind paw after 5 min.

Weight Bearing

Rats are tested for hypersensitivity and spontaneous pain in the weight-bearing test, using an Incapacitance tester (Linton Instruments, Norfolk, UK). The rat is placed into the plastic box of the device. The integrated paw pressure during this period (1-2 seconds) is displayed separately for the right and left leg. The ratio between the pressure of the right and left leg is calculated as left/right hind leg weight distribution ratio. The weight bearing assay is repeated 3 times in 5 minutes. The mean distribution ratio of 3 assays is calculated.

Examples 1 and 2 showed recovery of pain response of 49-62% (paw pressure test), 59-73% (plantar test) and 50-66% (weight bearing) relative to vehicle control at a dose of 30 mg/kg via the intraperitoneal route.

Writhing Model

The Acetic Acid Writhing Model is associated with visceral pain (abdominal pain, such as stomach pain, and pain caused by, for example, bile duct congestion and kidney stones).

A writhing test assesses acute peritoneovisceral pain. After acclimation of 2-3 days, a test compound, positive control or vehicle control is administered by intraperitoneal injection (i.p.) or by oral gavage 15-30 minutes prior to administration of acetic acid. The time of administration of test compound is recorded. For mice: 0.6% Acetic acid solution in saline is injected i.p in a volume of 10 ml/kg. For rats: 4% acetic acid in saline is injected i.p in a volume of 2 ml/kg at T=0 minutes. Each animal is placed in a clear plastic cage. At T=5 minutes, the number of writhing movements is counted over a 45 minute period. Alternatively, the writhing movements are counted over a 5-minute period and repeated every 5 minutes, starting at T=5 minutes over a 45-minute period.

Example 2 showed reduction in pain response of 48-58% relative to vehicle control at doses of 10 to 30 mg/kg via the intraperitoneal route.

5.2 Examples of NaV Modulators

5.2.1 General Methods

5.2.1.1 LCMS Method

Method-A

LC-MS was carried out on Acquity H—Class UPLC, PDA and SQ Detector. The column used was BEH C18 50×2.1 mm, 1.7 micron and column flow was 0.55 ml/min. Mobile phase were used (A) 0.1% Formic acid+5 mM Ammonium Acetate in water and (B) 0.1% Formic acid in Acetonitrile. The UV spectra were recorded at its lambda Max and Mass spectra were recorded using ESI technique. The following gradient is used to monitor reaction progress and analyze final products.

| Time (min) | % A | % B |
|---|---|---|
| 0.01 | 95 | 05 |
| 0.40 | 95 | 05 |
| 0.80 | 65 | 35 |
| 1.20 | 45 | 55 |
| 2.50 | 00 | 100 |

-continued

| Time (min) | % A | % B |
|---|---|---|
| 3.30 | 00 | 100 |
| 3.31 | 95 | 05 |
| 4.00 | 95 | 05 |

Method-B

LC-MS was carried out on Waters LC alliance 2995, PDA 2996 and SQ Detector. The column used was X-BRIDGE C18 150×4.6 mm×5 micron and column flow was 1.0 ml/min. Mobile phase were used (A) 0.1% Ammonia in water and (B) 0.1% Ammonia in Acetonitrile. The UV spectra were recorded at its lambda Max and Mass spectra were recorded using ESI technique. The following gradient is used to monitor reaction progress and analyze final products.

| Time (min) | % A | % B |
|---|---|---|
| 0.01 | 90 | 10 |
| 5.00 | 10 | 90 |
| 7.00 | 00 | 100 |
| 11.00 | 00 | 100 |
| 11.01 | 90 | 10 |
| 12.00 | 90 | 10 |

Method-C

LC-MS was carried out on Waters LC alliance 2995, PDA 2996 and SQ Detector. The column used was X-BRIDGE C18 150×4.6 mm×5 micron and column flow was 1.0 ml/min. Mobile phase were used (A) 0.1% Ammonia in water and (B) 0.1% Ammonia in Acetonitrile. The UV spectra were recorded at its lambda Max and Mass spectra were recorded using ESI technique. The following gradient is used to monitor reaction progress and analyze final products.

| Time (min) | % A | % B |
|---|---|---|
| 0.01 | 100 | 00 |
| 7.00 | 50 | 50 |
| 9.00 | 00 | 100 |
| 11.00 | 00 | 100 |
| 11.01 | 100 | 00 |
| 12.00 | 100 | 00 |

Method-D

LC-MS was carried out on Waters LC alliance 2995, PDA 2996 and SQ Detector. The column used was X-BRIDGE C18 150×4.6 mm×5 micron and column flow was 1.0 ml/min. Mobile phase were used (A) 20 mM Ammonium Acetate in water and (B) 100% Methanol. The UV spectra were recorded at its lambda Max and Mass spectra were recorded using ESI technique. The following gradient is used to monitor reaction progress and analyze final products.

| Time (min) | % A | % B |
|---|---|---|
| 0.01 | 90 | 10 |
| 5.00 | 10 | 90 |
| 7.00 | 00 | 100 |
| 11.00 | 00 | 100 |
| 11.01 | 90 | 10 |
| 12.00 | 90 | 10 |

5.2.1.2 HPLC Method

Method-A

HPLC was carried out on Waters e2695, PDA Detector. The column used was Phenomenex Gemini, C18 150×4.6 mm, 5 micron and column flow was 1.00 ml/min. Mobile phase were used (A) 0.1% Formic acid in water and (B) 0.1% Formic acid in Acetonitrile. The UV spectra were recorded at its lambda Max. The following gradient is used.

| Time (min) | % A | % B |
|---|---|---|
| 0.01 | 90 | 10 |
| 7.00 | 10 | 90 |
| 9.00 | 00 | 100 |
| 13.00 | 00 | 100 |
| 13.01 | 90 | 10 |
| 17.00 | 90 | 10 |

Method-B

HPLC was carried out on Waters e2695, PDA Detector. The column used was Phenomenex Gemini, C18 150×4.6 mm, 5 micron and column flow was 1.00 ml/min. Mobile phase were used (A) 0.1% Formic acid in water and (B) 0.1% Formic acid in Acetonitrile. The UV spectra were recorded at its lambda Max. The following gradient is used.

| Time (min) | % A | % B |
|---|---|---|
| 0.01 | 100 | 00 |
| 7.00 | 50 | 50 |
| 9.00 | 00 | 100 |
| 13.00 | 00 | 100 |
| 13.01 | 100 | 00 |
| 17.00 | 100 | 00 |

Method-C

HPLC was carried out on Waters e2695, PDA Detector. The column used was X-BRIDGE, C18 150×4.6 mm, 5 micron and column flow was 1.00 ml/min. Mobile phase were used (A) 0.1% Ammonia in water and (B) 0.1% Ammonia in Acetonitrile. The UV spectra were recorded at its lambda Max. The following gradient is used.

| Time (min) | % A | % B |
|---|---|---|
| 0.01 | 90 | 10 |
| 7.00 | 10 | 90 |
| 9.00 | 00 | 100 |
| 13.00 | 00 | 100 |
| 13.01 | 90 | 10 |
| 17.00 | 90 | 10 |

Method-D

HPLC was carried out on Waters e2695, PDA Detector. The column used was X-BRIDGE, C18 150×4.6 mm, 5 micron and column flow was 1.00 ml/min. Mobile phase were used (A) 0.1% Ammonia in water and (B) 0.1% Ammonia in Acetonitrile. The UV spectra were recorded at its lambda Max. The following gradient is used.

| Time (min) | % A | % B |
|---|---|---|
| 0.01 | 100 | 00 |
| 7.00 | 50 | 50 |
| 9.00 | 00 | 100 |

-continued

| Time (min) | % A | % B |
|---|---|---|
| 13.00 | 00 | 100 |
| 13.01 | 100 | 00 |
| 17.00 | 100 | 00 |

5.2.1.3 PREP HPLC Method

Method-A

PREP HPLC was carried out on Shimadzu UFLC, LC-20 AP, and UV Detector. The column used was Sunfire OBD, C18 250×19 mm, 5 micron and column flow was 18.00 ml/min. Mobile phase were used (A) 0.1% HCL in water and (B) 100% Acetonitrile. The UV spectra were recorded at its lambda Max. The following gradient was used.

| Time (min) | % A | % B |
|---|---|---|
| 0.01 | 90 | 10 |
| 7.00 | 10 | 90 |
| 9.00 | 00 | 100 |
| 13.00 | 00 | 100 |
| 13.01 | 90 | 10 |
| 17.00 | 90 | 10 |

Method-B

PREP HPLC was carried out on Shimadzu UFLC, LC-20 AP, and UV Detector. The column used was Sunfire OBD, C18 250×19 mm, 5 micron and column flow was 18.00 ml/min. Mobile phase were used (A) 0.1% Formic acid in water and (B) 0.1% Formic acid in Acetonitrile. The UV spectra were recorded at its lambda Max. The following gradient was used.

| Time (min) | % A | % B |
|---|---|---|
| 0.01 | 90 | 10 |
| 7.00 | 10 | 90 |
| 9.00 | 00 | 100 |
| 13.00 | 00 | 100 |
| 13.01 | 90 | 10 |
| 17.00 | 90 | 10 |

Method-C

PREP HPLC was carried out on Shimadzu UFLC, LC-20 AP, and UV Detector. The column used was X-BRIDGE, C18 250×19 mm, 5 micron and column flow was 18.00 ml/min. Mobile phase were used (A) 0.1% Ammonia in water and (B) 0.1% Ammonia in Acetonitrile. The UV spectra were recorded at its lambda Max. The following gradient was used.

| Time (min) | % A | % B |
|---|---|---|
| 0.01 | 90 | 10 |
| 7.00 | 10 | 90 |
| 9.00 | 00 | 100 |
| 13.00 | 00 | 100 |
| 13.01 | 90 | 10 |
| 17.00 | 90 | 10 |

5.2.1.4 List of Abbreviations

Ac=Acetyl
EtOAc=ethyl acetate
Bn=Benzyl
Boc=tert-Butoxycarbonyl
Bzl=Benzyl
DBU=1,8-Diazabyciclo[5.4.0]undec-7-ene
DCC=1,3-Dicyclohexylcarbodiimide
DCM=Dichloromethane
DEAD=Diethyl azodicarboxylate
DIC=Diisopropylcarbodiimide
DIPEA=Diisopropylethylamine
D. M. water=demineralized water
DME=1,2-Dimethoxyethane
DMF=N,N-Dimethylformamide
DMSO=Dimethylsulphoxide
EDC=1-Ethyl-3-(3-dimethylaminopropy)carbodiimide hydrochloride
$Et_2O$=Diethyl ether
HOBt=1-Hydroxybenzotriazole
IPA=Isopropyl alcohol
KHMDS=Potassium bis(trimethylsilyl)amide
LAH=Lithium aluminium hydride
LDA=Lithium diisopropylamide
LHMDS=Lithium bis(trimethylsilyl)amide
MOM=Methoxymethyl
NaHMDS=Sodium bis(trimethylsilyl)amide
NBS=N-Bromosuccinimide
Ph=Phenyl
PMB=p-Methoxybenzyl
Py=Pyridine
TEA=Triethylamine
TFA=Trifluoroacetic acid
THF=Tetrahydrofurane
Tol=p-Toluyl 5.2.2 Examples Example 1: Synthesis of 3-(4-(2-(4-(N-1,2,4-thiadiazol-5-ylsulfamoyl)-2-chloro-5-fluorophenoxy)-5-chlorophenyl)picolinamido)propanoicacid Scheme 5

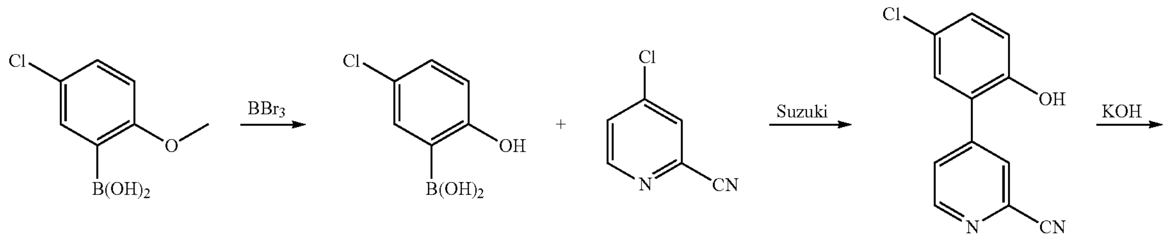

-continued

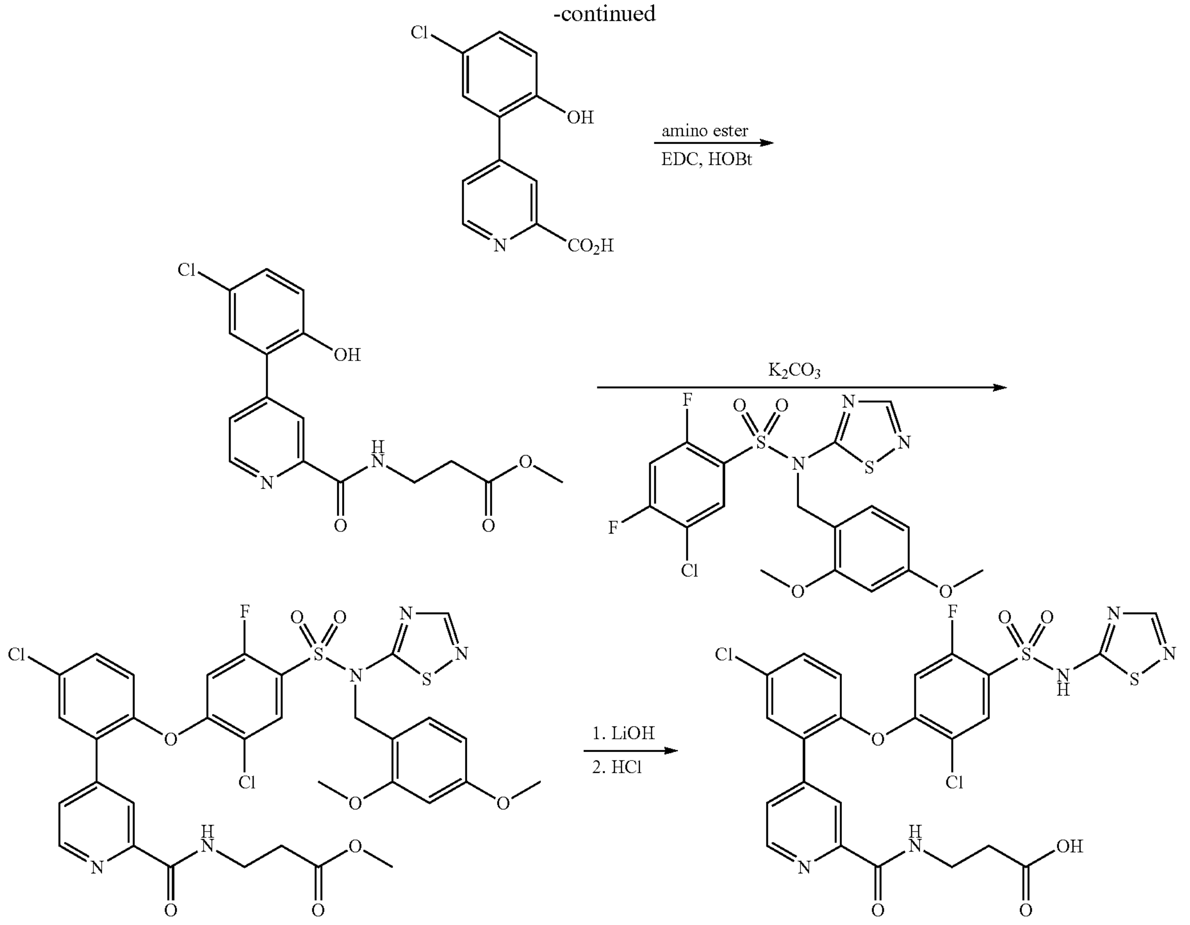

1

Step 1: Preparation of (5-chloro-2-hydroxyphenyl)boronic Acid

A solution of 5-chloro-2-methoxyphenylboronic acid (10.0 g, 53.6 mmol) in dichloromethan (100 ml) was cooled to temperature between 5-10° C. To the above mixture, 100 ml 1M solution of borontribromide in DCM was added drop wise using a pressure equalizing dropping funnel, over a period of 30 minutes. The resulting reaction mixture was then stirred room temperature for 30 minutes. After completion of reaction, the mixture was poured drop wise on to an ice cold saturated sodium bicarbonate solution (600 ml). The resulting mixture was allowed to stir at room temperature for 1 hr. The DCM layer was separated out and the aqueous layer thus collected was cooled to temperature between 10-15° C. 1N solution of dilute hydrochloric acid was then added to the above cooled aqueous layer and this resulted in precipitate formation. The solid was filtered off under vacuo and dried to afford 9 g (yield: 97%) of product. LC-MS: m/z=170.9 (M+H).

Step 2: Preparation of 4-(5-chloro-2-hydroxyphenyl)picolinonitrile

To a solution of 4-Chloropicolinonitrile (1.0 g, 7.2 mmol) in IPA:toluene (7 ml:7 ml) were sequentially added (5-chloro-2-hydroxyphenyl)boronic acid (1.49 g, 8.65 mmol) and potassium carbonate (3.99 g, 21.64 mmol) at room temperature. The resulting reaction mixture was degassed for 15 minutes by purging with nitrogen. Thereafter calculated quantity of Tetrakis (0.416 g, 0.36 mmol) was added to the reaction mixture, nitrogen purging was further continued for next 20 minutes. The resulting reaction mixture was then refluxed at 100° C. for 20 hours. After completion of the reaction, the mixture was concentrated under vacuo. To the resulting crude mass water (50 ml) was added and the mixture was extracted with ethyl acetate (3x25 ml). The combined organic extract was washed with water (20 ml), brine (20 ml), dried over sodium sulfate and concentrated under vacuo to get the desired crude product. The crude product was purified by column chromatography using normal phase silica gel. The desired product eluted at around 20-30% ethyl acetate in hexane. Evaporation of the product fractions gave 0.8 g (yield, 48%) of desired product as a solid. LC-MS: m/z=231.1 (M+H).

Step 3: Preparation of 4-(5-chloro-2-hydroxyphenyl)picolinic Acid)

To a solution of 4-(5-chloro-2-hydroxyphenyl)picolinonitrile (0.5 g, 2.17 mmol) in THF (20 ml) was added a solution of potassium hydroxide (4.276 g, 14 mmol) in water (10 ml) solution at room temperature. The resulting reaction mixture was then refluxed at 100° C. for 5 hours. After completion of the reaction, the mixture was concentrated under vacuo. Ice cold water was added in to the reaction mixture, the resulting mixture was then acidified between pH 3-6 with 1N HCl. The resulting solid precipitate was filtered and dried to afford 0.5 g (yield, 93%) of product as a solid. LC-MS: m/z=249.8 (M+H).

Step 4: Preparation of methyl 3-(4-(5-chloro-2-hydroxyphenyl)-picolinamido)propanoate)

To a solution of 4-(5-chloro-2-hydroxyphenyl)picolinic acid (0.6 g, 2.40 mmol) in THF (20 ml) was sequentially added EDC (0.69 g, 3.61 mmol) and HOBT (0.49 g, 3.61 mmol) at 0° C. The reaction mixture was stirred at 0° C. for 30 minutes. Beta-alanine methyl ester (0.40 g, 2.88 mol) was added at 0° C. The reaction mixture temperature was then allowed to rise to room temperature and stirred for 20 hours. After completion of reaction, water (50 ml) was added in to the reaction mixture. The resulting mixture was then extracted with ethyl acetate (3×25 ml). The combined organic extract was washed with water (20 ml), brine (20 ml), dried over sodium sulfate and concentrated under vacuo to get the desired crude product. The crude product was purified by column chromatography using normal phase silica gel. The desired product eluted at around 0-5% Methanol in dichloromethane. Evaporation of the product fractions gave 0.72 g (yield: 89%) of desired product. LC-MS: m/z=335.6 (M+H).

Step 5: Synthesis of methyl-3-(4-(5-chloro-2-(2-chloro-4-(N-(2,4-dimethoxybenzyl)-N-(1,2,4-thiadiazol-5-yl)sulfamoyl)-5-fluorophenoxy)phenyl)picolinamido)propanoate)

To a solution of methyl 3-(4-(5-chloro-2-hydroxyphenyl) picolinamido)propanoate) (0.72 g, 2.15 mmol) in DMF (10 ml) was added $K_2CO_3$ (0.59 g, 4.3 mol) in one portion under nitrogen atmosphere at room temperature. The resulting reaction mixture was then allowed to stir at room temperature for 15 minutes. To the above reaction mixture was then added calculated quantity of 5-chloro-N-(2,4-dimethoxybenzyl)-2,4-difluoro-N-(1,2,4-thiadiazol-5-yl)benzenesulfonamide (1.0 g, 2.15 mol). The resulting reaction mixture was further allowed to stir at room temperature for 3 hours. After completion of reaction, water (10 ml) was added and the resulting mixture was extracted with ethyl acetate (3×25 ml). The combined organic extract was washed with water (20 ml), brine (20 ml), dried over sodium sulfate and concentrated under vacuo. The crude product was purified by column chromatography using normal phase silica gel. The desired product eluted at around 20 to 25% ethyl acetate in hexane. Evaporation of the product fractions gave 1.0 g (yield: 60%) of desired product. LC-MS: m/z=776.3 (M+H).

Step 6: Preparation of 3-(4-(5-chloro-2-(2-chloro-4-(N-(2,4-dimethoxybenzyl)-N-(1,2,4-thiadiazol-5-yl) sulfamoyl)-5-fluorophenoxy)phenyl)picolinamido) propanoic Acid)

To the solution of methyl-3-(4-(5-chloro-2-(2-chloro-4-(N-(2,4-dimethoxybenzyl)-N-(1,2,4-thiadiazol-5-yl)sulfamoyl)-5-fluorophenoxy)phenyl)picolinamido)propanoate) (1.0 g, 1.28 mmol) in THF (10 mL) was added a solution of Lithium hydroxide monohydrate (0.27 g, 6.43 mmol) in water (5 ml). The resulting reaction mixture was then allowed to stir at room temperature for 3 hours. After completion of reaction, ice cold water was added in to the reaction mixture, the resulting mixture was acidified between pH 4-6 with 1N HCl. The resulting acidic aqueous was extracted with Ethyl acetate (3×25 ml). The combined organic extract was washed with water (20 ml), brine (20 ml), dried over sodium sulphate and concentrated under vacuo. The crude product was purified by column chromatography using normal phase silica gel. The desired product eluted at around 0 to 5% methanol in dichloromethane. Evaporation of the product fractions gave 1 g (yield: 99%) of desired product. LC-MS: m/z=762.8 (M+H).

Step 7: Preparation of 3-(4-(2-(4-(N-1,2,4-thiadiazol-5-ylsulfamoyl)-2-chloro-5-fluorophenoxy)-5-chlorophenyl)picolinamido)propanoicacid To the solution of 3-(4-(5-chloro-2-(2-chloro-4-(N-(2,4-dimethoxybenzyl)-N-(1,2,4-thiadiazol-5-yl)sulfamoyl)-5-fluorophenoxy)phenyl)picolinamido)propanoic acid) (1.0 g, 1.3 mmol) in DCM (10 ml) was added drop wise 4N solution of hydrochloric acid in ethyl acetate (0.5 ml) at room temperature. The resulting reaction mixture was further stirred at room temperature for 2 hour. After completion of reaction, pentane (20 ml) was added in to the reaction mixture which resulted in precipitation of solid. The solid thus obtained was washed twice with pentane (15 ml) and dried under vacuo. The resulting crude material was further purified by Prep HPLC using 0.1% HCl in water:acetonitrile mobile phase. Evaporation of the pure Prep fractions gave 0.29 g (yield: 34%) of desired product as HCl salt. LC-MS: m/z=612.9 (M+H). 1H NMR (DMSO-d6), δ 9.03 (br, 1H), 8.71 (d, J=4.8 Hz, 1H), 8.51 (s, 1H), 8.20 (s, 1H), 7.88 (d, J=7.2 Hz, 1H), 7.80 (br, 2H), 7.60 (d, J=8.4 Hz, 1H), 7.28 (d, J=8.4 Hz, 1H), 7.22 (d, J=10.8 Hz, 1H), 4.01 (br, 2H).

The following nine compounds were synthesized according to the synthetic scheme described for example 1.

Scheme 6

2

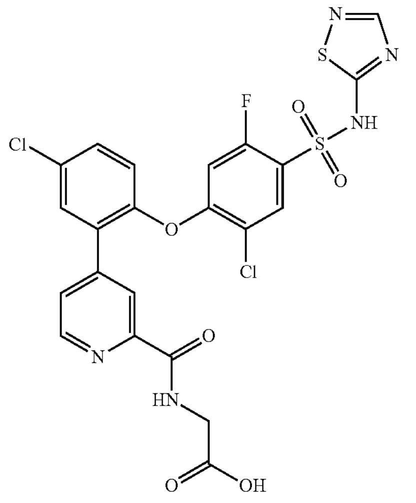

-continued
3
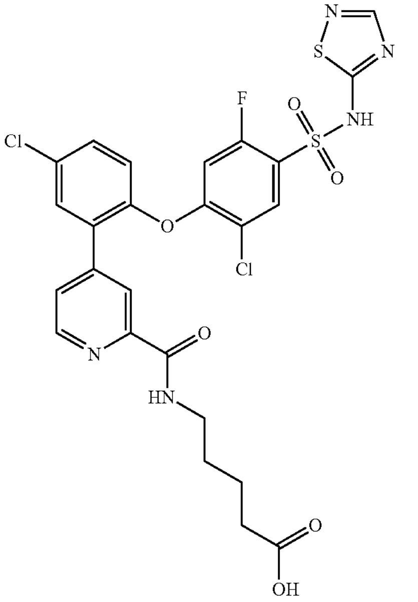
4
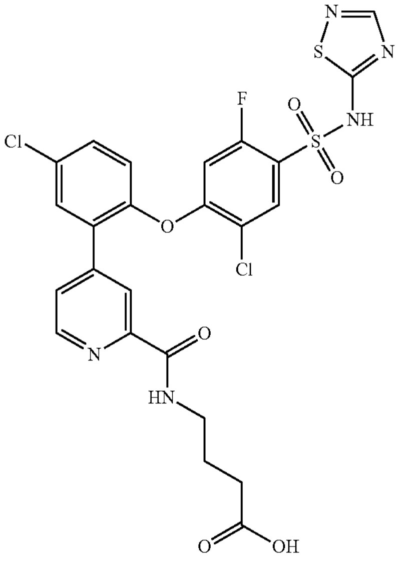
5
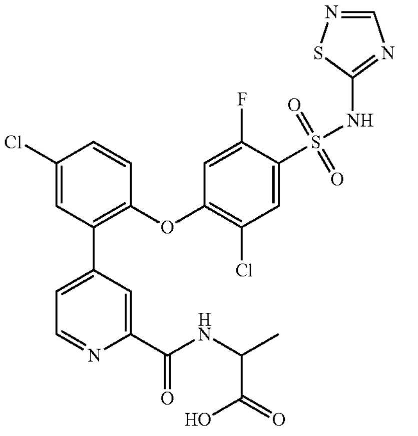
-continued
6
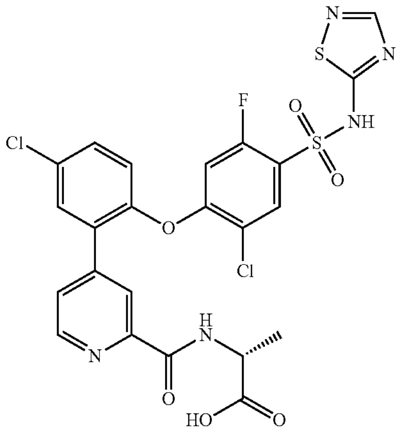
7
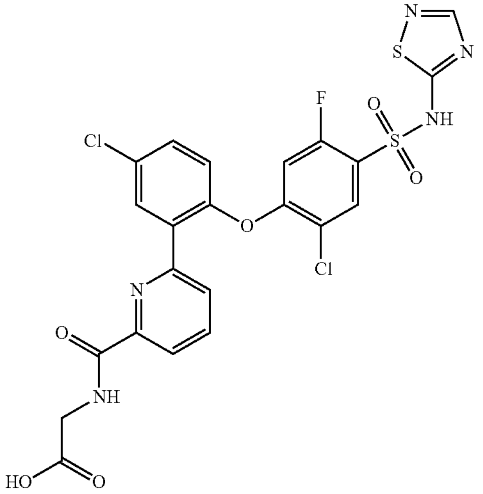
8
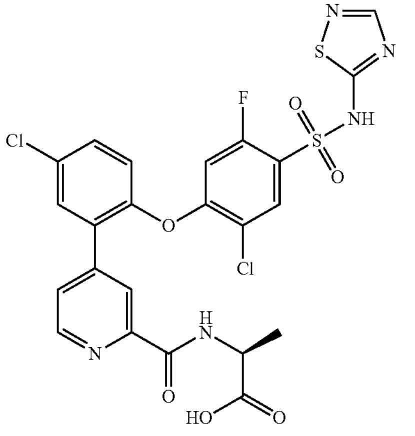

-continued

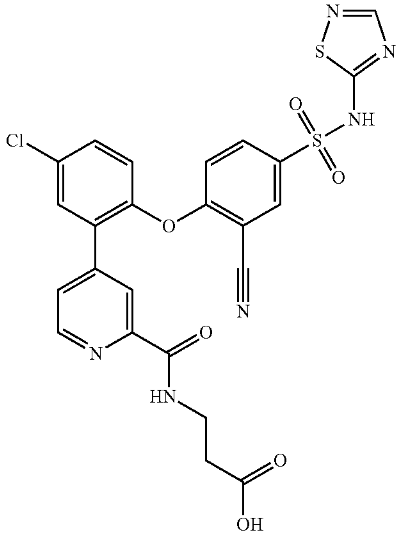

9

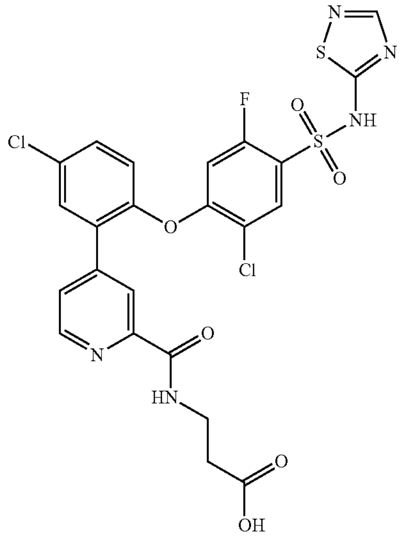

10

Example 2: 2-(4-(2-(4-(N-(1,2,4-thiadiazol-5-yl) sulfamoyl)-2-chloro-5-fluorophenoxy)-5-chlorophenyl)picolinamido)acetic Acid Compound 2 was synthesized according to the procedure described for the synthesis of example 1 by replacing beta-alanine methyl ester with glycine methyl ester hydrochloride in step 4. LC-MS: m/z=598.5 (M+H). 1H NMR (DMSO-d6), δ 9.03 (t, J=6.0 Hz, 1H), 8.71 (d, J=4.8 Hz, 1H), 8.53 (s, 1H), 8.19 (s, 1H), 7.88 (d, J=7.2 Hz, 1H), 7.78-7.81 (m, 2H), 7.60 (dd, J=2.4, 8.8 Hz, 1H), 7.29 (d, J=8.8 Hz, 1H), 7.22 (d, J=10.8 Hz, 1H), 4.00 (br, 2H).

Example 3: 5-(4-(2-(4-(N-(1,2,4-thiadiazol-5-yl) sulfamoyl)-2-chloro-5-fluorophenoxy)-5-chlorophenyl)picolinamido)pentanoic Acid Compound 3 was synthesized according to the procedure described for the synthesis of compound 1 by replacing beta-alanine methyl ester methyl 5-aminopentanoate in step 4. LC-MS: m/z=640.2 (M+H).

Example 4: 4-(4-(2-(4-(N-(1,2,4-thiadiazol-5-yl) sulfamoyl)-2-chloro-5-fluorophenoxy)-5-chlorophenyl)picolinamido)butanoic Acid Compound 4 was synthesized according to the procedure described for the synthesis of compound 1 by replacing beta-alanine methyl ester with methyl 4-aminobutanoate in step 4. LC-MS: m/z=626.6 (M+H). 1H NMR (MeOH-d4), δ 8.65 (d, J=4.8 Hz, 1H), 8.27 (s, 1H), 8.26 (s, 1H), 7.91 (d, J=6.8 Hz, 1H), 7.74 (d, J=4.4 Hz, 1H), 7.71 (d, J=2.4 Hz, 1H), 7.60 (dd, J=2.8, 8.8 Hz, 1H), 7.24 (d, J=8.8 Hz, 1H), 6.94 (s, 1H), 6.78 (d, J=10.8 Hz, 1H), 3.75 (br, 2H), 2.41 (t, J=7.2 Hz, 2H), 1.97 (t, J=7.2 Hz, 2H).

Example 5: (Rac)-2-(4-(2-(4-(N-1,2,4-thiadiazol-5-ylsulfamoyl)-2-chloro-5-fluorophenoxy)-5-chlorophenyl)picolinamido)propanoic Acid Compound 5 was synthesized according to the procedure described for the synthesis of compound 1 by replacing beta-alanine methyl ester with DL-alanine methyl ester hydrochloride in step 4. LC-MS: m/z=613.8 (M+H). 1H NMR (MeOH-d4), δ 8.65 (d, J=5.6 Hz, 1H), 8.27 (s, 1H), 8.25 (s, 1H), 7.90 (d, J=6.8 Hz, 1H), 7.74 (dd, J=1.6, 4.8 Hz, 1H), 7.70 (d, J=2.4 Hz, 1H), 7.59 (dd, J=2.8, 8.8 Hz, 1H), 7.23 (d, J=8.8 Hz, 1H), 6.78 (d, J=10.8 Hz, 1H), 4.63 (q, J=7.2 Hz, 1H), 1.56 (d, J=7.6 Hz, 3H).

Example 6: (R)-2-(4-(2-(4-(N-1,2,4-thiadiazol-5-ylsulfamoyl)-2-chloro-5-fluorophenoxy)-5-chlorophenyl)picolinamido)propanoic Acid Compound 6 was synthesized according to the procedure described for the synthesis of compound 1 by replacing beta-alanine methyl ester with D-alanine methyl ester hydrochloride in step 4. LC-MS: m/z=613.8 (M+H). 1H NMR (MeOH-d4), δ 8.67 (d, J=5.2 Hz, 1H), 8.27 (s, 1H), 8.25 (s, 1H), 7.91 (d, J=7.2 Hz, 1H), 7.75 (dd, J=2.0, 5.2 Hz, 1H), 7.71 (d, J=2.8 Hz, 1H), 7.60 (dd, J=2.4, 8.4 Hz, 1H), 7.24 (d, J=8.8 Hz, 1H), 6.78 (d, J=10.8 Hz, 1H), 4.63 (q, J=7.2 Hz, 1H), 1.56 (d, J=7.6 Hz, 3H).

Example 7: 2-(6-(2-(4-(N-(1,2,4-thiadiazol-5-yl) sulfamoyl)-2-chloro-5-fluorophenoxy)-5-chlorophenyl)picolinamido)acetic Acid Compound 7 was synthesized according to the procedure described for the synthesis of compound 1 by replacing 4-Chloropicolinonitrile with 6-chloropicolinonitrile in step 2. LC-MS: m/z=597.7 (M+H). 1H-NMR (MeOD), δ 8.19 (s, 1H), 8.00-8.07 (m, 4H), 7.9s (d, J=6.8 Hz, 1H), 7.59 (dd, J=2.4, 8.8 Hz, 1H), 7.25 (d, J=8.8 Hz, 1H), 6.72 (d, J=10.4 Hz, 1H), 4.09 (s, 2H).

Example 8: (S)-2-(4-(2-(4-(N-1,2,4-thiadiazol-5-ylsulfamoyl)-2-chloro-5-fluorophenoxy)-5-chlorophenyl)picolinamido)propanoic Acid Compound 8 was synthesized according to the procedure described for the synthesis of compound 1 by replacing beta-alanine methyl ester with L-alanine methyl ester hydrochloride in step 4. LC-MS: m/z=612.6 (M+H). 1H NMR (DMSO-d6), δ 8.85 (d, J=7.6 Hz, 1H), 8.71 (d, J=5.6 Hz, 1H), 8.52 (s, 1H), 8.19 (s, 1H), 7.88 (d, J=7.2 Hz, 1H), 7.78-7.80 (m, 2H), 7.60 (dd, J=2.4, 8.8 Hz, 1H), 7.28 (d, J=8.8 Hz, 1H), 7.22 (d, J=10.8 Hz, 1H), 4.47 (q, J=7.2 Hz, 1H), 1.42 (d, J=7.2 Hz, 3H).

Example 9: 3-(4-(2-(4-(N-(1,2,4-thiadiazol-5-yl) sulfamoyl)-2-cyanophenoxy)-5-chlorophenyl)picolinamido)propanoic Acid Compound 9 was synthesized according to the procedure described for the synthesis of compound 1 by replacing 5-chloro-N-(2,4-dimethoxybenzyl)-2,4-difluoro-N-(1,2,4-thiadiazol-5-yl)benzenesulfonamide with 3-cyano-N-(2,4-dimethoxybenzyl)-4-fluoro-N-(1,2,4-thiadiazol-5-yl)benzenesulfonamide in step 5. LC-MS: m/z=584.8 (M+H). 1H-NMR (MeOD), δ 8.63 (d, J=4.81H), 8.23 (s, 1H), 8.19 (s, 1H), 8.14 (d, J=2.0 Hz, 1H), 7.95 (dd, J=2.4, 8.8 Hz, 1H), 7.74-7.76 (m, 2H), 7.63 (dd, J=2.4, 8.8 Hz, 1H), 6.97 (d, J=10.0 Hz, 1H), 3.68 (t, J=6.8 Hz, 2H), 2.65 (t, J=6.8 Hz, 2H).

Example 10: 3-(4-(2-(4-(N-(1,2,4-thiadiazol-5-yl) sulfamoyl)-2,5-difluorophenoxy)-5-chlorophenyl) picolinamido)propanoic Acid Compound 10 was synthesized according to the procedure described for the synthesis of compound 1 by replacing 5-chloro-N-(2,4-dimethoxybenzyl)-2,4-difluoro-N-(1,2,4-thiadiazol-5-yl)benzenesulfonamide with N-(2,4-dimethoxybenzyl)-2,4,5-trifluoro-N-(1,2,4-thiadiazol-5-yl)benzenesulfonamide in step 5. LC-MS: m/z=595.8 (M+H). 1H-NMR (MeOD), δ 8.66 (d, J=4.81H), 8.28 (s, 1H), 8.26 (s, 1H), 7.69-7.77 (m, 3H), 7.56 (dd, J=2.8, 8.8 Hz, 1H), 6.94 (dd, J=6.4, 10.0 Hz, 1H), 3.70 (t, J=6.4 Hz, 2H), 2.67 (t, J=6.8 Hz, 2H).

Example 11: Preparation of 2-(3-(5-chloro-2-(2-chloro-5-fluoro-4-(N-thiazol-4-ylsulfamoyl)phenoxy)phenyl)propylamino) Acetic Acid Scheme 7

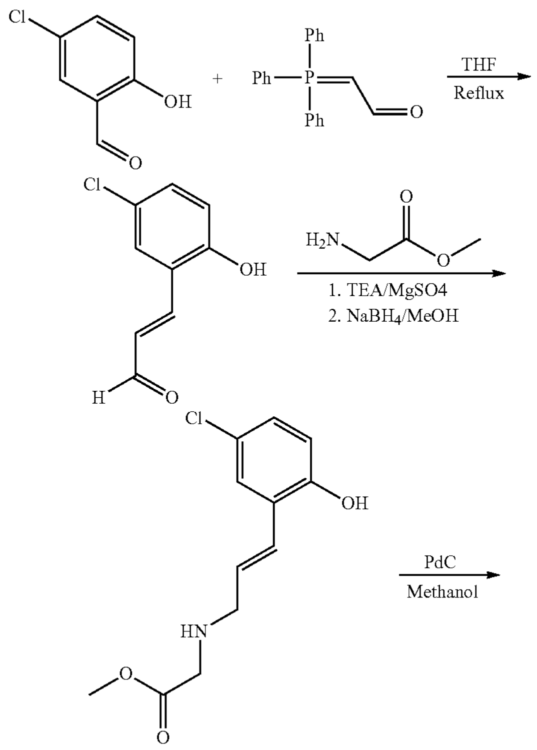

-continued

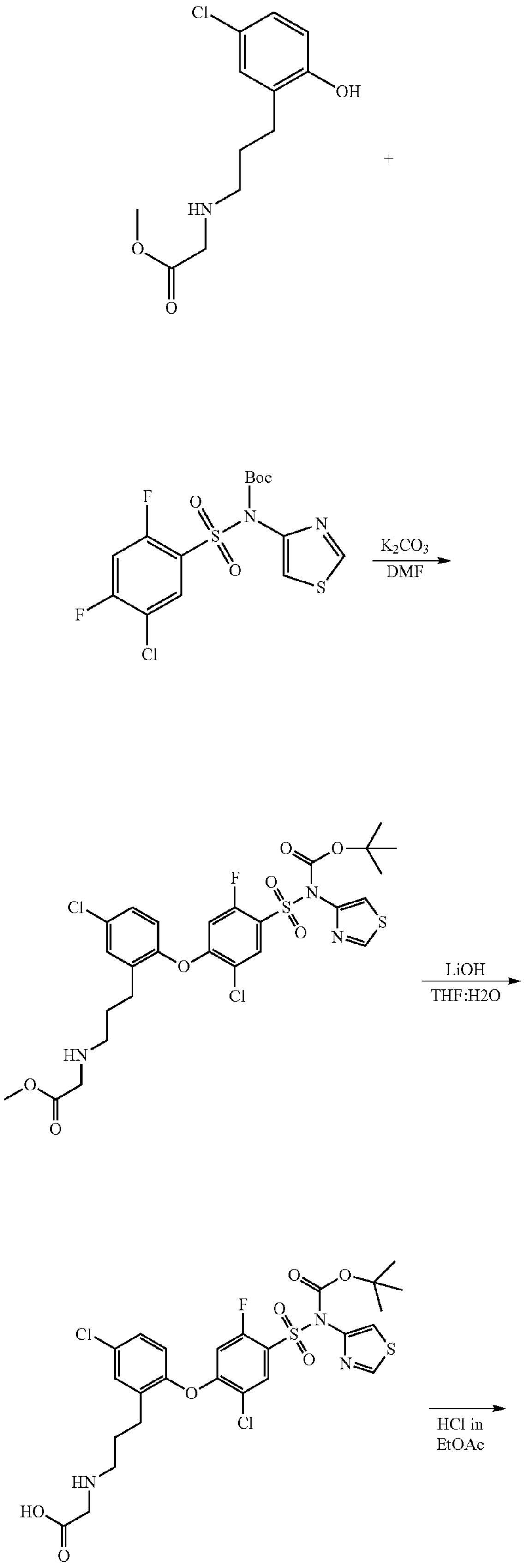

-continued

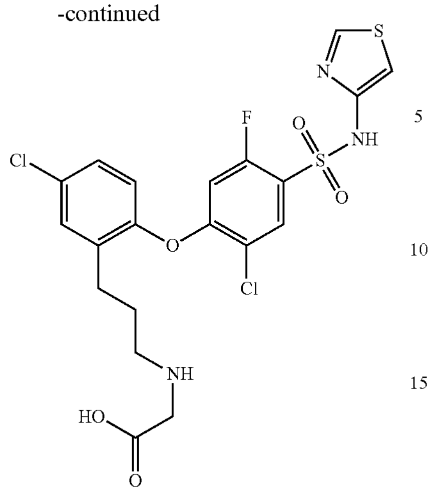

11

Step 1: Preparation of 3-(5-chloro-2-hydroxyphenyl)acrylaldehyde

To a solution of 5-chloro-2-hydroxybenzaldehyde (20 g, 127 mmol) in THF (300 ml) was added (formylmethylene) triphenylphosphorane (43 g, 140 mmol) at room temperature. The resulting reaction mixture was refluxed at 100° C. for 20 hours. The reaction mixture was cooled to room temperature, and extracted with water (200 ml) and ethyl acetate (3×250 ml). The combined organic phase was washed with water (200 ml), brine (200 ml), dried over sodium sulphate and concentrated under vacuo to give the desired crude product. The crude product was purified by column chromatography using normal phase silica gel. The desired product eluted at around 20-30% ethyl acetate in hexane. Evaporation of the product fractions gave 20 g (yield, 87%) of desired compound as yellow solid. LC-MS: m/z=183.4 (M+H).

Step 2: Preparation of methyl 2-(3-(5-chloro-2-hydroxyphenyl) allylamino) Acetate To a solution of 3-(5-chloro-2-hydroxyphenyl)acrylaldehyde (5 g, 27 mmol) and glycine methyl ester hydrochloride (4.1 g, 32 mmol) in dichloromethane (80 ml) was added magnesium sulphate (6 g, 50 mmol) and triethylamine (12 ml, 82 mmol) at room temperature. The above reaction mixture was stirred at room temperature for 18 hours. The resulting reaction mixture was then concentrated under vacuo. The concentrated mass thus obtained was dissolved in methanol (50 ml) and cooled to a temperature between 5-10° C. To the above mixture, sodium borohydride (3.0 g, 82 mmol) was added in small portions over a period of 20 minutes; during addition temperature of the reaction mixture was maintained between 10-20° C. The reaction mixture was allowed to stir at room temperature for 2 hours and concentrated under vacuum. Water (100 ml) was added to the above crude mass and the resulting mixture was extracted with ethyl acetate (3×100 ml). The combined organic extract was washed with water (50 ml), brine (50 ml), dried over sodium sulphate and concentrated under vacuo to get the desired crude product. The crude product was purified by column chromatography using normal phase silica gel. The desired product eluted at around 1-5% methanol in dichloromethane. Evaporation of the product fractions gave 4 g (yield, 58%) of desired compound as yellow solid. LC-MS: m/z=256.43 (M+H).

Step 3: Preparation of methyl 2-(3-(5-chloro-2-hydroxyphenyl)propylamino) Acetate To a solution of methyl 2-(3-(5-chloro-2-hydroxyphenyl) allylamino) acetate (3.5 g, 13.6 mmol) in methanol (80 ml) was carefully added 10% Palladium on carbon with 50% moisture (0.145 g, 1.3 mmol). Hydrogen gas was then bubbled into the reaction mixture at room temperature for a period of 30 minutes. After completion of the reaction, the reaction mixture was filtered through celite. The celite bed was carefully washed with some amount of methanol. The filtrate thus obtained was concentrated under vacuo to afford 3 g (yield, 85%) of compound as colorless liquid and used as is in the next step. LC-MS: m/z=258.5 (M+H).

Step 4: Preparation of methyl 2-(3-(2-(4-(N-(tert-butoxycarbonyl)-N-(thiazol-4-yl)sulfamoyl)-2-chloro-5-fluorophenoxy)-5-chlorophenol)propylamino)acetate To a solution methyl 2-(3-(5-chloro-2-hydroxyphenyl) propylamino) acetate (0.7 g, 2.7 mmol) in DMF (8 ml) was added $K_2CO_3$ (1.2 g, 8.1 mmol) in one portion under nitrogen atmosphere at room temperature. The resulting reaction mixture was then stirred at room temperature for 15 minutes. To the above mixture was added tert-butyl 5-chloro-2,4-difluorophenylsulfonyl(thiazol-4-yl)carbamate (1.22 g, 2.9 mmol) at room temperature and the resulting reaction mixture was stirred at room temperature for 3 hrs. After completion of reaction, water (10 ml) was added and the resulting mixture was extracted with ethyl acetate (3×25 ml). The combined organic extract was washed with water (20 ml), brine (20 ml), dried over sodium sulphate and concentrated under vacuo. The crude product was purified by column chromatography using normal phase silica gel. The desired product eluted at around 20 to 25% Ethyl acetate in Hexane. Evaporation of the product fractions gave 0.6 g (yield, 36%) of desired compound as a solid. LC-MS: m/z=648.4 (M+H).

Step 5: Preparation of 2-(3-(2-(4-(N-(tert-butoxycarbonyl)-N-(thiazol-4-yl)sulfamoyl)-2-chloro-5-fluorophenoxy)-5-chlorophenyl)propylamino)acetic Acid To the solution of methyl 2-(3-(2-(4-(N-(tert-butoxycarbonyl)-N-(thiazol-4-yl) sulfamoyl)-2-chloro-5-fluorophenoxy)-5-chlorophenyl) propylamino) acetate (0.6 g, 0.9 mmol) in THF (10 mL) was added a solution of lithium hydroxide monohydrate (0.0529, 4.6 mmol) in water (6 ml) at room temperature. The resulting reaction mixture was stirred at room temperature for 3 hours. After completion of reaction ice cold water (15 ml) was added in to the reaction mixture, the resulting mixture was then acidified between 4-6 pH with aqueous 1N hydrochloric acid. The resulting acidic aqueous was extracted with ethyl acetate (3×25 ml). The combined organic extract was washed with water (20 ml), brine (20 ml), dried over sodium sulphate and concentrated under vacuo to afford 0.5 g (yield, 85%) of compound as white solid. This material was used in the next step as is.

Step 6: Preparation of 2-(3-(5-chloro-2-(2-chloro-5-fluoro-4-(N-thiazol-4-ylsulfamoyl)phenoxy)phenyl) propylamino) Acetic Acid To the solution of 2-(3-(2-(4-(N-(tert-butoxycarbonyl)-N-(thiazol-4-yl)sulfamoyl)-2-chloro-5-fluorophenoxy)-5-chlorophenyl)propylamino)acetic acid (0.5 g, 0.78 mmol) in dichloromethane (15 ml) was added drop-wise a 4N solution of hydrochloric acid in ethyl acetate (0.5 ml) at room temperature. The resulting reaction mixture was stirred room temperature for 2 hours. After completion of reaction, pentane (20 ml) was added in to the reaction mixture which resulted in precipitation of solid. The solvent layer was decanted off; the solid thus obtained was washed twice with pentane (15 ml) and dried under vacuo. The resulting crude material was further purified by Prep HPLC using 0.1% hydrochloric acid in Water:Acetonitrile mobile phase. Evaporation of the pure product fractions obtained from Prep HPLC provided HCl salt of the desired product (0.16 g, 38% yield). LC-MS: m/z=533.9 (M+H). 1H-NMR (MeOD), δ 8.77 (d, J=2.4 Hz, 1H), 8.03 (d, J=6.8 Hz, 1H), 7.49 (d, J=2.4 Hz, 1H), 7.37 (dd, J=2.8, 8.8 Hz, 1H), 7.12 (d, J=2.4 Hz, 1H), 7.03 (d, J=8.8 Hz, 1H), 6.76 (d, J=10.8 Hz, 1H), 3.8 (s, 2H), 3.09-3.05 (m, 2H), 2.68 (t, J=7.6 Hz, 2H), 2.04-2.01 (m, 2H).

The compounds 12 to 32 were synthesized according to the synthetic scheme described for example 11.

Scheme 8

12

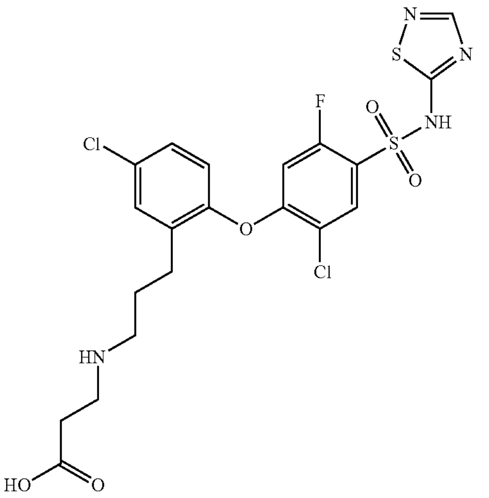

-continued

13

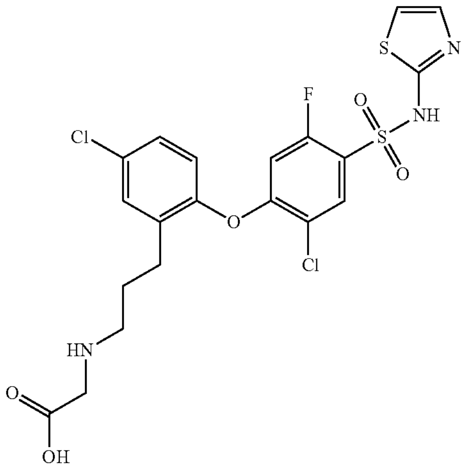

14

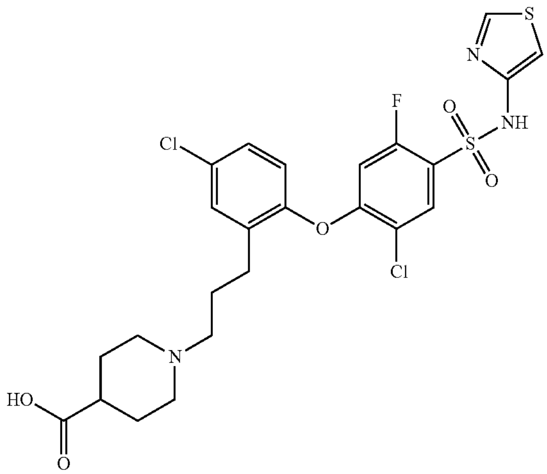

15

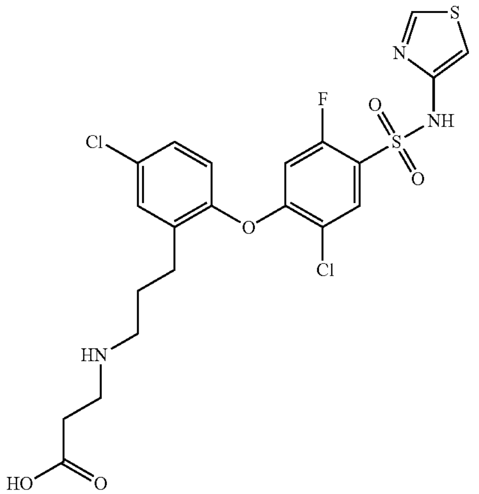

-continued
16
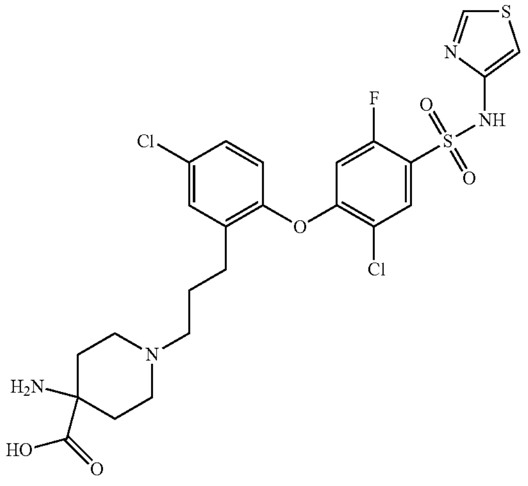
17
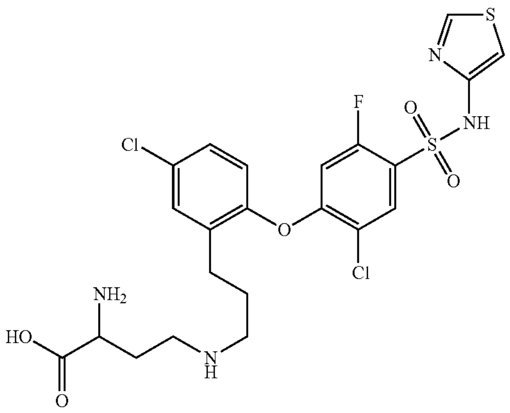
18
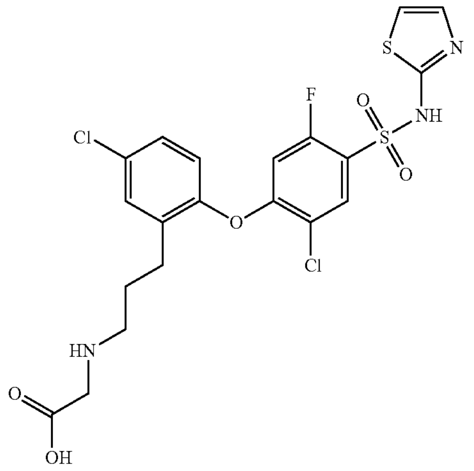
-continued
19
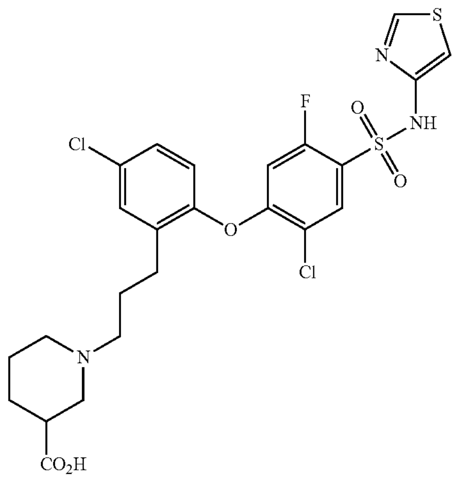
20
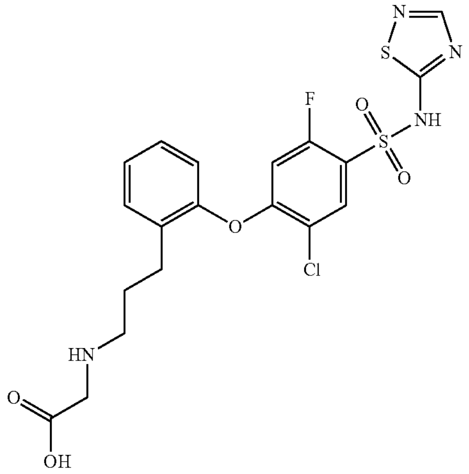
21
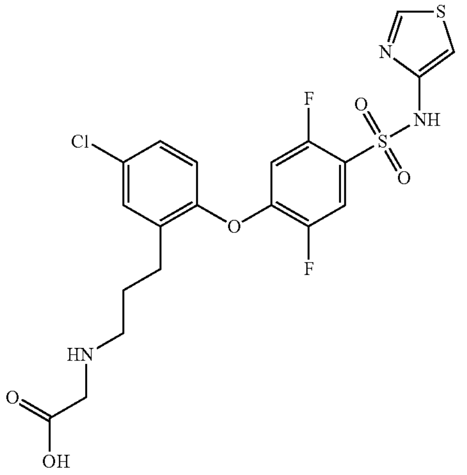

-continued
22
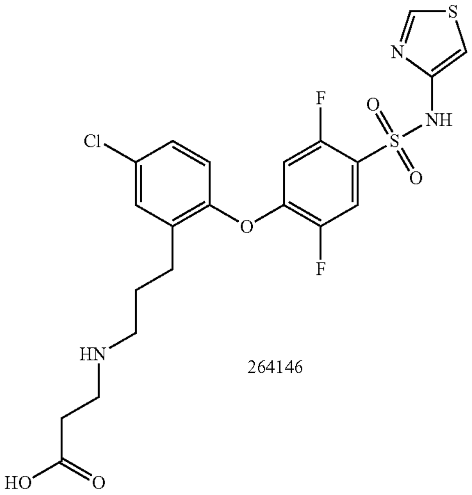
264146
23
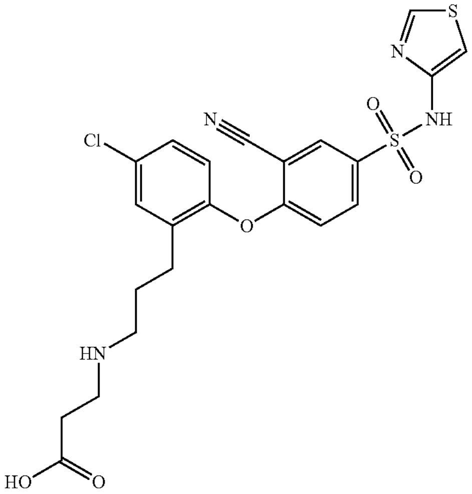
Scheme 9
24
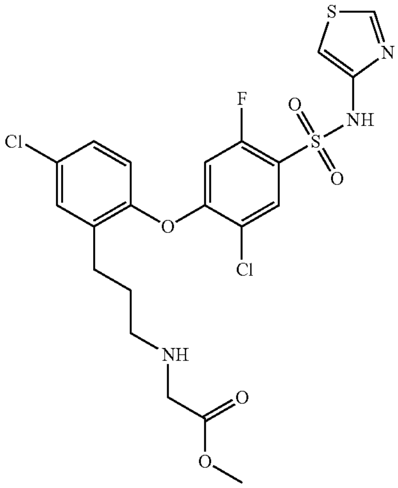
-continued
25
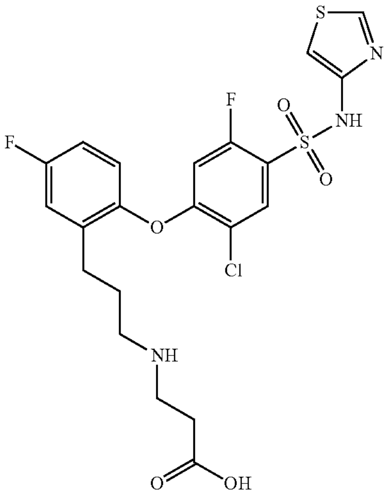
26
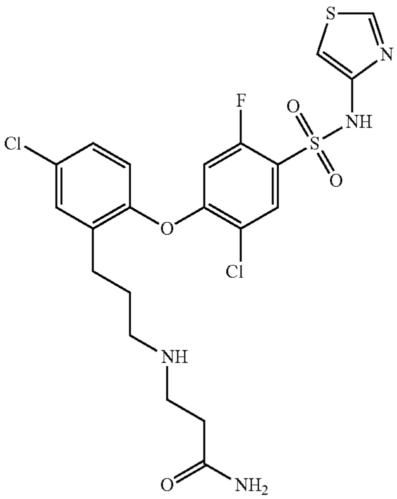
27
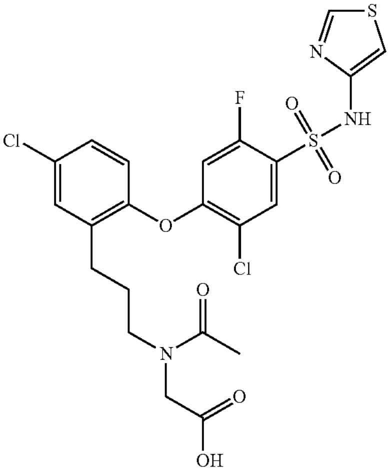

-continued

28

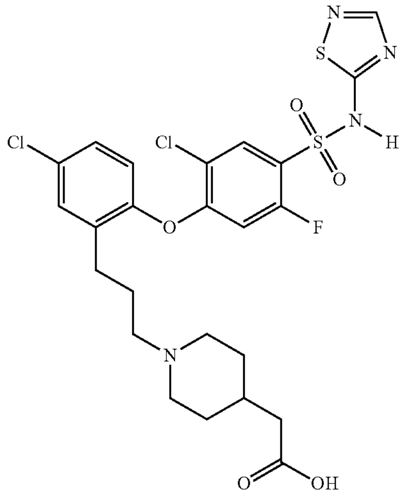

29

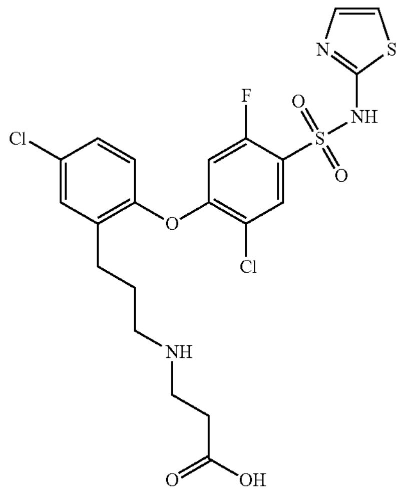

30

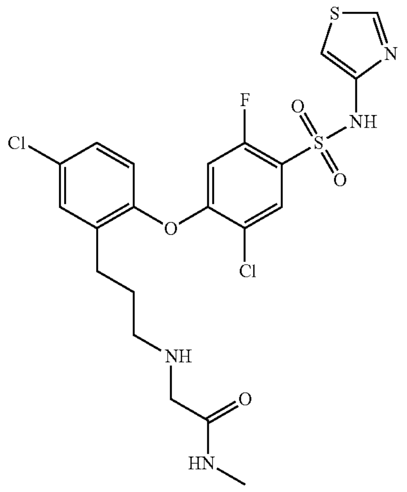

-continued

31

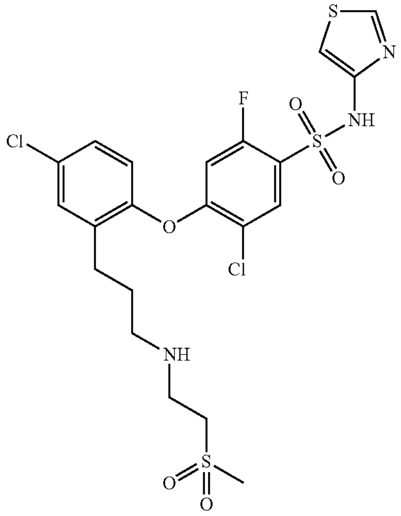

32

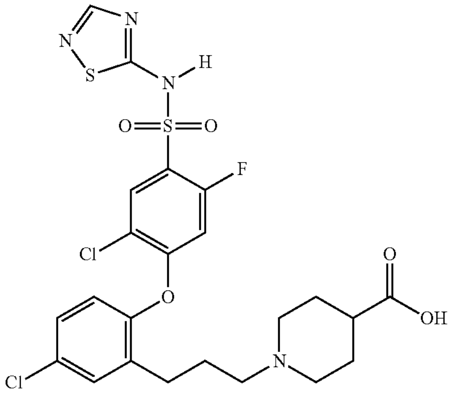

Example 12: 3-((3-(2-(4-(N-(1,2,4-thiadiazol-5-yl)sulfamoyl)-2-chloro-5-fluorophenoxy)-5-chlorophenyl)propyl)amino)propanoic Acid Compound 12 was synthesized according to the procedure described for the synthesis of compound 11 by replacing glycine methyl ester with beta alanine methyl ester in step 2, and replacing tert-butyl 5-chloro-2,4-difluorophenylsulfonyl(thiazol-4-yl)carbamate with 5-chloro-N-(2,4-dimethoxybenzyl)-2,4-difluoro-N-(1,2,4-thiadiazol-5-yl)benzenesulfonamide in step 4. LC-MS: m/z=549.6 (M+H). 1H-NMR (MeOD), δ 8.27 (s, 1H), 8.05 (d, J=7.2 Hz, 1H), 7.49 (d, J=2.4 Hz, 1H), 7.36 (dd, J=2.8, 8.8 Hz, 1H), 7.03 (d, J=8.8 Hz, 1H), 6.78 (d, J=6.4 Hz, 1H), 3.26 (t, J=6.4 Hz, 2H), 3.08 (t, J=7.6 Hz, 2H), 2.68-2.75 (m, 4H), 2.01-2.06 (m, 2H).

Example 13: 2-((3-(5-chloro-2-(2-chloro-5-fluoro-4-(N-(thiazol-2-yl)sulfamoyl)phenoxy)phenyl)propyl)amino)acetic Acid Compound 13 was synthesized according to the procedure described for the synthesis of compound 11 by replacing tert-butyl 5-chloro-2,4-difluorophenylsulfonyl(thiazol-4-yl)carbamate with 5-chloro-N-(2,4-dimethoxybenzyl)-2,4-difluoro-N-(thiazol-2-yl)benzenesulfonamide in step 4. LC-MS: m/z=533.8 (M+H). 1H-NMR (MeOD), δ 7.94 (d, J=6.8 Hz, 1H), 7.52 (d, J=5.8, 1H), 7.35-7.38 (dd, J=2.4, 8.8 Hz, 1H), 7.33 (d, J=4.4 Hz, 1H), 7.11 (d, J=8.8 Hz, 1H), 6.91-6.94 (m, 2H), 3.60 (s, 2H), 2.80 (m, 2H), 2.56 (m, 2H), 1.99 (m, 2H).

Example 14: 1-(3-(5-chloro-2-(2-chloro-5-fluoro-4-(N-(thiazol-4-yl)sulfamoyl)phenoxy)phenyl)propyl) piperidine-4-carboxylic Acid Compound 14 was synthesized according to the procedure described for the synthesis of compound 11 by replacing glycine methyl ester with methyl piperidine-4-carboxylate in step 2. LC-MS: m/z=589.8 (M+H).

Example 15: 3-((3-(5-chloro-2-(2-chloro-5-fluoro-4-(N-(thiazol-4-yl)sulfamoyl)phenoxy)phenyl)propyl) amino)propanoic Acid Compound 15 was synthesized according to the procedure described for the synthesis of compound 11 by replacing glycine methyl ester with beta alanine methyl ester in step 2. LC-MS: m/z=547.8 (M+H). 1H-NMR (MeOD), δ 8.77 (d, J=2.0 Hz, 1H), 8.03 (d, J=10.8 Hz, 1H), 7.49 (d, J=2.4 Hz, 1H), 7.35-7.38 (m, 1H), 7.12 (d, J=2.8 Hz, 1H), 7.03 (d, J=8.4 Hz, 1H), 6.76 (d, J=10.4 Hz, 1H), 3.26 (br, 2H), 3.07 (br, 2H), 2.67-2.76 (m, 4H), 2.02 (br, 2H).

Example 16: 4-amino-1-(3-(5-chloro-2-(2-chloro-5-fluoro-4-(N-(thiazol-4-yl)sulfamoyl)phenoxy)phenyl)propyl)piperidine-4-carboxylic Acid Compound 16 was synthesized according to the procedure described for the synthesis of compound 11 by replacing glycine methyl ester with methyl 4-((tert-butoxycarbonyl) amino)piperidine-4-carboxylate in step 2. LC-MS: m/z=602.8 (M+H). 1H-NMR (MeOD), δ 8.77 (d, J=2.0 Hz, 1H), 8.02 (d, J=7.2 Hz, 1H), 7.52 (d, J=2.8 Hz, 1H), 7.36-7.38 (dd, J=2.8, 8.8 Hz, 1H), 7.12 (d, J=2.0 Hz, 1H), 7.03 (d, J=8.4 Hz, 1H), 6.77 (d, J=10.4 Hz, 1H), 3.25-3.70 (m, 6H) 2.67-2.71 (m, 2H), 2.50 (br, 2H), 2.27 (br, 2H), 2.12 (br, 2H).

Example 17: 2-amino-4-((3-(5-chloro-2-(2-chloro-5-fluoro-4-(N-(thiazol-4-yl)sulfamoyl)phenoxy)phenyl)propyl)amino)butanoic Acid Scheme 10

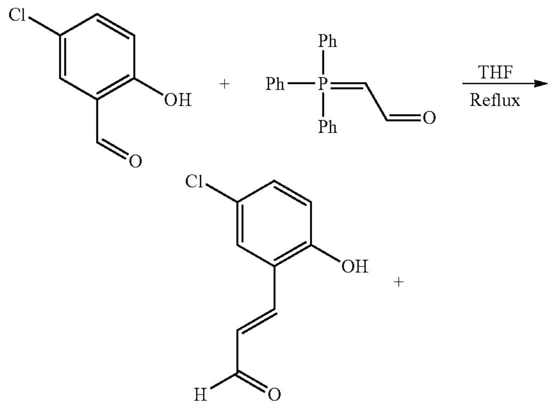

-continued

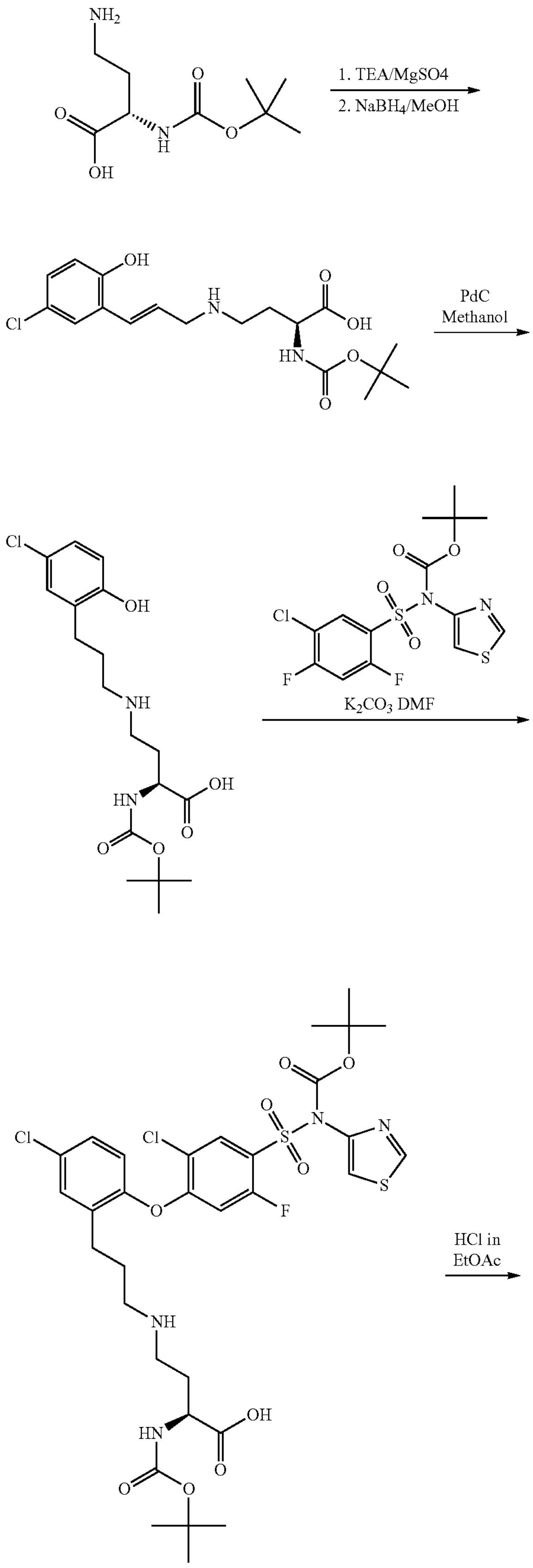

-continued

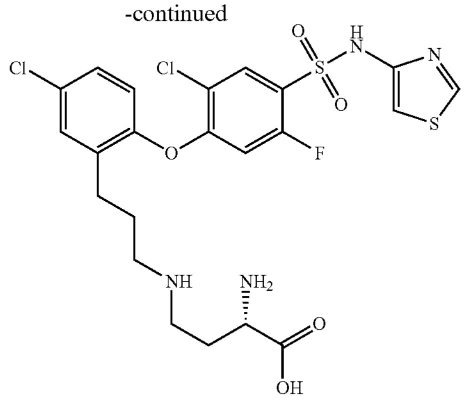

Step 1: Preparation of (S)-4-amino-2-(tert-butoxycarbonylamino)butanoic Acid

To a solution of (S)-5-amino-2-(tert-butoxycarbonylamino)-5-oxopentanoic acid (2 g, 8.1 mmol) in DMF: water (1:1, v/v, 18 ml) was added pyridine (1.3 ml, 16.2 mmol). The resulting reaction mixture was stirred at room temperature for 5-10 minutes. Iodobenzene diacetate (3.92 g, 12.1 mmol) was added and further stirred for 4 hours. After completion of reaction D.M. water (100 ml) was added and the resulting mixture was extracted with ethyl acetate (3×100 ml). The combined organic extracts was washed with D.M. water (100 ml), brine (100 ml), dried over sodium sulphate and concentrated under vacuo to get the desired crude product. The crude product was purified by triturating with diethyl ether. Evaporation of the product fractions gave 1.1 g (yield, 62%) of desired compound as brown solid. LC-MS: m/z=219.1 (M+H).

Step 2: Preparation of (E)-3-(5-chloro-2-hydroxyphenyl)acrylaldehyde

To a solution of 5-chloro-2-hydroxybenzaldehyde (20 g, 127 mmol) in THF (300 ml) was added (Formylmethylene) triphenylphosphorane (43 g, 140 mmol) at room temperature. The resulting reaction mixture was then refluxed at 100° C. for 20 hrs. After completion of reaction, the reaction mixture was allowed to cool to room temperature. D.M. water (200 ml) was added and the resulting mixture was extracted with ethyl acetate (3×250 ml). The combined organic extract was washed with D.M. water (200 ml), brine (200 ml), dried over sodium sulphate and concentrated under vacuo to get the desired crude product. The crude product was purified by column chromatography using normal phase silica gel. The desired product eluted at around 20-30% ethyl acetate in hexane. Evaporation of the product fractions gave 20 g (yield, 87%) of the desired compound as yellow solid. LC-MS: m/z=183.4 (M+H).

Step 3: (S,E)-2-(tert-butoxycarbonylamino)-4-(3-(5-chloro-2-hydroxyphenyl)allylamino)butanoic Acid To a solution of 3-(5-chloro-2-hydroxyphenyl)acrylaldehyde (0.5 g, 3.2 mmol) and (S)-4-amino-2-(tert-butoxycarbonylamino)butanoic acid (0.769 g, 3.52 mmol) in dichloromethane (80 ml) was added magnesium sulphate (0.77 g, 6.4 mmol) and triethylamine (1.34 ml, 9.615 mmol) at room temperature. The above reaction mixture was stirred at room temperature for 12 hours. The resulting reaction mixture was then concentrated under vacuo. The concentrated mass thus obtained was dissolved in methanol (20 ml) and cooled to a temperature between 5-10° C. To the above mixture, sodium borohydride (0.36 g, 9.61 mmol) was added in small portions over a period of 10 minutes, during addition temperature of the reaction mixture was maintained between 10-20° C. After completion of addition, the resulting reaction mixture was allowed to stir at room temperature for 2 hours. After completion of reaction, the reaction mixture was concentrated under vacuo. D.M. water (40 ml) was added to the above crude mass and the resulting mixture was extracted with ethyl acetate (3×60 ml). The combined organic extract was washed with D.M. water (50 ml), brine (50 ml), dried over sodium sulphate and concentrated under vacuo to get the desired crude product. The crude product was purified by column chromatography using normal phase silica gel. The desired product eluted at around 1-5% methanol in dichloromethane. Evaporation of the product fractions gave 0.4 g (yield, 32.5%) of the desired compound as a brown liquid. LC-MS: m/z=385.2 (M+H).

Step 4: (S)-2-(tert-butoxycarbonylamino)-4-(3-(5-chloro-2-hydroxyphenyl)propylamino)butanoic Acid To a solution of (S,E)-2-(tert-butoxycarbonylamino)-4-(3-(5-chloro-2-hydroxyphenyl)allylamino)butanoic acid (0.4 g, 13.6 mmol) in methanol (10 ml) was carefully added 10% Palladium on carbon with 50% moisture (0.120 g, 1.3 mmol). Hydrogen gas was then bubbled into the reaction mixture at room temperature for a period of 15-20 minutes. After completion of the reaction, the reaction mixture was filtered through celite hyflow. The celite bed was carefully washed with some amount of methanol. The filtrate thus obtained was concentrated under vacuo to afford 0.35 g (yield, 87.06%) of the desired compound as a colorless liquid. LC-MS: m/z=387.4 (M+H).

Note: For this particular step, we also observed occurrence of dechlorination, its proportion remained variable. This step was thus monitored cautiously and worked up soon upon completion.

Step 5: (S)-4-(3-(2-(4-(N-(tert-butoxycarbonyl)-N-(thiazol-4-yl)sulfamoyl)-2-chloro-5-fluorophenoxy)-5-chlorophenyl)propylamino)-2-(tert-butoxycarbonylamino)butanoic Acid To a solution (S)-2-(tert-butoxycarbonylamino)-4-(3-(5-chloro-2-hydroxyphenyl)propylamino)butanoic acid (0.350 g, 2.7 mmol) in DMF (0.7 ml) was added $K_2CO_3$ (0.375 g, 2.7 mmol) in one portion under nitrogen atmosphere at room temperature. The resulting reaction mixture was then stirred at room temperature for 15 minutes. To the above mixture was added tert-butyl 5-chloro-2,4-difluorophenylsulfonyl (thiazol-4-yl) carbamate (0.408 g, 0.99 mmol) and the resulting reaction mixture was stirred at room temperature for 3 hours. After completion of reaction, D.M. water (20 ml) was added and the resulting mixture was extracted with ethyl acetate (3×30 ml). The combined organic extract was washed with Ice cold water (100 ml), brine (50 ml), dried over sodium sulphate and concentrated under vacuo. The crude product was purified by column chromatography using normal phase silica gel. The desired product eluted at around 1 to 2% Methanol in DCM. Evaporation of the product fractions gave 0.4 g (yield, 56.8%) of the desired compound as a brown liquid. LC-MS: m/z=777.6 (M+H).

Step 6: Preparation of (S)-2-amino-4-(3-(5-chloro-2-(2-chloro-5-fluoro-4-(N-thiazol-4-ylsulfamoyl)phenoxy)phenyl)propylamino)butanoic Acid To a solution of (S)-4-(3-(2-(4-(N-(tert-butoxycarbonyl)-N-(thiazol-4-yl)sulfamoyl)-2-chloro-5-fluorophenoxy)-5-chlorophenyl)propylamino)-2-(tert-butoxycarbonylamino)butanoic acid (0.4 g, 0.78 mmol) in dichloromethane (10 ml) was added drop-wise a 4N solution of hydrochloric acid in ethyl acetate (2 ml) at room temperature. The resulting reaction mixture was stirred room temperature for 2 hours. After completion of reaction, pentane (20 ml) was added in to the reaction mixture which resulted in precipitation of solid. The solvent layer was decanted off; the solid thus obtained was washed twice with pentane (15 ml) and dried under vacuo. The resulting crude material was further purified by Prep HPLC using 0.1% Formic acid in Water: Acetonitrile mobile phase. Evaporation of the pure product fractions obtained from Prep HPLC provided the desired product as HCl salt (0.0253 g, 8.6% yield). LC-MS: m/z=576.8 (M+H).

Example 18: 2-((3-(5-chloro-2-(2,5-difluoro-4-(N-(thiazol-2-yl)sulfamoyl)phenoxy)phenyl)propyl)amino)acetic Acid Compound 18 was synthesized according to the procedure described for the synthesis of compound 11 by replacing tert-butyl 5-chloro-2,4-difluorophenylsulfonyl(thiazol-4-yl)carbamate with N-(2,4-dimethoxybenzyl)-2,4,5-trifluoro-N-(thiazol-2-yl)benzenesulfonamide in step 4. LC-MS: m/z=517.8 (M+H). 1H-NMR (MeOD), δ 7.81-7.85 (dd, J=6.4, 10.4 Hz, 1H), 7.46 (d, J=6.4, 1H), 7.31-7.34 (dd, J=2.8, 8.8 Hz, 1H), 7.17 (d, J=4.8 Hz, 1H), 6.99 (d, J=8.4 Hz, 1H), 6.86-6.90 (dd, J=6.4, 10.0 Hz, 1H), 6.81 (d, J=4.8 Hz, 1H), 3.92 (s, 2H), 3.08-3.12 (m, 2H), 2.75 (t, J=8.0 Hz, 2H), 2.03-2.08 (m, 2H).

Example 19: 1-(3-(5-chloro-2-(2-chloro-5-fluoro-4-(N-(thiazol-4-yl)sulfamoyl)phenoxy)phenyl)propyl)piperidine-3-carboxylic Acid Compound 19 was synthesized according to the procedure described for the synthesis of compound 11 by replacing glycine methyl ester with methyl piperidine-3-carboxylate in step 2. LC-MS: m/z=589.8 (M+H).

Example 20: 2-((3-(2-(4-(N-(1,2,4-thiadiazol-5-yl)sulfamoyl)-2-chloro-5-fluorophenoxy)phenyl)propyl)amino)acetic Acid Compound 20 was synthesized according to the procedure described for the synthesis of compound 11 by replacing 5-chloro-2-hydroxybenzaldehyde with 2-hydroxybenzaldehyde in step 1. LC-MS: m/z=500.8 (M+H). 1H-NMR (MeOD), δ 8.90 (s, 2H), 8.51 (s, 1H), 7.97 (d, J=7.2 Hz, 1H), 7.41-7.44 (dd, J=1.6, 7.2 Hz, 1H), 7.26-7.34 (m, 2H), 7.07 (dd, J=1.2, 8.0 Hz, 1H), 6.81 (d, J=10.8 Hz, 1H), 3.89 (s, 2H), 2.93 (br, 2H), 2.57-2.61 (m, 2H), 1.92 (br, 2H).

Example 21: 2-((3-(5-chloro-2-(2,5-difluoro-4-(N-(thiazol-4-yl)sulfamoyl)phenoxy)phenyl)propyl)amino)acetic Acid Compound 21 was synthesized according to the procedure described for the synthesis of compound 11 by replacing tert-butyl 5-chloro-2,4-difluorophenylsulfonyl(thiazol-4-yl)carbamate with tert-butyl 2,4,5-trfluorophenylsulfonyl(thiazol-4-yl)carbamate in step 4. LC-MS: m/z=517.8 (M+H). 1H-NMR (MeOD), δ 8.77 (d, J=2.0 Hz, 1H), 7.79-7.83 (dd, J=6.4, 10.0 Hz, 1H), 7.47 (d, J=2.4 Hz, 1H), 7.32-7.35 (dd, J=2.4, 8.4 Hz, 1H), 7.11 (d, J=2.4 Hz, 1H), 7.02 (d, J=8.8 Hz, 1H), 6.85-6.89 (dd, J=6.4, 10.4 Hz, 1H), 3.92 (s, 2H), 3.09-3.16 (m, 2H), 2.73 (t, J=7.6 Hz, 2H), 1.99-2.07 (m, 2H).

Example 22: 3-((3-(5-chloro-2-(2,5-difluoro-4-(N-(thiazol-4-yl)sulfamoyl)phenoxy)phenyl)propyl)amino)propanoic Acid Compound 22 was synthesized according to the procedure described for the synthesis of compound 11 by replacing glycine methyl ester with beta alanine methyl ester in step 2, and replacing tert-butyl 5-chloro-2,4-difluorophenylsulfonyl(thiazol-4-yl)carbamate with tert-butyl 2,4,5-trfluorophenylsulfonyl(thiazol-4-yl)carbamate in step 4. LC-MS: m/z=531.8 (M+H). 1H-NMR (MeOD), δ 8.78 (d, J=2.4 Hz, 1H), 7.79-7.83 (dd, J=6.4, 10.4 Hz, 1H), 7.47 (d, J=2.4 Hz, 1H), 7.32-7.35 (dd, J=2.4, 8.4 Hz, 1H), 7.11 (d, J=2.4 Hz, 1H), 7.01 (d, J=8.8 Hz, 1H), 6.85-6.90 (dd, J=6.4, 10.4 Hz, 1H), 3.27 (t, J=6.8 Hz, 2H), 3.07 (t, J=8.0 Hz, 2H), 2.71-2.78 (m, 4H), 1.97-2.05 (m, 2H).

Example 23: 3-((3-(5-chloro-2-(2-cyano-4-(N-(thiazol-4-yl)sulfamoyl)phenoxy)phenyl)propyl)amino)propanoic Acid Compound 23 was synthesized according to the procedure described for the synthesis of compound 11 by replacing glycine methyl ester with beta alanine methyl ester in step 2, and replacing tert-butyl 5-chloro-2,4-difluorophenylsulfonyl(thiazol-4-yl)carbamate with tert-butyl (3-cyano-4-fluorophenyl)sulfonyl(thiazol-4-yl)carbamate in step 4. LC-MS: m/z=520.9 (M+H). 1H-NMR (MeOD), δ 8.77 (d, J=2.0 Hz, 1H), 8.30 (d, J=2.0 Hz, 1H), 8.03 (dd, J=2.4, 9.2 Hz, 1H), 7.52 (d, J=2.4 Hz, 1H), 7.39 (dd, J=2.8, 8.8 Hz, 1H), 7.16 (d, J=2.0 Hz, 1H), 7.14 (s, 1H), 6.96 (d, J=9.2 Hz, 1H), 3.09 (t, J=6.8 Hz, 2H), 3.09 (t, J=8.0 Hz, 2H), 2.76 (t, J=6.4 Hz, 2H), 2.69 (t, J=8.0 Hz, 2H), 1.99-2.07 (m, 2H).

Example 24: methyl 2-((3-(5-chloro-2-(2-chloro-5-fluoro-4-(N-(thiazol-4-yl)sulfamoyl)phenoxy)phenyl)propyl)amino)acetate Compound 24 was synthesized according to the procedure described for the synthesis of compound 11 without hydrolysis of methyl ester (step 5). LC-MS: m/z=548.4 (M+H). 1H-NMR (MeOD), δ 8.77 (d, J=2.4 Hz, 1H), 8.02 (d, J=6.8 Hz, 1H), 7.49 (d, J=2.4 Hz, 1H), 7.35-7.38 (dd, J=2.4, 8.4 Hz, 1H), 7.12 (d, J=2.4 Hz, 1H), 7.02 (d, J=8.8 Hz, 1H), 6.75 (d, J=10.4 Hz, 1H), 3.99 (s, 2H), 3.85 (s, 3H), 3.08-3.12 (m, 2H), 2.68 (t, J=7.6 Hz, 2H), 2.00-2.08 (m, 2H).

Example 25: 3-((3-(2-(2-chloro-5-fluoro-4-(N-(thiazol-4-yl)sulfamoyl)phenoxy)-5-fluorophenyl)propyl)amino)propanoic Acid Compound 25 was synthesized according to the procedure described for the synthesis of compound 11 by replacing 5-chloro-2-hydroxybenzaldehyde with 5-fluoro-2-hydroxybenzaldehyde in step 1, and replacing glycine methyl ester with beta alanine methyl ester in step 2. LC-MS: m/z=531.9 (M+H). 1H-NMR (MeOD), δ 8.77 (d, J=2.4 Hz, 1H), 8.01 (d, J=6.8 Hz, 1H), 7.23 (dd, J=2.4, 8.8 Hz, 1H), 7.11-7.13

(m, 3H), 6.65 (d, J=10.8 Hz, 1H), 3.25 (t, J=6.8 Hz, 2H), 3.06 (t, J=8.0 Hz, 2H), 2.73 (t, J=6.4 Hz, 2H), 2.66 (t, J=7.6 Hz, 2H), 1.99-2.03 (m, 2H).

Example 26: 3-((3-(5-chloro-2-(2-chloro-5-fluoro-4-(N-(thiazol-4-yl)sulfamoyl)phenoxy)phenyl)propyl)amino)propanamide Scheme 11

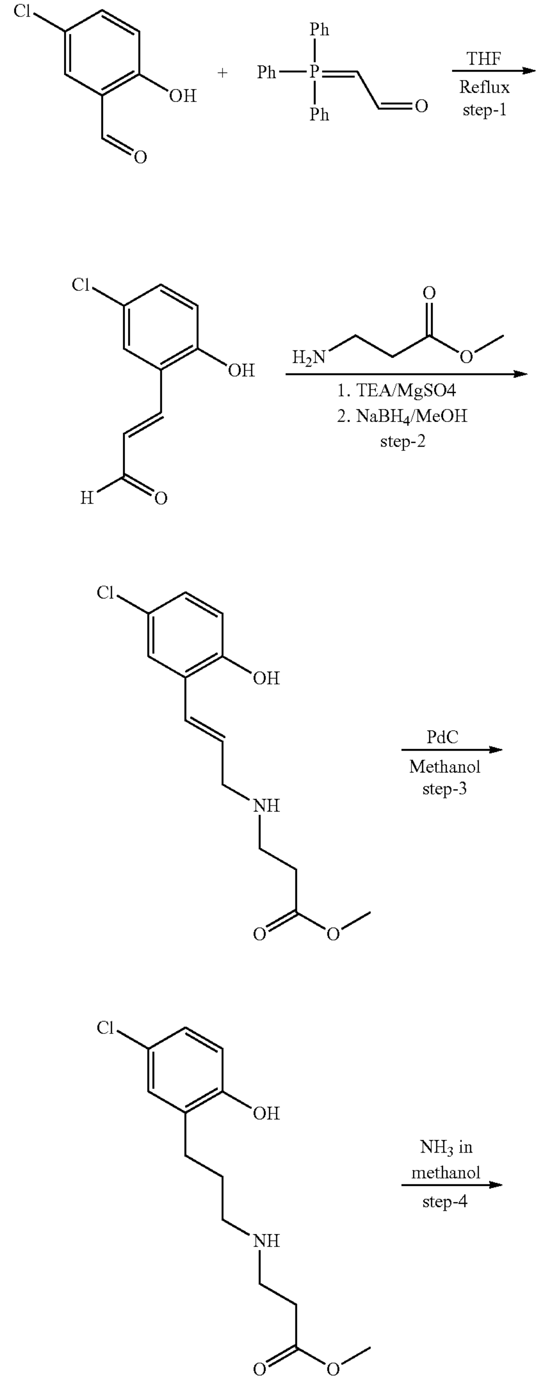

-continued

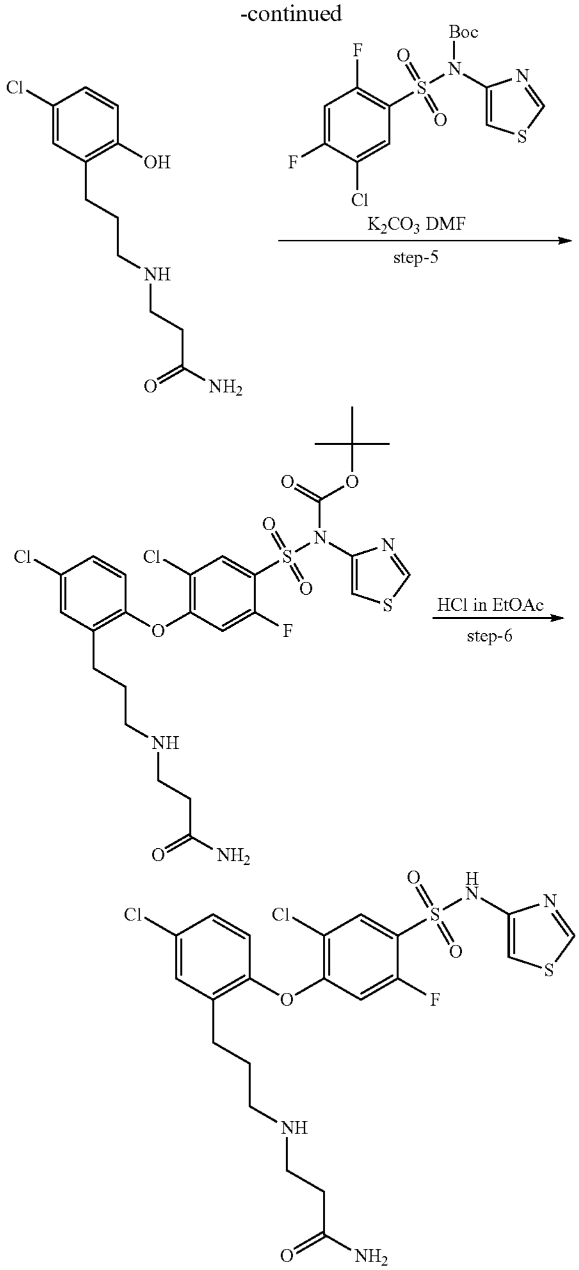

Step 1: Preparation of 3-(5-chloro-2-hydroxyphenyl)acrylaldehyde

To a solution of 5-chloro-2-hydroxybenzaldehyde (20 g, 127 mmol) in THF (300 ml) was added (formylmethylene) triphenylphosphorane (43 g, 140 mmol) at room temperature. The resulting reaction mixture was then refluxed at 100° C. for 20 hrs. After completion of reaction, the reaction mixture was allowed to cool to room temperature. Water (200 ml) was added and the resulting mixture was extracted with ethyl acetate (3×250 ml). The combined organic extract was washed with water (200 ml), brine (200 ml), dried over sodium sulphate and concentrated under vacuo to get the desired crude product. The crude product was purified by column chromatography using normal phase silica gel. The desired product eluted at around 20-30% ethyl acetate in hexane. Evaporation of the product fractions gave 20 g (yield, 87%) of desired compound as yellow solid. LC-MS: m/z=181.34 (M−H).

Step 2: Preparation of methyl 3-[3-(5-chloro-2-hydroxyphenyl)allylamino]propanoate)

To a solution of 3-(5-chloro-2-hydroxyphenyl)acrylaldehyde (1.0 g, 5.47 mmol) and β-Alanine methyl ester hydrochloride (0.917 g, 6.57 mmol) in DCM (20 ml) was added magnesium sulphate (1.317 g, 1.09 mmol) and TEA (2.3 ml, 16.41 mmol) at room temperature and the resulting reaction mixture was stirred at room temperature for 12 hours. The reaction mixture was then concentrated under vacuo. The concentrated mass thus obtained was dissolved in methanol (20 ml) and cooled to 5-10° C. To this cold reaction mixture, sodium borohydrate (0.620 g, 16.41 mmol) was then added in small portions over a period of 10-20 mins, during addition the temperature was maintained in between 10-20° C. After completion of addition the resulting reaction mixture was allowed to stir at room temperature for 2 hours. After completion of the reaction, it was concentrated under vacuo. To the resulting crude mass water (50 ml) was added and the mixture was extracted with EtOAc (3×25 ml). The combined organic extract was washed with water (20 ml), brine (20 ml), dried over sodium sulphate and concentrated under vacuo to get the desired crude product. The crude product was purified by column chromatography using normal phase silica gel. The desired product eluted at around 1-5% Methanol in DCM. Evaporation of the product fractions gave 0.9 g (yield, 61%) of desired compound as white solid. LC-MS: m/z=270.6 (M+H).

Step 3: Preparation of methyl 3-[3-(5-chloro-2-hydroxyphenyl)propylamino]propanoate)

To a solution of 3-[3-(5-chloro-2-hydroxyphenyl)allylamino]propanoate) (0.35 g, 1.3 mmol) in methanol (20 ml) was carefully added 10% Palladium on carbon with 50% moisture (0.104 g, 0.065 mmol). Hydrogen gas was then bubbled into the reaction mixture at room temperature for a period of 30 mins. The reaction mixture was monitored on TLC using ethyl acetate as mobile phase. After completion of the reaction, the reaction mixture was filtered through celite. The celite bed was carefully washed with some amount of methanol. The filtrate thus obtained was concentrated under vacuo to afford 0.3 g (yield, 85%) of desired compound colorless liquid. m/z=272.6 (M+H).

Step 4: Preparation of 3-[3-(5-chloro-2-hydroxyphenyl)propylamino]propanamide)

A solution of methyl 3-[3-(5-chloro-2-hydroxyphenyl) propylamino]propanoate) (0.3 g, 1.08 mmol) in methanolic ammonia (10 mL) was heated at 100° C. in sealed tube (35 mL) for a time period of 12 hours. After completion of reaction methanol was evaporated under vacuo. The crude product was purified by column chromatography using normal phase silica gel. The desired product eluted at around 30-40% ethyl acetate in hexane. Evaporation of the product fractions gave 0.16 g (yield, 33.9%) of the desired compound as a colorless liquid. m/z=257.2 (M+H).

Step 5: Preparation of methyl 3-(3-(2-(4-(N-(tert-butoxycarbonyl)-N-(thiazol-4-yl)sulfamoyl)-2-chloro-5-fluorophenoxy)-5-chlorophenyl)propylamino)propanoate To a solution 3-[3-(5-chloro-2-hydroxyphenyl)propylamino]propanoate) (0.09 g, 0.35 mmol) in DMF (2 ml) was added $K_2CO_3$ (0.145, 1.05 mmol) in one portion under nitrogen atmosphere at room temperature. The resulting reaction mixture was stirred at room temperature for 15 minutes. To the above mixture was added tert-butyl 5-chloro-2,4-difluorophenylsulfonyl(thiazol-4-yl)carbamate (0.143 g, 0.35 mmol) and the resulting mixture was stirred at room temperature for 3 hours. After completion of reaction, water (10 ml) was added and the resulting mixture was extracted with ethyl acetate (3×25 ml). The combined organic extract was washed with water (20 ml), brine (20 ml), dried over sodium sulphate and concentrated under vacuo. The crude product was purified by column chromatography using normal phase silica gel. The desired product eluted at around 20 to 25% ethyl acetate in hexane. Evaporation of the product fractions gave 0.15 g (yield, 66.2%) of desired compound as a solid. This material was used for the next step without any further purification and analysis. The material was used directly for the next step.

Step 6: Preparation of 3-(3-(5-chloro-2(2-chloro-5-fluoro-4-(N-thiazol-4-ylsulfamoyl)phenoxy)phenyl) propylamino)propanamide fluorophenylsulfonyl (thiazol-4-yl)carbamate To a solution of 3-(3-(2-(4-(N-(tert-butoxycarbonyl)-N-(thiazol-4-yl)sulfamoyl)-2-chloro-5-fluorophenoxy)-5-chlorophenyl) propylamino) propanoate (0.15 g, 0.23 mmol) in dichloromethane (5 ml) was added drop-wise a 4N solution of hydrochloric acid in ethyl acetate (0.5 ml) at room temperature. The resulting reaction mixture was stirred room temperature for 2 hours. After completion of reaction, pentane (20 ml) was added in to the reaction mixture which resulted in precipitation of solid. The solvent layer was decanted off; the solid thus obtained was washed twice with pentane (15 ml) and dried under vacuo. The resulting crude material was further purified by Prep HPLC using 0.1% Formic acid in Water:Acetonitrile mobile phase. Evaporation of the pure product fractions obtained from Prep HPLC provided the desired product as HCl salt. (0.009 g, 7.1% yield). LC-MS: m/z=548.8 (M+H). 1H-NMR (MeOD), δ 8.75 (d, J=2.4 Hz, 1H), 8.01 (d, J=7.2 Hz, 1H), 7.48 (d, J=2.4 Hz, 1H), 7.34-7.37 (dd, J=2.4, 8.8 Hz, 1H), 7.06 (d, J=2.4 Hz, 1H), 7.01 (d, J=8.4 Hz, 1H), 6.73 (d, J=10.4 Hz, 1H), 3.22 (t, J=6.4 Hz, 2H), 3.02-3.06 (m, 2H), 2.62-2.70 (m, 4H), 1.99-2.03 (m, 2H).

Example 27: 2-(N-(3-(5-chloro-2-(2-chloro-5-fluoro-4-(N-(thiazol-4-yl)sulfamoyl)phenoxy)phenyl)propyl)acetamido)acetic Acid Scheme 12

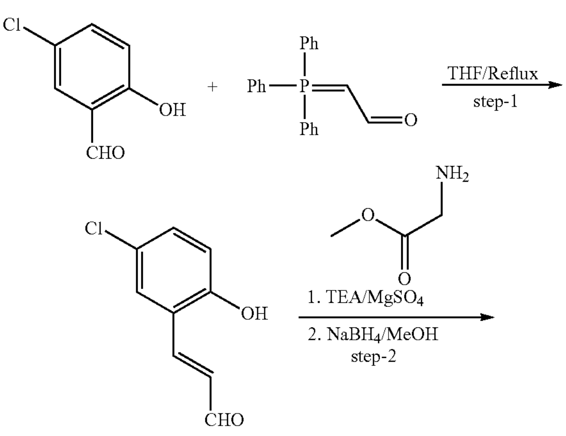

-continued

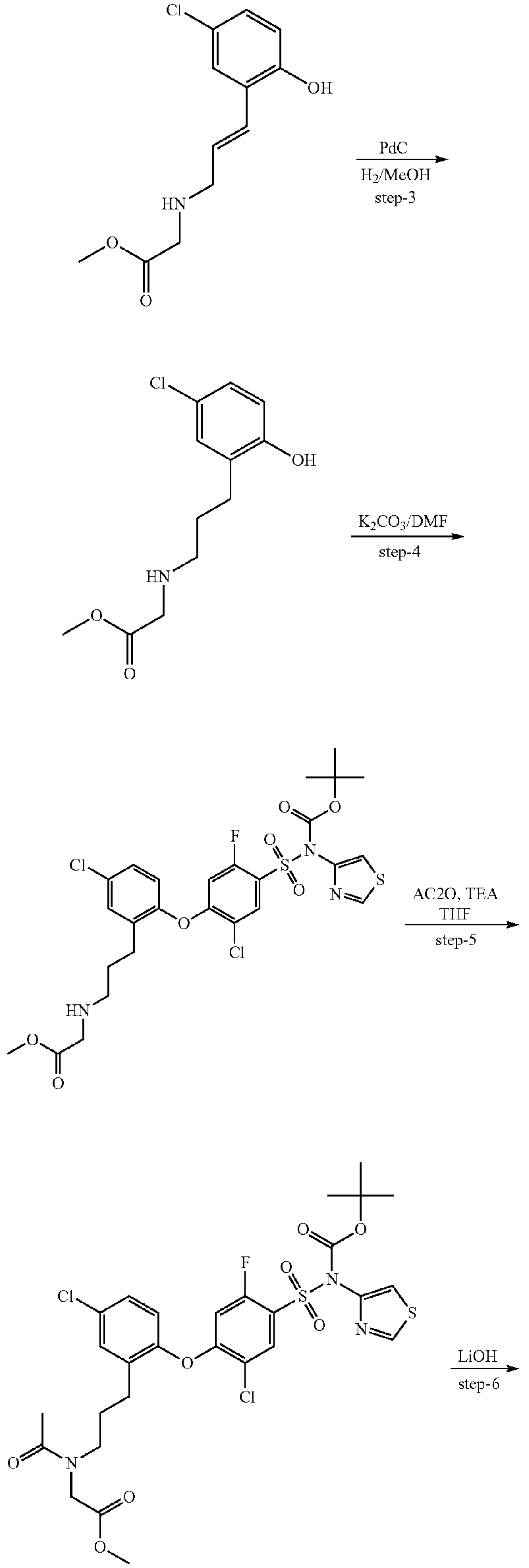

-continued

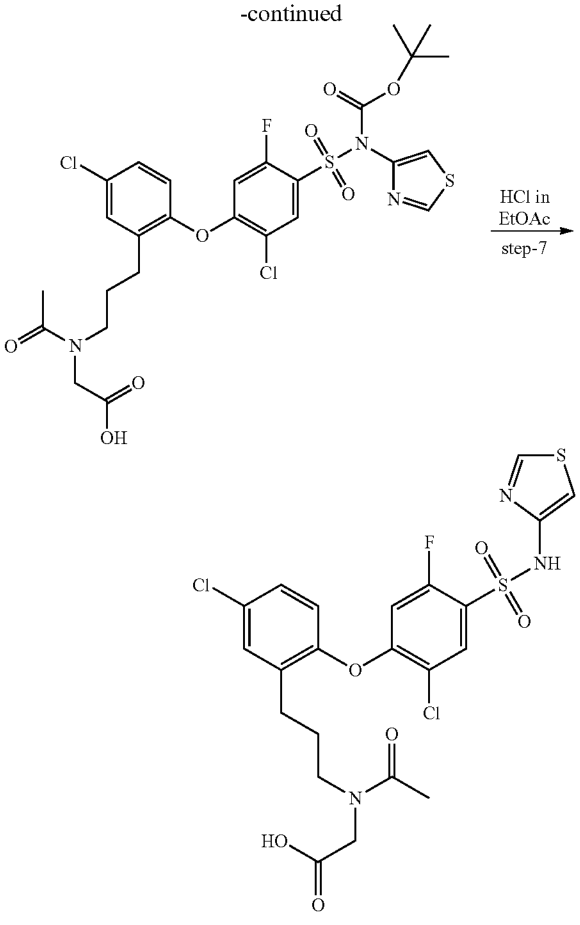

COB-508

Step 1: Preparation of (E)-3-(5-chloro-2-hydroxyphenyl) Acrylaldehyde

To a solution of 5-chloro-2-hydroxybenzaldehyde (20 g, 127 mmol) in THF (300 ml) was added (formylmethylene) triphenylphosphorane (43 g, 140 mmol) at room temperature. The resulting reaction mixture was then refluxed at 100° C. for 20 hrs. After completion of reaction, the reaction mixture was allowed to cool to room temperature. Water (200 ml) was added and the resulting mixture was extracted with ethyl acetate (3×250 ml). The combined organic extract was washed with water (200 ml), brine (200 ml), dried over sodium sulphate and concentrated under vacuo to get the desired crude product. The crude product was purified by column chromatography using normal phase silica gel. The desired product eluted at around 20-30% ethyl acetate in hexane. Evaporation of the product fractions gave 20 g (yield, 87%) of the desired compound as a yellow solid LC-MS: m/z=183.4 (M+H).

Step 2: Preparation of (E)-methyl 2-(3-(5-chloro-2-hydroxyphenyl)allylamino)acetate To a solution of (E)-3-(5-chloro-2-hydroxyphenyl)acrylaldehyde (1.0 g, 5.4 mmol) and glycine methyl ester hydrochloride (0.590 g, 6.55 mmol) in dichloromethane (20 ml) was added magnesium sulphate (1.5 g, 10.9 mmol) and triethylamine (2.28 ml, 16.38 mmol) at room temperature.

The above reaction mixture was stirred at room temperature for 12 hours. The resulting reaction mixture was then concentrated under vacuo. The concentrated mass thus obtained was dissolved in methanol (20 ml) and cooled to a temperature between 5-10° C. To the above mixture, sodium borohydride (0.606 g, 16.38 mmol) was added in small portions over a period of 10 minutes; during addition temperature of the reaction mixture was maintained between 10-20° C. After completion of addition, the resulting reaction mixture was allowed to stir at room temperature for 2 hours. After completion of reaction, the reaction mixture was concentrated under vacuo. Water (40 ml) was added to the above crude mass and the resulting mixture was extracted with ethyl acetate (3×60 ml). The combined organic extract was washed with water (50 ml), brine (50 ml), dried over sodium sulphate and concentrated under vacuo to get the desired crude product. The crude product was purified by column chromatography using normal phase silica gel. The desired product eluted at around 2-3% methanol in dichloromethane. Evaporation of the product fractions gave 0.8 g (yield, 57.4%) of the desired compound as a brown liquid. LC-MS: m/z=256.07 (M+H).

Step 3: Preparation of methyl 2-(3-(5-chloro-2-hydroxyphenyl)propylamino)acetate To a solution of (E)-methyl 2-(3-(5-chloro-2-hydroxyphenyl)allylamino)acetate (0.8 g, 3.13 mmol) in methanol (50 ml) was carefully added Palladium hydroxide (0.199 g, 0.09 mmol). Hydrogen gas was then bubbled into the reaction mixture at room temperature for a period of 30 minutes. After completion of the reaction, the reaction mixture was filtered through celite. The celite bed was carefully washed with some amount of methanol. The filtrate thus obtained was concentrated under vacuo to afford 0.7 g (yield, 86.81%) of compound as colorless liquid. LC-MS: m/z=258.07 (M+H).

Step 4: Preparation of methyl 2-(3-(2-(4-(N-(tert-butoxycarbonyl)-N-(thiazol-4-yl)sulfamoyl)-2-chloro-5-fluorophenoxy)-5-chlorophenyl)propylamino)acetate To a solution of methyl 2-(3-(5-chloro-2-hydroxyphenyl)propylamino)acetate (0.7 g, 2.72 mmol) in DMF (7 ml) was added $K_2CO_3$ (1.12 g, 8.17 mmol) in one portion under nitrogen atmosphere at room temperature. The resulting reaction mixture was then stirred at room temperature for 15 minutes. To the above mixture was added tert-butyl 5-chloro-2,4-difluorophenylsulfonyl(thiazol-4-yl)carbamate (1.22 g, 2.996 mmol) and the resulting reaction mixture was stirred at room temperature for 3 hours. After completion of reaction, water (20 ml) was added and the resulting mixture was extracted with ethyl acetate (3×50 ml). The combined organic extract was washed with water (20 ml), brine (20 ml), dried over sodium sulphate and concentrated under vacuo to afford 0.54 g (yield, 30.64%) of the compound as a white solid. LC-MS: m/z=646.20 (M−H).

Step 5: Preparation of methyl 2-(N-(3-(2-(4-(N-(tert-butoxycarbonyl)-N-(thiazol-4-yl)sulfamoyl)-2-chloro-5-fluorophenoxy)-5-chlorophenyl)propyl)acetamido)acetate To a solution of methyl 2-(3-(2-(4-(N-(tert-butoxycarbonyl)-N-(thiazol-4-yl)sulfamoyl)-2-chloro-5-fluorophenoxy)-5-chlorophenyl)propylamino)acetate (0.35 g, 0.54 mmol) in THF (5 mL) was added triethyl amine (0.22 ml, 1.62 mmol). The resulting reaction mixture was stirred at 0° C. for 5-10 minutes. Acetic anhydride (0.102 ml, 1.08 mmol) was added at 0° C. The resulting reaction mixture was then refluxed at 80° C. for 12 hours. To the reaction mixture water (30 ml) was added and the resulting mixture was extracted with ethyl acetate (3×50 ml). The combined organic extracts was washed with water (30 ml), brine (30 ml), dried over sodium sulphate and concentrated under vacuum to get the desired crude product. The crude product was purified by triturating with diethyl ether. Evaporation of the product fractions gave 0.35 g (yield, 94.01%) of the desired compound as a brown solid. LC-MS: m/z=690.5 (M+H).

Step 6: Preparation of 2-(N-(3-(2-(4-(N-(tert-butoxycarbonyl)-N-(thiazol-4-yl)sulfamoyl)-2-chloro-5-fluorophenoxy)-5-chlorophenyl)propyl)acetamido)acetic Acid To the solution of methyl 2-(N-(3-(2-(4-(N-(tert-butoxycarbonyl)-N-(thiazol-4-yl)sulfamoyl)-2-chloro-5-fluorophenoxy)-5-chlorophenyl)propyl)acetamido)acetate (0.35 g, 0.50 mmol) in THF (5 ml) was added a solution of lithium hydroxide monohydrate (0.212 g, 5.07 mmol) in water (0.5 ml) at room temperature. The resulting reaction mixture was stirred at room temperature for 3 hours. After completion of reaction ice cold water (15 ml) was added in to the reaction mixture, the resulting mixture was then acidified between 4-6 pH with aqueous 1N hydrochloric acid. The resulting acidic aqueous was extracted with ethyl acetate (3×25 ml). The combined organic extract was washed with water (20 ml), brine (20 ml), dried over sodium sulphate and concentrated under vacuo to afford 0.3 g (yield, 87.49%) of the compound as a white solid. This material was directly used for next step without any further purification and analysis. LC-MS: m/z=676.41 (M+H).

Step 7: Preparation of 2-(N-(3-(5-chloro-2-(2-chloro-5-fluoro-4-(N-thiazol-4-ylsulfamoyl) phenoxy)phenyl) propyl)acetamido)acetic Acid To the solution of 2-(N-(3-(2-(4-(N-(tert-butoxycarbonyl)-N-(thiazol-4-yl)sulfamoyl)-2-chloro-5-fluorophenoxy)-5-chlorophenyl)propyl)acetamido)acetic acid (0.3 g, 0.44 mmol) in dichloromethane (4 ml) was added drop-wise a 4N solution of hydrochloric acid in ethyl acetate (1 ml) at room temperature. The resulting reaction mixture was stirred room temperature for 2 hours. After completion of reaction, pentane (20 ml) was added in to the reaction mixture which resulted in precipitation of solid. The solvent layer was decanted off; the solid thus obtained was washed twice with pentane (15 ml) and dried under vacuo. The resulting crude material was further purified by Prep HPLC using 0.1% Hydrochloric acid in water:acetonitrile mobile phase. Evaporation of the pure product fractions obtained from Prep HPLC provided the desired product as HCl salt (0.060 g, 23.47% yield). LC-MS: m/z=575.92 (M+H).

Example 28: 2-(1-(3-(2-(4-(N-(1,2,4-thiadiazol-5-yl)sulfamoyl)-2-chloro-5-fluorophenoxy)-5-chlorophenyl)propyl)piperidin-4-yl)acetic Acid Compound 28 was synthesized according to the procedure described for the synthesis of compound 11 by replacing glycine methyl ester with methyl 2-(piperidin-4-yl)acetate in step 2, and replacing tert-butyl 5-chloro-2,4-difluorophenylsulfonyl(thiazol-4-yl)carbamate with 5-chloro-N-(2,4-dimethoxybenzyl)-2,4-difluoro-N-(1,2,4-thiadiazol-5-yl)benzenesulfonamide in step 4. LC-MS: m/z=601.2 (M+H).

Example 29: 3-((3-(5-chloro-2-(2-chloro-5-fluoro-4-(N-(thiazol-2-yl)sulfamoyl)phenoxy)phenyl)propyl)amino)propanoic Acid Compound 29 was synthesized according to the procedure described for the synthesis of compound 11 by replacing glycine methyl ester with beta alanine methyl ester in step 2, and replacing tert-butyl 5-chloro-2,4-difluorophenylsulfonyl(thiazol-4-yl)carbamate with 5-chloro-N-(2,4-dimethoxybenzyl)-2,4-difluoro-N-(thiazol-2-yl)benzenesulfonamide in step 4. LC-MS: m/z=547.9 (M+H). 1H-NMR (MeOD), δ 8.05 (d, J=6.8 Hz, 1H), 7.49 (d, J=2.8 Hz, 1H), 7.34 (dd, J=2.4, 8.4 Hz, 1H), 7.17 (d, J=4.4 Hz, 1H), 7.02 (d, J=8.4 Hz, 1H), 6.80 (d, J=4.4 Hz, 1H), 6.75 (d, J=10.4 Hz, 1H), 3.14 (t, J=6.4 Hz, 2H), 3.04 (t, J=8.0 Hz, 2H), 2.71 (t, J=8.0 Hz, 2H), 2.49 (t, J=6.4 Hz, 2H), 2.00-2.03 (m, 2H).

Example 30: 2-((3-(5-chloro-2-(2-chloro-5-fluoro-4-(N-(thiazol-4-yl)sulfamoyl)phenoxy)phenyl)propyl)amino)-N-methylacetamide Compound 30 was synthesized according to the procedure described for the synthesis of compound 11 by replacing glycine methyl ester with 2-amino-N-methylacetamide in step 2. LC-MS: m/z=547.1 (M+H). 1H-NMR (MeOD), δ 8.77 (d, J=2.4 Hz, 1H), 8.01 (d, J=7.2 Hz, 1H), 7.48 (d, J=2.4 Hz, 1H), 7.35 (dd, J=2.4, 8.4 Hz, 1H), 7.10 (d, J=2.0 Hz, 1H), 7.02 (d, J=8.8 Hz, 1H), 6.73 (d, J=10.4 Hz, 1H), 3.70 (s, 2H), 2.97-3.02 (m, 2H), 2.80 (s, 3H), 2.65-2.69 (m, 2H), 1.96-2.06 (m, 2H).

Example 31: 5-chloro-4-(4-chloro-2-(3-((2-(methylsulfonyl)ethyl)amino)propyl)phenoxy)-2-fluoro-N-(thiazol-4-yl)benzenesulfonamide Compound 31 was synthesized according to the procedure described for the synthesis of compound 11 by replacing glycine methyl ester with 2-(methylsulfonyl)ethanamine in step 2. LC-MS: m/z=581.8 (M+H). 1H-NMR (MeOD), δ 8.77 (d, J=2.4 Hz, 1H), 8.02 (d, J=6.8 Hz, 1H), 7.48 (d, J=2.4 Hz, 1H), 7.36 (dd, J=2.8, 8.8 Hz, 1H), 7.10 (d, J=2.4 Hz, 1H), 7.02 (d, J=8.4 Hz, 1H), 6.73 (d, J=10.4 Hz, 1H), 3.33-3.50 (m, 4H), 3.03 (s, 3H), 2.99-3.01 (m, 2H), 2.65-2.68 (m, 2H), 1.95-2.03 (m, 2H).

Example 32: 1-(3-(2-(4-(N-(1,2,4-thiadiazol-5-yl)sulfamoyl)-2-chloro-5-fluorophenoxy)-5-chlorophenyl)propyl)piperidine-4-carboxylic Acid Compound 32 was synthesized according to the procedure described for the synthesis of compound 11 by replacing glycine methyl ester with methyl piperidine-4-carboxylate in step 2, and replacing tert-butyl 5-chloro-2,4-difluorophenylsulfonyl(thiazol-4-yl)carbamate with 5-chloro-N-(2,4-dimethoxybenzyl)-2,4-difluoro-N-(1,2,4-thiadiazol-5-yl)benzenesulfonamide in step 4. LC-MS: m/z=589.6 (M+H).

Example 33: 5-chloro-4-(4-chloro-2-(4,5,6,7-tetrahydropyrazolo[1,5-a]pyrimidin-3-yl)phenoxy)-2-fluoro-N-(thiazol-4-yl)benzenesulfonamide Scheme 13

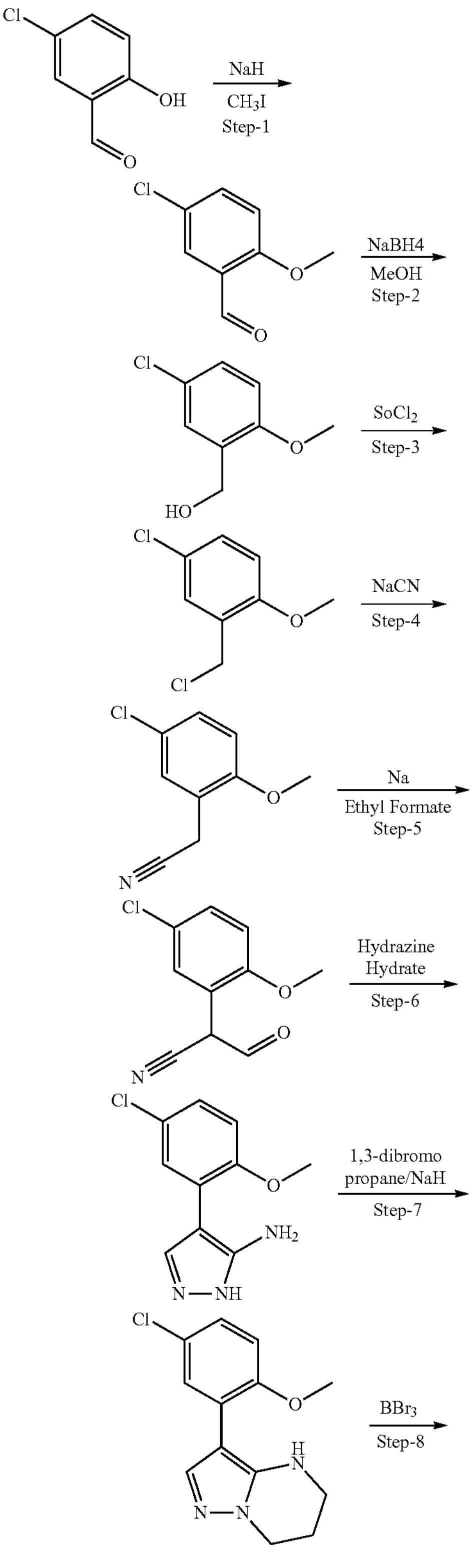

-continued

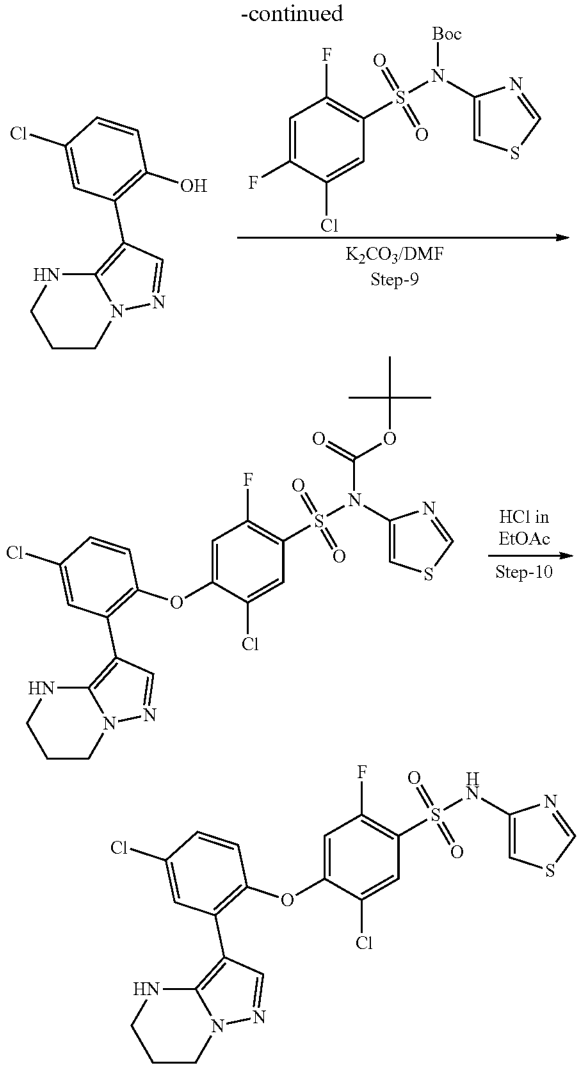

Step 1: Preparation of 5-chloro-2-methoxybenzaldehyde

A solution of 5-chloro-2-hydroxybenzaldehyde (20 g, 128 mmol) in DMF (70 mL) was cooled to a temperature between 5-10° C. Sodium hydride (7.69 g, 192 mmol) was added to the above solution in small portions over a period of 20 minutes. Methyl iodide (23.8 ml, 384 mmol) was then added drop wise to the above reaction mixture whilst maintaining its temperature below 15° C. After completion of addition the reaction mixture was stirred at room temperature for 2 hours. Thereafter the reaction mixture was poured in to cold saturated ammonium chloride solution (250 mL) to get white precipitates. The precipitates thus formed were filtered off and dried under vacuo. The resulting solid was triturated with 100 ml of pentane:diethyl ether (4:1) to afford 18 g (yield, 82.58%) of the desired compound as a white solid. LC-MS: m/z=170.1 (M+H).

Step 2: Preparation of (5-chloro-2-methoxyphenyl) Methanol

A solution of 5-chloro-2-methoxybenzaldehyde (18 g, 105.8 mmol) in methanol (100 mL) was cooled to temperature in between 5-10° C. To the above solution sodium borohydride (11.8 g, 317 mmol) was added in portion over a period of 30 mins. After completion of addition the resulting reaction mixture was allowed to stir at room temperature for next ~2 hours. The reaction was monitored on TLC using ethyl acetate:hexane (1:1) as mobile phase. After completion of the reaction, it was concentrated under vacuo. To the resulting crude mass, cold water (200 ml) was added to get white precipitate. The precipitate thus formed was filtered and dried to afford 16 g (yield, 87.8%) of desired compound as white solid. The material was used directly for the next step.

Step 3: Preparation of 4-chloro-2-(chloromethyl)-1-methoxybenzene

A solution of 5-chloro-2-methoxyphenyl)methanol (16 g, 94 mmol) in DCM (100 ml) was cooled to a temperature between 5-10° C. To the above solution thionyl chloride (11 ml, 140 mmol) was added drop wise over a period of 30 minutes. After completion of addition the resulting reaction mixture was allowed to stir at room temperature for 4 hours. After completion of the reaction, it was concentrated under vacuo. To the resulting crude mass, cold water (150 ml) was added to get white precipitates. The precipitate thus formed was filtered off and dried under vacuo to afford 12 g (yield, 67.9%) of the desired compound as a white solid. The material was used directly for the next step.

Step 4: Preparation of 2-(5-chloro-2-methoxyphenyl)acetonitrile

To a solution of 4-chloro-2-(chloromethyl)-1-methoxybenzene (12 g, 63.15 mmol) in DMSO (60 mL) was carefully added sodium cyanide (4.4 g, 95.6 mmol) at room temperature. Above reaction mixture was then heated at 100° C. for 3 hours. After cooling to room temperature, the reaction mixture was poured in to cold water (200 mL) to get precipitates. The precipitate thus formed were filtered off and dried under vacuo to afford 10 g (yield, 87.46%) of the desired compound as an off white solid. The material was used directly for the next step.

Step 5: Preparation of 2-(5-chloro-2-methoxyphenyl)-3-oxopropanenitrile

To a solution of 2-(5-chloro-2-methoxyphenyl)acetonitrile (10 g, 47.84 mmol) in ethyl formate (50 mL) was added sodium metal (4.4 g, 95.6 mmol) at room temperature. The resulting reaction mixture was heated at 100° C. for 3 hours. After completion of the reaction, it was cooled to room temperature, water (100 ml) and dichloromethane (100 ml) were added to the reaction mixture and the solution was adjusted to pH-3 with the help of concentrated hydrochloric acid. The layers were separated and the aqueous layer was extracted with dichloromethane (2×100 ml). The combined organics were washed with saturated aqueous sodium chloride solution (150 ml), dried over sodium sulphate, filtered and evaporated in vacuo. The crude product was purified by column chromatography using normal phase silica gel. The desired product eluted at around 0.7 to 0.9% methanol in dichloromethane. Evaporation of the product fractions gave 9 g (yield, 77.94%) of the desired compound as a white solid. LC-MS: m/z=208.0 (M−H).

Step 6: Preparation of 4-(5-chloro-2-methoxyphenyl)-1H-pyrazol-5-amine

To a solution of 2-(5-chloro-2-methoxyphenyl)-3-oxopropanenitrile (9 g, 43 mmol) in ethanol (90 mL) was added hydrazine hydrate (4.3 g, 86.12 mmol) and glacial acetic acid (2.7 mL, 51.6 mmol) at room temperature. The reaction mixture was then heated under reflux for 3 hours. After completion of the reaction, the reaction mixture was cooled to room temperature and quenched with aqueous sodium bicarbonate (150 ml). The resulting mixture was extracted with dichloromethane (3×100 ml). The combined organic layers were washed with brine, dried over sodium sulphate and concentrated in vacuo. The crude product was purified by column chromatography using normal phase silica gel. The desired product eluted at around 0.9 to 1.1% methanol in dichloromethane. Evaporation of the product fractions gave 7 g (yield, 72.8%) of the desired compound as a white solid. LC-MS: m/z=224.1 (M+H).

Step 7: Preparation of 3-(5-chloro-2-methoxyphenyl)-4,5,6,7-tetrahydropyrazolo[1,5-a]pyrimidine A solution of 4-(5-chloro-2-methoxyphenyl)-1H-pyrazol-5-amine (3 g, 13.45 mmol) in dry DMF (15 mL) was cooled to a temperature in between 5-10° C. Sodium hydride (0.806 g, 20.17 mmol) was added to the above solution in small portions over a period of 30 minutes. The resulting reaction mixture was stirred for 30 minutes at 5-10° C., thereafter 1,3-dibromopropane (1.78 ml, 17.48 mmol) was added drop wise to the above mixture. The resulting reaction mixture was heated at 100° C. for a period of 4 hrs. After completion of reaction, the solution was diluted with cold water (100 mL) and the product was extracted with ethyl acetate (3×100). The combined organic layers were washed with brine, dried over sodium sulphate and concentrated in vacuo. The crude product was purified by column chromatography using normal phase silica gel. The desired product eluted at around 1.2 to 1.5% methanol in dichloromethane. Evaporation of the product fractions gave 0.65 g (yield, 18.36%) of the desired compound as a semisolid. LC-MS: m/z=264.2 (M+H).

Step 8: Preparation of 4-chloro-2-(4,5,6,7-tetrahydropyrazolo[1,5-a]pyrimidin-3-yl)phenol A solution of 3-(5-chloro-2-methoxyphenyl)-4,5,6,7-tetrahydropyrazolo[1,5-a]pyrimidine (0.65 g, 1.9 mmol) in dichloromethane (30 mL) was cooled to a temperature between 5-10° C. To the above solution, boron tribromide in dichloromethane (4.7 mL, 4.75 mmol) was added drop wise over a period of 30 minutes. After completion of addition, the resulting reaction mixture was stirred at room temperature for 4 hours. After completion of reaction, the solution was diluted with cold water (40 mL) and the product was extracted with ethyl acetate (3×30 mL). The combined organic layers were washed with brine, dried over sodium sulphate and concentrated in vacuo to afford 0.65 g (yield, 81.24%) of desired compound as white solid. LC-MS: m/z=250.2 (M+H).

Step 9: Preparation of tert-butyl 5-chloro-4-(4-chloro-2-(4,5,6,7-tetrahydropyrazolo[1,5-a]pyrimidin-3-yl)phenoxy)-2-fluorophenylsulfonyl(thiazol-4-yl)carbamate To a solution 4-chloro-2-(4,5,6,7-tetrahydropyrazolo[1,5-a]pyrimidin-3-yl)phenol (0.5 g, 2.008 mmol) in DMF (8 ml) was added $K_2CO_3$ (0.556 g, 4.016 mmol) in one portion under nitrogen atmosphere at room temperature. The resulting reaction mixture was stirred at room temperature for 15 minutes. To the above mixture was added tert-butyl 5-chloro-2,4-difluorophenylsulfonyl(thiazol-4-yl)carbamate (0.989 g, 2.409 mmol) and the resulting reaction mixture was stirred at room temperature for 3 hours. After completion of reaction, water (10 ml) was added and the resulting mixture was extracted with ethyl acetate (3×25 ml). The combined organic extract was washed with water (20 ml), brine (20 ml), dried over sodium sulphate and concentrated under vacuo. The crude product was purified by column chromatography using normal phase silica gel. The desired product eluted at around 40 to 50% ethyl acetate in hexane. Evaporation of the product fractions gave 0.4 g (yield, 31.18%) of the desired compound as a white solid. LC-MS: m/z=640.1 (M+H).

Step 10: Preparation of 5-chloro-4-(4-chloro-2-(4,5,6,7-tetrahydropyrazolo[1,5-a]pyrimidin-3-yl)phenoxy)-2-fluoro-N-(thiazol-4-yl)benzenesulfonamide To a solution of tert-butyl 5-chloro-4-(4-chloro-2-(4,5,6,7-tetrahydropyrazolo[1,5-a]pyrimidin-3-yl)phenoxy)-2-fluorophenylsulfonyl(thiazol-4-yl)carbamate (0.4 g, 0.626 mmol) in dichloromethane (15 ml) was added drop-wise a 4N solution of hydrochloric acid in ethyl acetate (0.8 ml) at room temperature. The resulting reaction mixture was stirred at room temperature for 2 hours. After completion of reaction, pentane (20 ml) was added in to the reaction mixture which resulted in precipitation of solid. The solvent layer was decanted off; the solid thus obtained was washed twice with pentane (15 ml) and dried under vacuo. The resulting crude material was further purified by Prep HPLC using 0.1% Hydrochloric acid in Water:Acetonitrile mobile phase. Evaporation of the pure product fractions obtained from Prep HPLC provided the desired product as HCl salt (0.130 g, 38.6% yield). LC-MS: m/z=539.78 (M+H). 1H NMR (400 MHz, Methanol-d4) δ 8.76 (d, J=2.4 Hz, 1H), 8.02 (s, 1H), 7.95 (d, J=7.2 Hz, 1H), 7.61 (d, J=2.4 Hz, 1H), 7.54 (dd, J=2.4, 8.4 Hz, 1H), 7.27 (d, J=8.4 Hz, 1H), 7.09 (d, J=2.0 Hz, 1H), 6.62 (d, J=10.8 Hz, 1H), 4.14 (t, J=6.0 Hz, 2H), 3.40 (t, J=5.6 Hz, 2H), 2.14 (p, J=6.0 Hz, 2H).

The embodiments described herein are intended to be merely exemplary, and those skilled in the art will recognize, or be able to ascertain using no more than routine experimentation, numerous equivalents to the specific procedures described herein. All such equivalents are considered to be within the scope of the present invention and are covered by the following embodiments.

All references (including patent applications, patents, and publications) cited herein are incorporated herein by reference in their entirety and for all purposes to the same extent as if each individual publication or patent or patent application was specifically and individually indicated to be incorporated by reference in its entirety for all purposes.

What is claimed is:

1. A compound of Formula (I),

Formula (I)

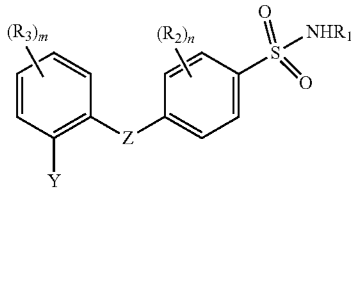

or a pharmaceutically acceptable salt, or a stereoisomeric or tautomeric form thereof, wherein:

Z is —O— or —S—;

Y is —X—C(═O)$NR_4R_5$, $(CH_2)_3$—$NR_9R_{10}$, or 4,5,6,7-tetrahydropyrazolo[1,5-a]pyrimidine-(2-yl or 3-yl);

X is ($C_6$-$C_{10}$)aryl or 5- or 6-membered heteroaryl;

$R_1$ is a partially unsaturated or aromatic 5- or 6-membered heterocycle;

$R_2$ is independently at each occurrence —F, —Cl, —Br, —$CH_3$ or —CN;

$R_3$ is independently at each occurrence —H, —F, —Cl, —Br, —$CF_3$, —$OCF_3$, —CN, ($C_1$-$C_{12}$)alkyl, or ($C_1$-$C_{12}$)alkoxy;

$R_4$ and $R_5$ are each independently H, ($C_1$-$C_9$)alkyl, or ($C_4$-$C_{12}$)cycloalkyl; with the proviso that:

$R_4$ and $R_5$ are not both H; and at least one of $R_4$ and $R_5$ independently is substituted with 1 or 2 substituents selected from the group consisting of —$CO_2H$, —$CO_2R_6$, —CN, —OH, —$CONR_7R_8$, and —$NR_7R_8$; wherein:

$R_6$ is ($C_1$-$C_{12}$)alkyl;

$R_7$ and $R_8$ are each independently H, ($C_1$-$C_{12}$)alkyl, or $R_7$ and $R_8$ together form a 4- to 7-membered heterocycloalkyl ring;

$R_9$ is ($C_1$-$C_6$)alkyl, ($C_3$-$C_8$)cycloalkyl, pyrazolyl or pyridinyl; wherein $R_9$ is optionally further substituted with 1 or 2 substituents selected from the group consisting of —COOH, —$COOR_{11}$, —$CONR_{11}R_{12}$, —$SO_2R_{11}$, —$SO_2NR_{11}R_{12}$, —OH, —CN, —$OR_{11}$, and —$NR_{11}R_{12}$; wherein $R_{11}$ and $R_{12}$ may form a 6 membered heterocycloalkyl ring $R_{10}$ is $R_{11}$, —$COR_{11}$, —$COOR_{11}$, —$SO_2R_{11}$, 5-methyl-2-oxo-1,3-dioxol-4-yl,

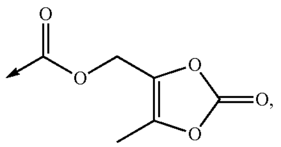

—COO—$CH(CH_3)OCOCH(CH_3)_2$; or $R_9$ and $R_{10}$ together form a piperazinone or a 4- to 8-membered heterocycloalkyl ring, wherein said heterocycloalkyl ring is substituted with 1 or 2 substituents selected from the group consisting of —COOH, —$COOR_{11}$, —$CH_2$—$COOR_{11}$, —OH, —$NH_2$, —CN, and ($C_1$-$C_8$)alkoxy;

$R_{11}$ and $R_{12}$ are independently H or ($C_1$-$C_6$)alkyl, optionally substituted with 4- to 8-membered heterocycloalkyl ring; and m and n are each independently 1, 2, 3, or 4.

2. The compound of claim 1, wherein Y is —$(CH_2)_3$—$NR_9R_{10}$.

3. The compound of claim 1, wherein $R_1$ is an aromatic 5- or 6-membered heterocycle, with 1-3 heteroatoms independently selected from the group consisting of N, O, and S.

4. The compound of claim 1, wherein $R_2$ is independently at each occurrence —F or —Cl.

5. The compound of claim 1, wherein n is 1, 2, or 3.

6. The compound of claim 1, wherein Z is —O.

7. The compound of claim 1, wherein $R_3$ is independently at each occurrence —H, —F, —Cl, or —Br.

8. The compound of claim 1, wherein m is 1, 2, or 3.

9. The compound of claim 1, wherein $R_9$ is ($C_1$-$C_6$)alkyl; wherein $R_9$ is optionally further substituted with 1 or 2 substituents selected from the group consisting of —COOH, —Come, —$CONH_2$, and —$NH_2$.

10. The compound of claim 1, wherein $R_{10}$ is —H, —COMe, —Coot.

11. The compound of claim 1, wherein $R_9$ and $R_{10}$ together form a 4 to 8 membered heterocycloalkyl ring, wherein said heterocycloalkyl ring is substituted with 1 or 2 groups selected from the group consisting of —COOH, —Come, —Coot, —$CH_2$—COOH, and —$NH_2$.

12. The compound of claim 1, wherein $R_9$ and $R_{10}$ together form a piperidine substituted with 1 or 2 groups selected from the group consisting of —COOH, —Come, —Coot, —$CH_2$—COOH, —$CH_2$—COOMe, —$CH_2$—COOEt, and —$NH_2$.

13. A pharmaceutical composition comprising a compound of claim 1, or a pharmaceutically acceptable salt, or tautomeric form thereof, and a pharmaceutically acceptable carrier.

14. The composition of claim 13, wherein the composition is suitable for topical, oral, subcutaneous, or intravenous administration.

15. A method for treatment of pain in a subject, wherein the method comprises administering to the subject in need of such treatment a therapeutically effective amount of a compound of claim 1, or a pharmaceutically acceptable salt, or tautomeric form thereof.

16. The method of claim 15, wherein the therapeutically effective amount to alleviate pain in a subject is at a dose between 0.1 mg/kg and 1,000 mg/kg, at a dose between 0.5 mg/kg and 100 mg/kg, or at a dose between 1 mg/kg to 50 mg/kg.

17. The method of claim 15, wherein the pain comprises or results from painful conditions comprising: nociceptive pain, myofascial pain; neuropathic pain, pain with nociceptive and neuropathic components; visceral pain; headache pain; CRPS; CRPS type I; CRPS type II; RSD; reflex neurovascular dystrophy; reflex dystrophy; sympathetically maintained pain syndrome; causalgia; Sudeck atrophy of bone; algoneurodystrophy; shoulder hand syndrome; post-traumatic dystrophy; autonomic dysfunction; autoimmune-related pain; inflammation-related pain; cancer-related pain; phantom limb pain; chronic fatigue syndrome; post-operative pain; spinal cord injury pain; central post-stroke pain; radiculopathy; sensitivity to temperature, light touch or color change to the skin (allodynia); pain from hyperthermic or hypothermic conditions; diabetic neuropathy, luetic neuropathy, postherpetic neuralgia, trigeminal neuralgia); chronic pain; or acute pain.

18. The method of claim 15, wherein the compound is a voltage-gated sodium channel inhibitor of NaV1.7.

19. The method of claim 15, wherein the pain is neuropathic or inflammatory pain.

20. The method of claim 17, wherein the nociceptive pain is pain resulting from or associated with a cut or contusion of the skin, a chemical or thermal burn, osteoarthritis, rheumatoid arthritis or tendonitis.

21. The method of claim 17, wherein the neuropathic pain is pain resulting from or associated with stroke, diabetic neuropathy, luetic neuropathy, postherpetic neuralgia, trigeminal neuralgia, fibromyalgia, or painful neuropathy induced iatrogenically by drugs.

22. The method of claim 17, wherein the headache pain is migraine headache pain.

* * * * *